United States Patent
Davidson et al.

(10) Patent No.: US 12,290,651 B2
(45) Date of Patent: May 6, 2025

(54) DEVICES AND METHODS FOR THE TREATMENT OF BODY SURFACE DISORDERS

(71) Applicant: Verrica Pharmaceuticals Inc., West Chester, PA (US)

(72) Inventors: Matthew Gene Davidson, Venice, CA (US); Jayson Michael Rieger, Charlottesville, VA (US); Eugene Scavola, Charlottesville, VA (US); Paul Daly, Plymouth, NH (US); Howard Welgus, West Chester, PA (US)

(73) Assignee: Verrica Pharmaceuticals Inc., West Chester, PA (US)

( * ) Notice: Subject to any disclaimer, the term of this patent is extended or adjusted under 35 U.S.C. 154(b) by 980 days.

(21) Appl. No.: 16/621,854

(22) PCT Filed: Jun. 15, 2018

(86) PCT No.: PCT/US2018/037808
§ 371 (c)(1),
(2) Date: Dec. 12, 2019

(87) PCT Pub. No.: WO2018/232277
PCT Pub. Date: Dec. 20, 2018

(65) Prior Publication Data

US 2021/0138214 A1    May 13, 2021

Related U.S. Application Data

(60) Provisional application No. 62/615,429, filed on Jan. 9, 2018, provisional application No. 62/520,504, filed on Jun. 15, 2017.

(51) Int. Cl.
*A61M 35/00*    (2006.01)
*A61K 31/365*    (2006.01)
(Continued)

(52) U.S. Cl.
CPC ......... *A61M 35/003* (2013.01); *A61K 31/365* (2013.01); *A61K 47/10* (2013.01);
(Continued)

(58) Field of Classification Search
CPC . A61M 35/003; A61M 35/00; A61M 2210/04
See application file for complete search history.

(56) References Cited

U.S. PATENT DOCUMENTS

| 600,556 A | 3/1898 | Schupphaus |
| 1,744,893 A * | 1/1930 | Hein ....................... A61M 5/28 604/200 |

(Continued)

FOREIGN PATENT DOCUMENTS

| CH | 204207 A | 4/1939 |
| CN | 1571795 A | 1/2005 |

(Continued)

OTHER PUBLICATIONS

Extended European Search Report, mailed Feb. 2, 2021, in connection with EP 18813599.0.
(Continued)

*Primary Examiner* — Jessica Arble
(74) *Attorney, Agent, or Firm* — Wolf, Greenfield & Sacks, P.C.

(57) ABSTRACT

Applicator devices (1), kits, systems, and methods of using such devices for treating one or more body surface conditions (e.g., warts, Molluscum contagiosum, conjunctivitis, otitis) are provided. The applicator device facilitates topical administration of a controllable amount of a pharmaceutical composition to a desired area of an affected body surface (e.g., skin, eye, ear, nose, mouth, anus, vagina). The applicator device includes an ampule (40) containing the pharmaceutical composition, the ampule being positioned within a tube (50). Squeezing the tube breaks the ampule, releasing
(Continued)

the pharmaceutical composition. The applicator device includes a filter (30) that permits passage of fluid and inhibits passage of broken ampule shards. The applicator device includes a dispensing tip (20) through which the pharmaceutical composition passes.

20 Claims, 27 Drawing Sheets

(51) Int. Cl.
*A61K 47/10* (2017.01)
*A61K 47/18* (2017.01)
*A61K 47/38* (2006.01)
*A61K 47/44* (2017.01)

(52) U.S. Cl.
CPC .......... *A61K 47/186* (2013.01); *A61K 47/38* (2013.01); *A61K 47/44* (2013.01); *A61M 35/00* (2013.01); *A61M 2210/04* (2013.01)

(56) References Cited

U.S. PATENT DOCUMENTS

| | | | |
|---|---|---|---|
| 1,902,859 A * | 3/1933 | Rudolph | A46B 11/0027 401/175 |
| 3,393,962 A * | 7/1968 | Andrews | A45D 34/042 401/132 |
| 3,981,924 A | 9/1976 | Hall | |
| 4,143,050 A | 3/1979 | Rossy et al. | |
| 4,148,874 A | 4/1979 | Smith | |
| 4,157,967 A * | 6/1979 | Meyst | B29C 66/1312 D23/209 |
| 4,298,752 A | 11/1981 | Dauben et al. | |
| 4,299,006 A * | 11/1981 | Cruz | A46B 17/08 15/248.1 |
| 4,413,154 A | 11/1983 | Dessau | |
| 4,895,727 A | 1/1990 | Allen | |
| 5,230,579 A * | 7/1993 | Klawson | A45D 34/04 401/205 |
| 5,445,462 A * | 8/1995 | Johnson | A61M 35/006 401/133 |
| 5,464,855 A | 11/1995 | Capiris et al. | |
| 5,590,780 A | 1/1997 | O'Meara | |
| 5,702,694 A | 12/1997 | Chamness | |
| 5,727,892 A | 3/1998 | Baudin | |
| 6,066,124 A | 5/2000 | Caillouette | |
| D436,661 S | 1/2001 | Berry | |
| 6,379,342 B1 | 4/2002 | Levinson | |
| 6,547,467 B2 | 4/2003 | Quintero | |
| 6,673,031 B2 | 1/2004 | Mark | |
| 6,811,342 B2 | 11/2004 | Pauchet | |
| 8,518,076 B2 | 8/2013 | Stenton | |
| 8,871,801 B2 | 10/2014 | Levitt | |
| D771,250 S | 11/2016 | Zhang et al. | |
| D772,407 S | 11/2016 | Zhang et al. | |
| 9,480,691 B1 | 11/2016 | Roth | |
| D801,830 S | 11/2017 | Zhang et al. | |
| 10,195,635 B2 | 2/2019 | Sporrer | |
| D868,160 S | 11/2019 | Lam | |
| 10,745,413 B2 | 8/2020 | Davidson et al. | |
| D900,312 S | 10/2020 | Davidson et al. | |
| 11,052,064 B2 | 7/2021 | Davidson | |
| D933,494 S | 10/2021 | Tempfli et al. | |
| 11,147,790 B2 | 10/2021 | Welgus et al. | |
| 11,168,091 B2 | 11/2021 | Davidson et al. | |
| D938,587 S | 12/2021 | Fujii et al. | |
| D947,027 S | 3/2022 | Marik | |
| 11,279,165 B2 | 3/2022 | Skinner et al. | |
| D957,625 S | 7/2022 | Reynolds | |
| 11,559,294 B2 | 1/2023 | Pollack et al. | |
| D1,036,656 S | 7/2024 | Davidson et al. | |
| 2003/0068331 A1 | 4/2003 | Battaglia et al. | |
| 2003/0072814 A1 | 4/2003 | Maibach et al. | |
| 2004/0011830 A1 | 1/2004 | Kim | |
| 2004/0152766 A1 | 8/2004 | Au-Yeung et al. | |
| 2004/0162533 A1 | 8/2004 | Alley | |
| 2004/0242770 A1 | 12/2004 | Feldstein et al. | |
| 2004/0254561 A1 | 12/2004 | Stenton | |
| 2005/0019418 A1 | 1/2005 | Crutchfield et al. | |
| 2005/0111900 A1 | 5/2005 | Fazzolari et al. | |
| 2005/0169696 A1 | 8/2005 | Albisetti | |
| 2006/0110415 A1 | 5/2006 | Gupta | |
| 2006/0116649 A1 | 6/2006 | Hagele | |
| 2006/0180613 A1 | 8/2006 | Manesis | |
| 2007/0000566 A1 | 1/2007 | Gueret | |
| 2007/0111954 A1 | 5/2007 | Crutchfield et al. | |
| 2007/0187437 A1 | 8/2007 | Lord | |
| 2007/0233020 A1 | 10/2007 | Hearne | |
| 2007/0233021 A1 | 10/2007 | Poisson et al. | |
| 2007/0275045 A1 | 11/2007 | Evans et al. | |
| 2008/0146674 A1 | 6/2008 | Rosenberg et al. | |
| 2008/0195040 A1 * | 8/2008 | Clark | A61J 1/2093 604/87 |
| 2008/0246380 A1 | 10/2008 | Gwak | |
| 2009/0110645 A1 | 4/2009 | Morelli et al. | |
| 2009/0311028 A1 | 12/2009 | Odermatt et al. | |
| 2011/0086109 A1 * | 4/2011 | Dever | A61K 47/38 514/159 |
| 2011/0208136 A1 | 8/2011 | Sollingen et al. | |
| 2011/0212033 A1 | 9/2011 | Tamarkin et al. | |
| 2012/0016320 A1 | 1/2012 | Lin | |
| 2012/0077784 A1 | 3/2012 | Whitbourne | |
| 2012/0148520 A1 | 6/2012 | Strobel et al. | |
| 2012/0190658 A1 | 7/2012 | Studin | |
| 2012/0312709 A1 | 12/2012 | Kaufman | |
| 2013/0004230 A1 | 1/2013 | Kirk et al. | |
| 2013/0085137 A1 | 4/2013 | Grigorian et al. | |
| 2013/0197075 A1 | 8/2013 | Levitt | |
| 2014/0275248 A1 | 9/2014 | Johnson | |
| 2015/0118164 A1 | 4/2015 | Tamarkin et al. | |
| 2015/0328259 A1 * | 11/2015 | Shanler | A61M 35/003 604/290 |
| 2016/0193177 A1 | 7/2016 | Davidson | |
| 2017/0113004 A1 * | 4/2017 | Sams | A61M 5/007 |
| 2017/0305925 A1 | 10/2017 | Piotrowski et al. | |
| 2019/0002474 A1 | 1/2019 | Davidson et al. | |
| 2019/0031674 A1 | 1/2019 | Davidson et al. | |
| 2020/0155498 A1 | 5/2020 | Welgus et al. | |
| 2020/0270269 A1 | 8/2020 | Davidson et al. | |
| 2021/0070771 A1 | 3/2021 | Davidson et al. | |
| 2021/0386703 A1 | 12/2021 | Davidson | |
| 2021/0401793 A1 | 12/2021 | Welgus et al. | |
| 2024/0109911 A1 | 4/2024 | Davidson et al. | |

FOREIGN PATENT DOCUMENTS

| | | |
|---|---|---|
| CN | 1966508 A | 5/2007 |
| CN | 101012230 A | 8/2007 |
| CN | 101108853 A | 1/2008 |
| CN | 101108854 A | 1/2008 |
| CN | 101161654 A | 4/2008 |
| CN | 101453923 A | 6/2009 |
| CN | 101108853 B | 5/2010 |
| CN | 101798309 A | 8/2010 |
| CN | 101036774 B | 12/2010 |
| CN | 102146086 A | 8/2011 |
| CN | 102268006 A | 12/2011 |
| CN | 102268006 B | 12/2011 |
| CN | 102336765 A | 2/2012 |
| CN | 102526146 A | 7/2012 |
| CN | 202730045 A | 2/2013 |
| CN | 202902809 | 5/2013 |
| CN | 103923095 A | 7/2014 |
| CN | 204817029 U | 12/2015 |
| CN | 105636637 A | 6/2016 |
| CN | 106674248 A | 5/2017 |
| DE | 20016131 U1 | 11/2000 |
| EP | 0841059 A1 | 5/1998 |
| GB | 587994 A | 5/1947 |
| JP | S51-141863 A | 12/1976 |
| JP | H3-202002 A | 9/1991 |
| JP | 05-058914 | 3/1993 |

(56) References Cited

FOREIGN PATENT DOCUMENTS

| | | |
|---|---|---|
| JP | H05-255367 A | 10/1993 |
| JP | H07-500980 A | 2/1995 |
| JP | 10-114626 A | 5/1998 |
| JP | 11-319064 | 11/1999 |
| JP | 11-335303 | 12/1999 |
| JP | 2004-059446 A | 2/2004 |
| JP | 2005-187330 A | 7/2005 |
| JP | 2007-269693 | 10/2007 |
| JP | 2008-505960 A | 2/2008 |
| JP | 2010-516410 A | 5/2010 |
| JP | 2010-235471 A | 10/2010 |
| JP | 47-39621 B2 | 8/2011 |
| JP | 2001-245964 A | 9/2011 |
| JP | 2012-97152 A | 5/2012 |
| JP | 2013-507367 A | 3/2013 |
| JP | 2016-528015 A | 9/2016 |
| JP | 2017-513907 A | 6/2017 |
| KR | 10-2005-0032154 A | 4/2005 |
| KR | 100786203 B1 | 12/2007 |
| WO | WO 2008/092068 A2 | 7/2008 |
| WO | WO 2010/002476 A1 | 1/2010 |
| WO | WO 2010/079513 A2 | 7/2010 |
| WO | WO 2011/035019 A1 | 3/2011 |
| WO | WO 2012/131238 A1 | 10/2012 |
| WO | WO 2013/189841 A1 | 12/2013 |
| WO | WO-2015027111 A1 * 2/2015 ............... A61J 1/06 |
| WO | WO 2016/006693 A1 | 1/2016 |
| WO | WO 2016/100732 A2 | 6/2016 |
| WO | WO 2016/118633 A1 | 7/2016 |
| WO | WO 2018/226894 A1 | 12/2018 |

OTHER PUBLICATIONS

International Preliminary Report on Patentability, mailed Dec. 19, 2019, in connection with PCT/US2018/036353.

International Preliminary Report on Patentability, mailed Apr. 16, 2020, in connection with International Application No. PCT/US2018/054373.

[No Author Listed] CAS RN 27607-77-8. Entered STN: Nov. 16, 1984 28 pages.

[No Author Listed] CAS RN 76262-87-8. Entered STN: Nov. 16, 1984 19 pages.

[No Author Listed] CAS RN 89672-77-5. Entered STN: Nov. 16, 1984 29 pages.

Baker et al., Biotin; the structure of 2-alkyldihydrothiophene-3,4-dicarboxylic acids. J Org Chem. Jan. 1948;13(1):123-33. doi: 10.1021/jo01159a017.

Kronemyer et al., Verrica develops a solution for common warts. Retrieved from www.dermatologytimes.com. Nov. 13, 2017. 1 page.

Moed et al., Cantharidin revisited: a blistering defense of an ancient medicine. Arch Dermatol. Oct. 2001;137(10):1357-60. doi: 10.1001/archderm.137.10.1357.

Opposition to Israeli Patent Application No. 252907 by Wavelength Enterprises, Ltd., filed Mar. 1, 2021. 78 pages.

Sperry et al., Studies on the Diels-Alder reaction of annulated furans: application to the synthesis of substituted phenanthrenes. Tetrahedron Letters. Apr. 18, 2005;46(16):2789-93. Doi: 10.1016/j.tetlet.2005.02.148.

Torbeck et al., Cantharidin: a comprehensive review of the clinical literature. Dermatol Online J. Jun. 15, 2014;20(6):13030/qt45r512w0.

Verma et al., Bioactive component, cantharidin from Mylabris cichorii and its antitumor activity against Ehrlich ascites carcinoma. Cell Biol Toxicol. Jun. 2012;28(3):133-47. doi: 10.1007/s10565-011-9206-6. Epub Mar. 9, 2012.

Extended European Search Report, mailed Mar. 10, 2017, in connection with EP 14837297.2.

International Search Report and Written Opinion, mailed Nov. 20, 2014, in connection with PCT/US2014/052184.

Extended European Search Report, mailed Oct. 26, 2018, in connection with EP 15871116.8.

International Search Report and Written Opinion, mailed Jul. 14, 2016, in connection with PCT/US2015/066487.

International Preliminary Report on Patentability, mailed Jun. 29, 2017, in connection with PCT/US2015/066487.

Supplementary European Search Report, mailed Aug. 8, 2018, in connection with EP 16740681.8.

Extended European Search Report, mailed Dec. 4, 2018, in connection with EP 16740681.8.

International Preliminary Report on Patentability, mailed Aug. 3, 2017, in connection with PCT/US2016/014139.

International Search Report and Written Opinion, mailed Jul. 1, 2016, in connection with PCT/US2016/014139.

Invitation to Pay Additional Fees, mailed Aug. 27, 2018, in connection with PCT/US2018/O3653.

International Search Report and Written Opinion, mailed Oct. 22, 2018, in connection with PCT/US2018/036353.

Invitation to Pay Additional Fees, mailed Sep. 20, 2018, in connection with PCT/US2018/037808.

International Search Report and Written Opinion, mailed Nov. 13, 2018, in connection with PCT/US2018/037808.

International Preliminary Report on Patentability mailed Dec. 26, 2019 in connection with International Application No. PCT/US2018/037808.

Invitation to Pay Additional Fees, mailed Dec. 10, 2018, in connection with PCT/US2018/054373.

International Search Report and Written Opinion, mailed Apr. 3, 2019 in connection with PCT/US2018/054373.

[No Author Listed] Dormer Laboratories, "Cantharone and Cantharone Plus" sales brochure.

Aitken et al., Fragmentation patterns in the gas-phase pyrolysis of some bi- and tri-cyclic sulfolanes related to the 8-thiabicyclo[4.3.0]non-3-ene 8,8-dioxide ring system . J Chem Soc. Perkin Transactions 1. 1994;16:2301-2308.

Anderson et al., Practical Process Research and Development. 1st Edition. Academic Press. Mar. 20, 2000 81-111.

Aono et al., New method for generation of thiocarbonyl ylides from bis(trimethylsilylmethyl) sulfoxides and their application to cycloadditions. Heterocycles. 1995;40(1):249-60.

Augé et al., Catalysis by Lithium Cation: Lithium Trifluoromethanesulfonate as a Substitute for Lithium Perchlorate in Cycloadditions. Synlett 2000;6:877-9.

Bagatell, Studies on Biological Factors in Acantholysis. J Invest Dermatol. Nov. 1964;43:357-61.

Bouacha et al., A theoretical study of the mechanism, stereoselectivity and Lewis acid catalyst on the Diels-Alder cycloaddition between furan and activated alkenes. Tetrahedron Letters. 2013;54:4030-4033.

Braddock et al., Stereochemistry of the Catalysed Diels-Alder Reaction between Cyclopentadiene and Dimethyl Monothionofumarate; Soft versus Hard Lewis Acids. J. Chem. Soc. Chem. Commun. Jan. 1, 1993;16:1244-6. doi: https://doi.org/10.1039/C39930001244.

Brion et al., On the lewis acid catalyzed diels-alder reaction of furan. regio- and stereospecific synthesis of substituted cyclohexenols and cyclohexadienols. Tetrahedron Letters. 1982;23(50):5299-302. https://doi.org/10.1016/S0040-4039(00)85823-2.

Cacchi et al., Palladium-catalyzed carbonylation of enol triflates. A novel method for one-carbon homologation of ketones to α,β-unsaturated carboxylic acid derivatives. Tetrahedron Letters. 26(8), 1985, pp. 1109-1112.

Dang et al., Determination of trace cantharidin in plasma and pharmacokinetic study in beagle dogs using gas chromatography-mass spectrometry. J Anal Toxicol. Sep. 2009;33(7):384-8.

Dauben et al., Organic reactions at high pressure. Cycloadditions with furans. J. Am. Chem. Soc. 1976;98(7):1992-1993.

Dauben et al., Organic reactions at high pressure. The preparative scale synthesis of cantharidin. J. Org. Chem. 1985;50 (14):2576-2578.

Dauben et al., Simple, efficient total synthesis of cantharidin via a high-pressure Diels-Alder reaction. J. Am. Chem. Soc. 1980;102(22):6893-6894.

(56) References Cited

OTHER PUBLICATIONS

Grieco et al., Dramatic rate accelerations of Diels-Alder reactions in 5 M lithium perchlorate-diethyl ether: the cantharidin problem reexamined. J. Am. Chem. Soc. 1990;112(11):4595-4596.
Handy et al., Lithium Trifluoromethanesulfonimide in Acetone or Diethyl-ether as a Safe Alternative to Lithium Perchlorate in Diethyl-ether for Effecting Diels-alder Reactions. Unexpected Influence of the Counterion on Exo/endo Selectivity. Synlett 1995;5:565-567.
Hollis et al., Homogeneous catalysis. Titanium complex [Ti(Cp)$_2$(CF$_3$SO$_3$)2] and zirconium complex [Zr(Cp)$_2$(CF$_3$SO$_3$)$_2$THF], efficient catalysts for the Diels-Alder reaction. Organometallics. Aug. 1, 1992;11(8):2745-8. https://doi.org/10.1021/om00044a004.
Hollis et al., Homogenous Catalysis: Transition Metal Based Lewis Acid Catalysts. Tetrahedron. 1993;49(25):5415-30. doi: https://doi.org/10.1016/S0040-4020(01)87259-8.
Houk et al., On Lewis Acid catalysis of diels-alder reactions. J Am Chem Soc. Jun. 13, 1973;95(12):4094-4096.
Huang, Catalysts for Hetero Diels-Alder Reaction of Imines. Chinese Journal of Organic Chemistry. Oct. 2003;23(10):1064-75.
Hubbard et al., Lewis Acid Catalyzed Diels-Alder Reactions of Highly Hindered Dienophiles. J. Org. Chem. 1998;63(12):4143-4146.
Hunt et al., Why do catalytic quantities of lewis acid generally yield more product than 1.1 equiv in the intramolecular diels-adler reaction with a furan diene? Competitive complexation NMR studies provide an answer. J Am Chem Soc. 1995;117:1049-1056.
Kharitonov et al., Synthetic transformations of higher terpenoids: VIII. [4+2]-Cycloaddition reactions of lambertianic acid. Russian J Organic Chem. 2003;39(1):57-74.
Lange et al., Synthesis of 4-carboxy-2-thiabicyclo [3.2.0] Heptan-6-ones via 3-carboxy-2,3-dihydrothiophenes: potential β-lactamase inhibitors. Tetrahedron Lett. 1985;26(15):1791-1794.
Magyarosy et al., Cycloaddition approach to the curing of polyimides via precursor containing thiophene-S,S-dioxide. Hetero Chem. 2006;17(7):648-652.
Mehdinia et al., Analysis of cantharidin in false blister beetles (Coleoptera: Oedemeridae) by headspace solid-phase microextraction and gas chromatography-mass spectrometry. J Chromatogr B Analyt Technol Biomed Life Sci. Oct. 1, 2011;879(27):2897-901. doi:10.1016/j.jchromb.2011.08.020. Epub Aug. 22, 2011.
Nikbakhtzadeh et al., Origin, transfer and distribution of cantharidin-related compounds in the blister beetle Hycleus scabiosae. J Venom Animals Toxins. 2012; 18(1):88-96.
Pagni et al., A chemical, spectroscopic, and theoretical assessment of the lewis acidity of LiClO4 in Diethyl Ether. J. Org Chem. 1993;58:3130-3133.
Prabhakar Reddy et al., Synthesis, cytotoxic activity and structure-activity relationships of hedychenone analogues. Bioorg Med Chem Lett. Apr. 15, 2010;20(8):2525-8. doi: 10.1016/j.bmcl.2010.02.101. Epub Mar. 3, 2010.
Rosenberg et al., Cantharidin treatment of warts at home. Arch Dermatol. Aug. 1977;113(8):1134.
Rudo et al., Cantharidin—als Potenzmittel entzaubert, aber Oct. 1, 2013. Chemie in Unserer Zeit. vol. 47, Issue 5. pp. 310-316. With Supporting Information.

Schenck et al., Ausfuhrliche Mitteilung erfolgt an anderer Stelle. Naturwissenshaften Oct. 15, 1953; 40: 581.
Song et al., Ionic liquids as powerful media in scandium triflate catalysed Diels-Alder reactions: significant rate acceleration, selectivity improvement and easy recycling of catalyst. Chem Commun. 2001;12:1122-3.
Stork et al., A Stereospecific Synthesis of Cantharidin. J. Am. Chem. Soc., 1953;75(2):384-392.
Stork et al., Cantharidin. A Stereospecific Total Synthesis. J. Am. Chem. Soc. 1951;73(9):4501-4501.
Terao et al., Thiocarbonyl Ylides. VI. New Generation of Thiocarbonyl Ylides from Organosilicon Compounds Containing Sulfur and Their 1, 3-Cycloadditions. J-STAGE. 1987;35(5):1734-1740.
Tseng et al., Synthesis and Evaluation of Cantharidinimides on Human Cancer Cells. J Exp Clin Med. Oct. 2012;4(5):280-283.
White et al., Dihydrothiophenes as precursors to fused quinolines, quinolones and coumarins via o-quinodimethane intermediates. Tetrahedron 52(9), Feb. 26, 1996, pp. 3117-3134.
International Preliminary Report on Patentability, mailed Mar. 3, 2016, in connection with PCT/US2014/052184.
Partial Supplementary European Search Report for Application No. EP 18864069.2, mailed Apr. 12, 2021.
Extended European Search Report for Application No. EP 18864069.2, mailed Jul. 7, 2021.
Chung et al., Sequential Nitromethane Conjugate Addition/Elimination—PD-Catlayzed Allylation of beta-Trifloxy Acrylates. Application to Carbapenem Synthesis. Org Lett. 1999;1(11):1783-1785.
Earle et al., Diels-Alder reactions in ionic liquids . A safe recyclable alternative to lithium perchlorate-diethyl ether mixtures. Green Chem. Feb. 1999;1:23-25. doi: 10.1039/A808052F.
Gaul, Part I. Diels-Alder reactions performed in highly polar media. Part II. Reactions of allenylstannanes with in situ generated immonium ions. Dissertation. Indiana University, Bloomington Indiana, 1990. 152 pages.
Harreus et al., 2-Pyrrolidone. Ullmann's Encyclopedia of Industrial Chemistry. 2000. doi: doi: 10.1002/14356007.a22_457.pub2.
Rossy et al., Aromatization of Dihydrothiophenes. Thiophenesaccharin: A Sweet Surprise. J Org Chem. 1980;45:617-620.
White et al., Quinoline Analogues of Ortho-Quinodimethane. Tetrahedron Lett. 1995;36(33):5983-5986.
[No Author Listed] Journal of Organic Chemistry Author Guidelines. Last updated May 5, 2022. 3 pages.
Chen et al., Precautions with gentian violet: skin marking made sterile, effective, and economical. Am J Infect Control. Apr. 2009;37(3):244-6. doi: 10.1016/j.ajic.2008.06.005. Epub Oct. 14, 2008.
Pulce et al., Denatonium Benzoate. Human Toxicol. Jan. 1996; 1-12. Accessed Sep. 12, 2022 from <https://www.sciencedirect.com/topics/medicine-and-dentistry/denatonium-benzoate>.
Extended European Search Report, mailed Apr. 11, 2024 for European Application No. 24153182.1.
Becerro De Bengoa Vallejo et al., Application of cantharidin and podophyllotoxin for the treatment of plantar warts. J Am Podiatr Med Assoc. Nov.-Dec. 2008;98(6):445-50. doi: 10.7547/0980445.

\* cited by examiner

DEVICES AND METHODS FOR THE TREATMENT OF BODY SURFACE DISORDERS

RELATED APPLICATIONS

This application is a national stage filing under 35 U.S.C. § 371 of international PCT application, PCT/US2018/037808, filed Jun. 15, 2018, which claims the benefit under 35 U.S.C. § 119(e) to U.S. Provisional Application, U.S. Ser. No. 62/520,504, filed on Jun. 15, 2017, and entitled "Devices and Methods for the Treatment of Cutaneous Disorders," and claims the benefit under 35 U.S.C. § 119(e) to U.S. Provisional Application, U.S. Ser. No. 62/615,429, filed on Jan. 9, 2018, and entitled "Devices and Methods for the Treatment of Cutaneous Disorders," which are each incorporated herein by reference in their entireties.

BACKGROUND

The body surfaces of the body can be affected by various disorders. For example, many cutaneous disorders produce lesions on the skin. Some of these lesions take the form of epidermal growths on the skin. For instance, warts are small epidermal skin growths caused by viral infections, often found on the hands or feet. The most common type of wart is called Verruca vulgaris, which can be caused by multiple different strains of the human papilloma virus (HPV). On most parts of the body these warts may be referred to as common warts; on the feet, however, they may be referred to as plantar warts; when on the genitals they may be referred to as genital warts or condoloma. Other epidermal viral conditions such as Molluscum contagiosum resemble warts but are caused by distinct viruses. These viral mediated skin growths may be unsightly and may pose a significant risk for cancerous transformation and for spreading, making their removal desirable. Other superficial hyperproliferative disorders resemble warts but are caused by non-viral mechanisms and include seborrheic keratosis, actinic keratosis, and porokeratosis.

Multiple modalities have been used to remove warts, Molluscum contagiosum, and other cutaneous diseases, including cryotherapy; surgical curettage; laser treatment; irritants such as salicylic acid and zinc oxide; acids such as nitric acid and squaric acid, immunotherapeutics such as imiquimod, 2,4-dinitrochlorobenzene and *Candida* antigen, and chemotherapeutics such as bleomyocin, podophyllotoxin and 5-fluorouracil. Many of these therapies can be painful, while others can leave disfiguring scars and/or require daily application. Perhaps most troubling, however, is that many of these cutaneous disorders remain recalcitrant even after multiple follow-up treatments. Accordingly, improved therapies are needed for treating these conditions.

SUMMARY

Described herein is an applicator device for dispensing a composition for topical administration of the composition to a subject. In some embodiments, the composition may be a pharmaceutical composition. In some embodiments, the applicator device may be used to topically administer a composition to a subject. The applicator device may topically administer the composition to various body surfaces, including, but not limited to, skin, mucous membranes, exposed soft tissue or internal organs, genitalia, penis, vagina, anus, nails, hair, nose, eye, ear, or mouth, including lips, teeth, tongue, and gums. These body surfaces may be intact, abraded or wounded or exposed due to injury or surgical exposure.

Devices, methods, kits, and systems of treating one or more conditions, such as a body surface condition, are described herein. A body surface condition is a condition affecting a portion of the body that can be treated via topical administration of a composition onto the body. According to one aspect, an applicator device is used to dispense a composition onto an area of the body affected by a condition. The applicator device may be constructed and arranged to deliver a controllable amount of the composition to a specific location of the body without getting the composition on other areas of the body.

According to one aspect, the applicator device is able to produce droplets that can be dispensed onto a body surface without making physical contact between the applicator device and the body surface. As a result, when administering the composition, the user can avoid contacting the body surface with the applicator device (e.g., to avoid physically disturbing the body surface and/or to avoid contaminating the dispenser tip or the pharmaceutical composition) and holds the dispenser tip at a small distance from the desired treatment site when administering the pharmaceutical composition, allowing the pharmaceutical composition to be dispensed onto the body surface. This is in contrast to an applicator device having a brush applicator (foam, cloth, or fuzzy) or roll-on head that must contact body surface in order to administer the composition. Another aspect of this dispenser tip is that it may minimize the surface area and time of exposure of the solution to the air, reducing the amount of solvent loss and thereby maintaining the concentration of the solution that is applied to the body surface compared to other applicator tips.

Another aspect of the present disclosure provides an applicator device for dispensing a pharmaceutical composition to topically treat a condition. The applicator device may comprise: a tube, an ampule positioned within the tube, a pharmaceutical composition contained within the ampule, a dispenser tip attached to the tube, the dispenser tip having a tapered tip, and a filter positioned within the tapered tip of the dispenser tip. The filter may be constructed and arranged to permit passage of fluid and inhibit passage of broken ampule shards having a particle size of at least 150 µm.

Another aspect of the present disclosure provides an applicator device for dispensing a pharmaceutical composition to topically treat a condition. The applicator device may comprise: a tube, a pharmaceutical composition contained within the tube, a dispenser tip coupled to the tube, and a cap having an opening for receiving the dispenser tip. The cap may have a closed position in which at least a portion of the dispenser tip is passed through the opening. The cap may be coupled to the dispenser tip and positioned over at least a portion of the dispenser tip. When the cap is in the closed position, venting of the dispenser tip is permitted through the opening of the cap. In some embodiments, the applicator device includes an ampule, and the pharmaceutical composition is contained within the ampule.

Another aspect of the present disclosure provides a method of topical administration of a pharmaceutical composition to a subject. The method may comprise: squeezing the tube of an applicator device to break an ampule within the tube to release a pharmaceutical composition contained within the ampule while the cap is in a closed position covering at least a portion of a dispenser tip of the applicator device, moving the dispenser tip toward a subject, and dispensing the pharmaceutical composition from the dispenser tip onto the subject.

Another aspect of the present disclosure provides a kit for dispensing a pharmaceutical composition for topically treating a condition. The kit may include a plurality of applicator devices. Each applicator device may comprise: a tube, an ampule positioned within the tube, a pharmaceutical composition contained within the ampule, a dispenser tip attached to the tube, the dispenser tip having a tapered tip, and a filter positioned within the tapered tip of the dispenser tip, the filter being constructed and arranged to permit passage of fluid and inhibit passage of broken ampule shards having a particle size of at least 150 µm. The kit may also include instructions for use. In some embodiments, the kit may include external packaging to protect the applicator and/or drug from light or moisture, aids for opening the applicator and/or promotional materials. The pharmaceutical composition may comprise cantharidin, acetone, ethanol, a plasticizer, and a film-forming agent.

Another aspect of the present disclosure provides methods of treating a subject having an affected body surface area, such as, but not limited to, skin, eye, ear, mouth, nose, vagina, or anus. The method can comprise squeezing the tube of an applicator device to break an ampule within the tube to release a pharmaceutical composition contained within the ampule while the cap is in a closed position covering at least a portion of a dispenser tip of the applicator device. The method can also comprise moving the dispenser tip toward an affected body surface area of a subject and dispensing the pharmaceutical composition from the dispenser tip onto the affected body surface area.

According to one aspect, patients may receive one treatment every 3 weeks, plus or minus 4 days (i.e. one treatment every 17 to 25 days): a first treatment at week 0, a second treatment at week 3, a third treatment at week 6, and a fourth treatment at week 9.

One aspect of the present disclosure provides a method of treating a dermatological condition. The method can comprise applying a pharmaceutical composition to a subject, which may include: squeezing a tube of an applicator device to break an ampule within the tube to release a pharmaceutical composition contained within the ampule and dispensing the pharmaceutical composition from the dispenser tip onto a plurality of skin lesions on a subject. The method can include performing the step of applying the pharmaceutical composition four times, once every 17 to 25 days, where the pharmaceutical composition comprises cantharidin, acetone, ethanol, a plasticizer, and a film-forming agent.

Another aspect of the present disclosure provides a method of treating a dermatological condition. The method may include treating a plurality of skin lesions on a subject by dispensing a pharmaceutical composition out of an applicator device onto the skin lesions, where the pharmaceutical composition comprises cantharidin and one or more excipients, and where treating the skin lesions with the applicator device clears more of the skin lesions than treating of the skin lesion with a stick applicator in the same amount of time.

Another aspect of the present disclosure provides a method of treating a dermatological condition. The method may include treating a plurality of skin lesions on a subject by dispensing a pharmaceutical composition out of an applicator device onto the skin lesions. The pharmaceutical composition may comprise cantharidin and one or more excipients. Treating the skin lesions with the applicator device may clear more of the skin lesions than treating of the skin lesion with a stick applicator in the same amount of time.

Another aspect of the present disclosure provides an applicator device for dispensing a pharmaceutical composition for topical administration of the pharmaceutical composition to a subject. The device may include a tube, a pharmaceutical composition contained within the tube, and a dispenser tip attached to the tube. The dispenser tip may have a tapered tip that ends in a distal opening having an internal diameter of less than about 0.013 inches and external diameter of less than about 0.034 inches.

Another aspect of the present disclosure provides a method of treating a dermatological condition. The method may include applying a pharmaceutical composition to a subject, which may include squeezing a tube of an applicator device. The applicator device may have a dispenser tip having a tapered tip that in a distal opening having an internal diameter of less than about 0.013 inches and external diameter of less than about 0.034 inches. The method may also include dispensing the pharmaceutical composition from the dispenser tip onto a plurality of skin lesions on a subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
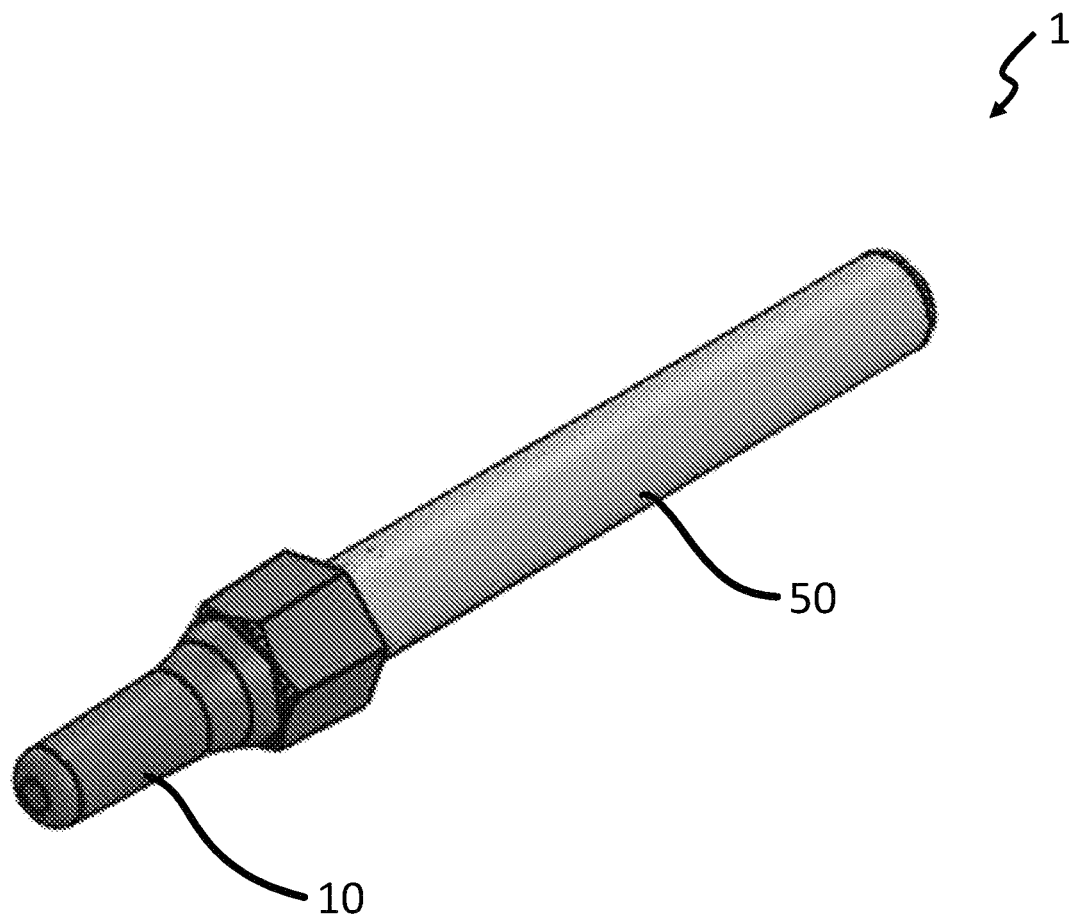
FIG. 1 is a perspective view of an applicator device according to some aspects of the invention.
Figure 2:
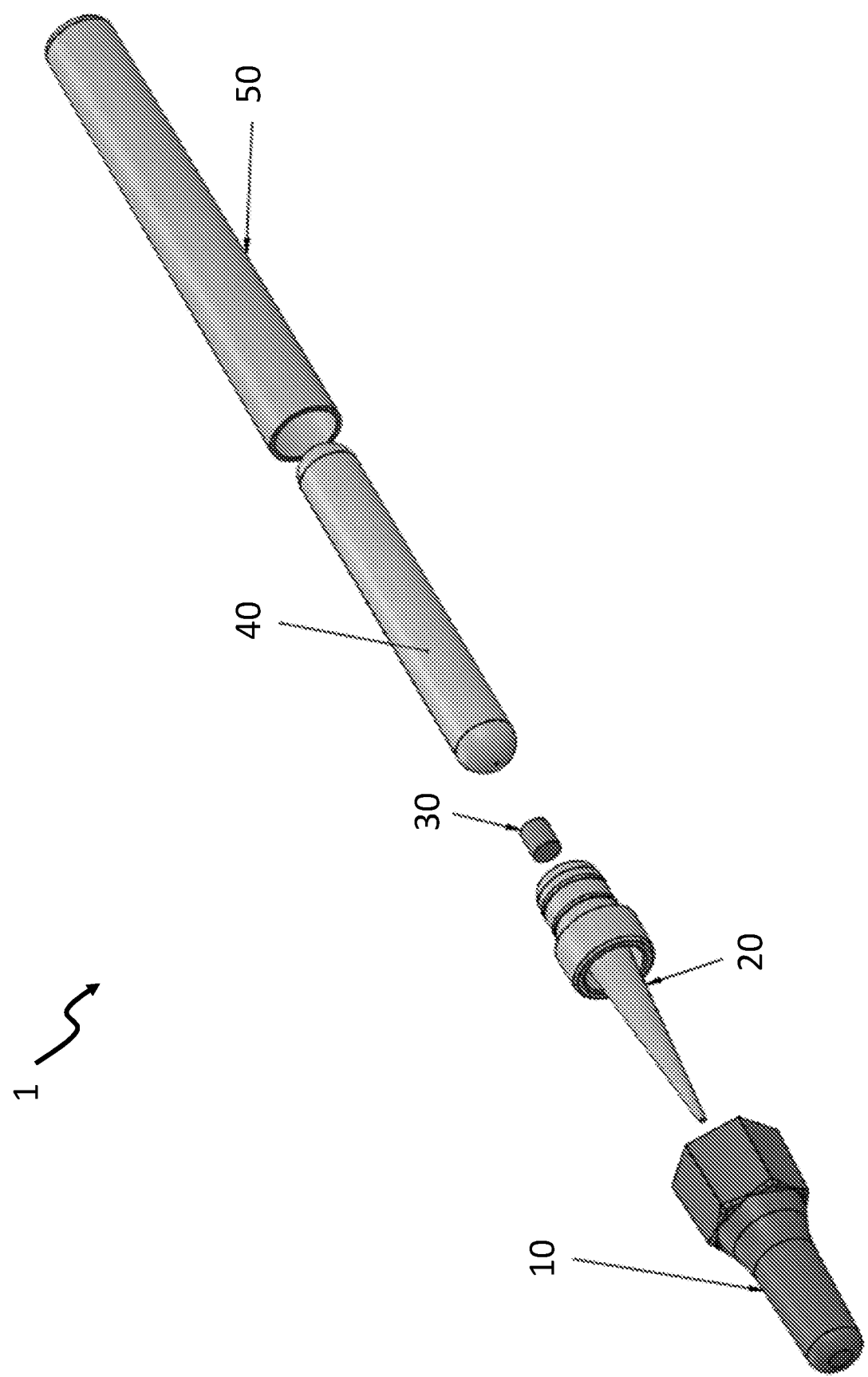
FIG. 2 is an exploded view of the applicator device of FIG. 1.
Figure 3:
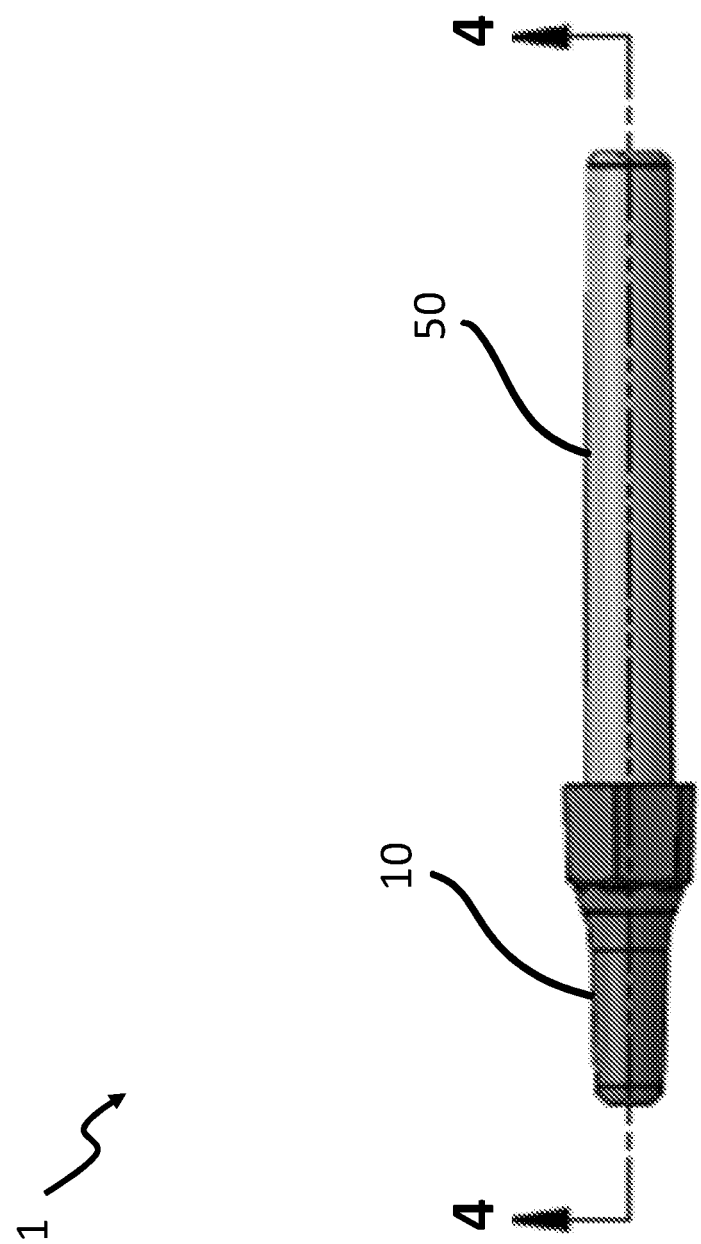
FIG. 3 is a side view of the applicator device of FIG. 1.
Figure 4:
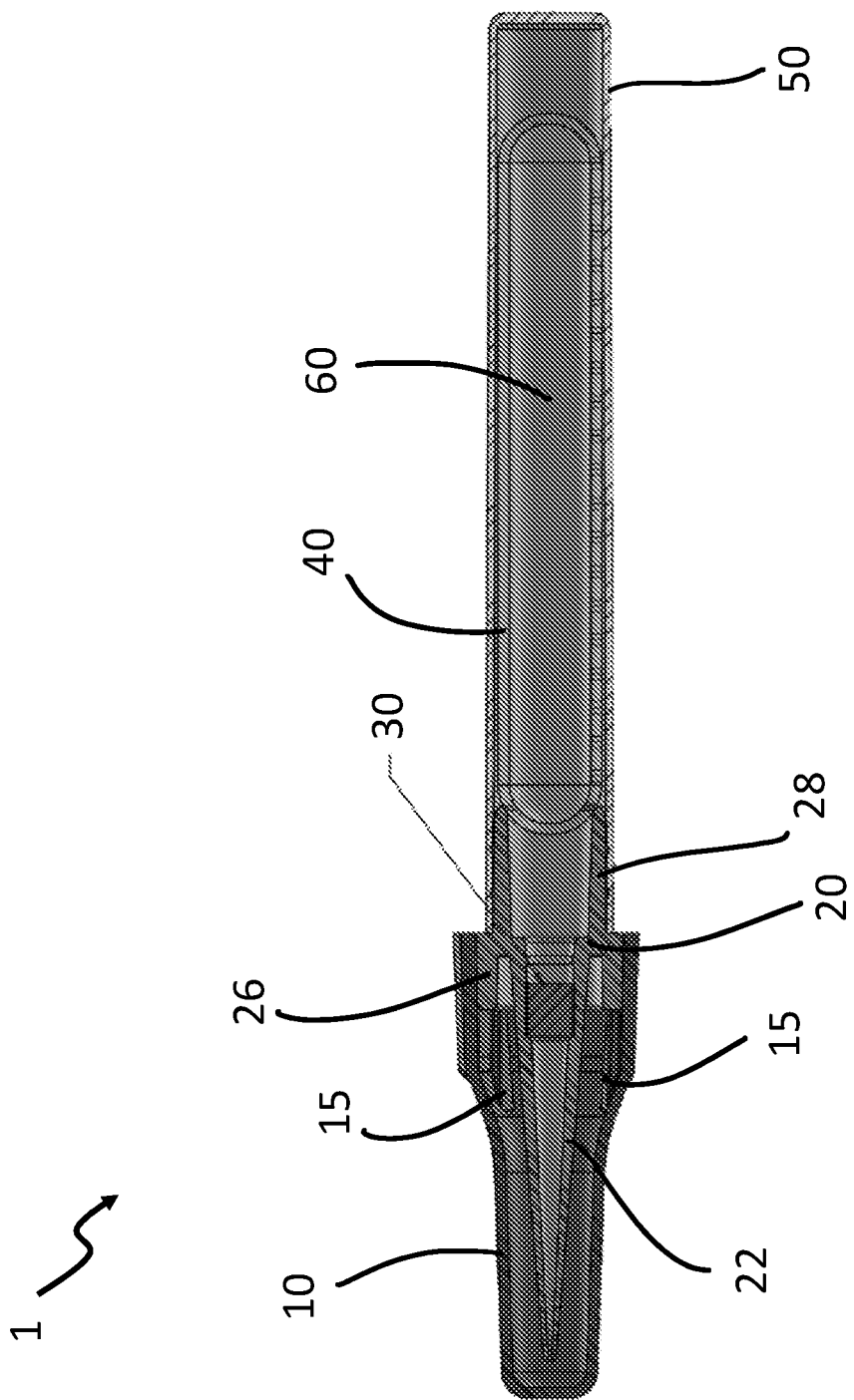
FIG. 4 is a cross-sectional view of the applicator device of FIG. 3 taken along line 4-4 of FIG. 3.

In one set of embodiments, an applicator device used to dispense a composition is provided. The applicator device may be used to topically administer the composition to a body surface of a subject. FIG. 1 depicts an illustrative embodiment of an applicator device 1 having a tube 50 and a cap 10. FIG. 2 depicts an exploded view of the applicator device 1. In some embodiments, the applicator device 1 includes a reservoir 40 (e.g., an ampule) for holding a pharmaceutical composition. In some embodiments, the applicator device 1 includes a dispenser tip 20 and a filter 30. FIG. 3 depicts a side view of the applicator device 1, and FIG. 4 is a cross-sectional view of the applicator device of FIG. 3 taken along line 4-4 of FIG. 3. In some embodiments, the applicator device may be used to deliver any suitable composition for topical administration of the composition to a body surface.

The relative position of each of the components of the applicator device 1 according to some embodiments can be seen in FIG. 4. In some embodiments, the ampule 40 is positioned within the tube 50. In some embodiments, the filter 30 is positioned within the dispenser tip 20. In some embodiments, the cap 10 has a closed position in which the cap 10 covers the distal opening of the dispenser tip. In some embodiments, in the closed position, the cap is removably coupled to the dispenser tip 20.

In some embodiments, the pharmaceutical composition is stored within the ampule 40. The ampule 40 may be constructed and arranged to be a sealed vessel to prevent exposure of the pharmaceutical composition, in particular the active ingredient, to ambient air, which may aid in preserving the stability of the pharmaceutical composition and/or active ingredient. In some embodiments, the ampule is made of glass. In some embodiments, the ampule is made of plastic.

According to some embodiments, in use, a user may initiate release of pharmaceutical composition by squeezing the tube 50, which causes the ampule 40 to break, resulting in release of pharmaceutical composition from inside the ampule. In some embodiment, a user squeezes the tube to break the ampule by squeezing a paperboard or cardboard sleeve or other ampule crushing device around the tube. With the composition released from the ampule, the pharmaceutical composition may flow from the broken ampule toward the dispenser tip 20. In some embodiments, squeezing of the tube may cause the composition to flow out of the dispenser tip 20. The filter 30 may be constructed and arranged to permit passage of the pharmaceutical composition, while inhibiting passage of shards from the broken ampule.

In some embodiments, a user may keep the cap 10 in the closed position when initiating release of the pharmaceutical composition (e.g., when squeezing the tube 50 to break the ampule 40). In some embodiments, keeping the cap 10 on while the ampule is being broken may help to avoid premature dispensing of the pharmaceutical composition out of the dispenser tip. In other embodiments, however, a user may initiate release of the pharmaceutical composition with the cap 10 off. In some embodiments, the unit can be facing up, down or at an angle when the ampule is broken.

In some embodiments, when the user (e.g., healthcare professional) is ready to administer the pharmaceutical composition to a subject, the user removes the cap 10, exposing the distal opening of the dispenser tip 20. The user then moves the dispenser tip 20 toward the desired treatment sites on the body surface of the subject. In some embodiments, the dispenser tip is constructed and arranged such that the user must exert a threshold amount of force on the tube (e.g., squeeze the tube) to create a sufficient amount of pressure inside the tube to cause an amount of the pharmaceutical composition to be released out of the dispenser tip. In some embodiments, air may be expelled prior to the pharmaceutical composition resulting in the creation of an internal vacuum. In some embodiments, gravity alone is sufficient to cause the pharmaceutical composition to flow out of the dispenser tip and onto the body surface of the subject.

In some embodiments, cessation of the applied force on the tube (e.g., user stops squeezing the tube), may cause the pharmaceutical composition to be drawn back into the dispenser tip. In some embodiments, this movement of the pharmaceutical composition back into the dispenser tip may be caused by creation of vacuum inside the tube 50 that occurs due to expansion of the internal volume of the tube 50 from a first volume when in a squeezed state to a larger volume when the squeezing ceases, and the tube is permitted to revert back to its original unstressed shape. In some embodiments, this movement of the pharmaceutical composition back into the dispenser tip may be caused or facilitated by the geometry of dispenser tip, which will be discussed in a later section.

In some embodiments, the applicator device is able to produce droplets that can be dispensed onto the body surface without making physical contact between the applicator device and the body surface.

In other embodiments, however, the user may contact the body surface with the distal end of the dispenser tip during administration of the pharmaceutical composition.

In some embodiments, a user dispenses an amount of the pharmaceutical composition from the applicator device onto an intermediate applicator, such as a cotton swab stick applicator, a stick, a toothpick, a capillary tube, a cotton ball, or any other suitable applicator, which is then used to apply the pharmaceutical composition to a treatment site.

In some embodiments, the applicator device may have a dispenser tip. In some embodiments, the dispenser tip is a separate component from the tube. In some embodiments, the dispenser tip is integrally formed with the tube, such that the dispenser tip and tube form one monolithic component. In some embodiments, the dispenser tip includes a tapered tip through which a pharmaceutical composition flows. The dispenser tip may have a distal opening through which the pharmaceutical composition exits the applicator device.

Figure 5:
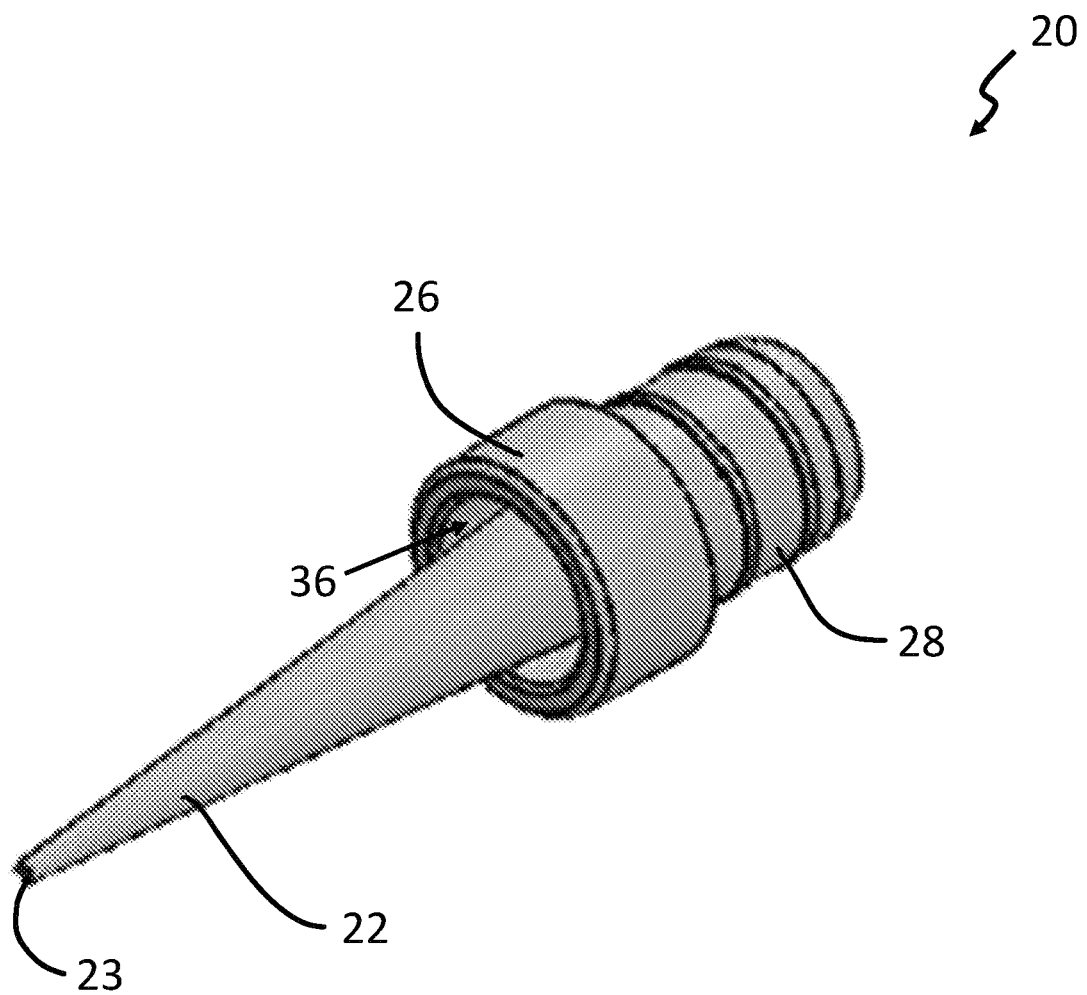
FIG. 5 is a perspective view of a dispenser tip of an applicator device according to some aspects of the invention.

One illustrative embodiment of a dispenser tip is shown in FIG. 5. The dispenser tip 20 may include a tapered tip 22, which may include an opening 23. In some embodiments, the opening 23 is at the distal end of the tapered tip 22.

FIGS. 6-9 provide dimensions (shown in inches for distances and degrees for angles) for one illustrative embodiment of a dispenser tip. It should be understood that such dimensions are provided as an illustrative example, and that the applicator device may include a dispenser tip having different dimensions than those shown in FIGS. 6-9.

In some embodiments, the opening 23 has an outer diameter of about 0.01 inches to about 0.1 inch, about 0.015 inches to about 0.09 inches, about 0.0175 inches to about 0.05 inches, about 0.02 inches to about 0.04 inches, about 0.025 inches to about 0.035 inches, about 0.028 inches to about 0.032 inches, or about 0.032 inches. In some embodiments, the opening 23 has an inner diameter of about 0.001 inches to about 0.1 inches, about 0.005 to about 0.05 inches, about 0.0075 to about 0.05 inches, about 0.01 inches to about 0.03 inches, or about 0.012 inches.

According to one aspect of the invention, in some embodiments, the dispenser tip includes a tapered tip, which may have an outer surface and an inner surface. The pharmaceutical composition from the applicator device flows through and may contact the inner surface of the dispenser tip. The inner and/or outer surfaces may be tapered (i.e., decrease in size), in the direction moving from a proximal end to a distal end of the dispenser tip. In some embodiments, the angle of the taper of the outer surface may be different than the angle of the taper of the inner surface. In some embodiments, the taper angle of the outer surface changes across the length of the tapered tip. In some embodiments, the taper angle of the inner surface changes across the length of the tapered tip. In some embodiments, a first portion of the outer surface of the tapered tip may have a first taper angle, and a second portion of the outer surface may have a second, different taper angle. In some embodiments, a first portion of the inner surface of the tapered tip may have a first taper angle, and a second portion of the inner surface may have a second, different taper angle. In some embodiments, the second taper angle is smaller than the first taper angle. In some embodiments, the inner and/or the outer surfaces may have a portion that is tapered and a portion that is not tapered.

Figure 7:
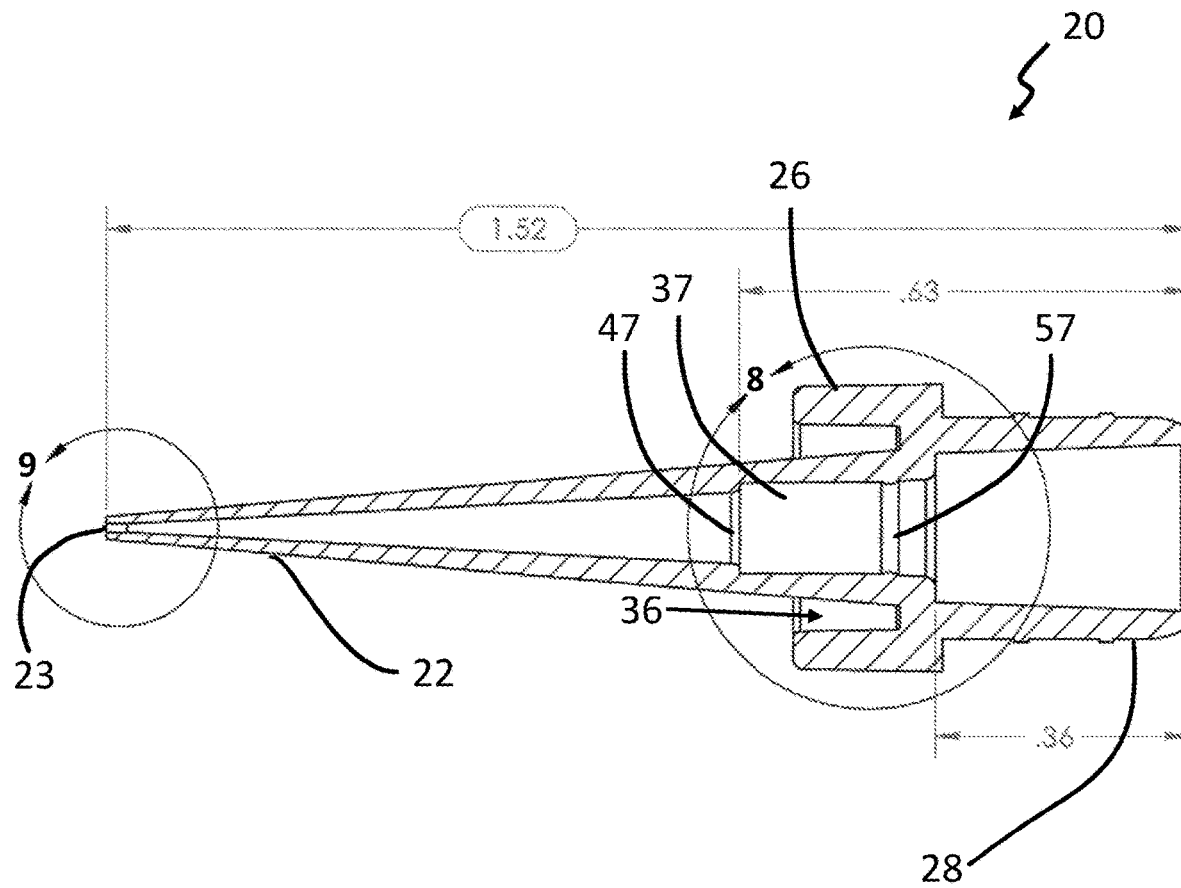
FIG. 7 is a cross-sectional view of the dispenser tip of FIG. 6 taken along line 7-7 of FIG. 6.
Figure 9:
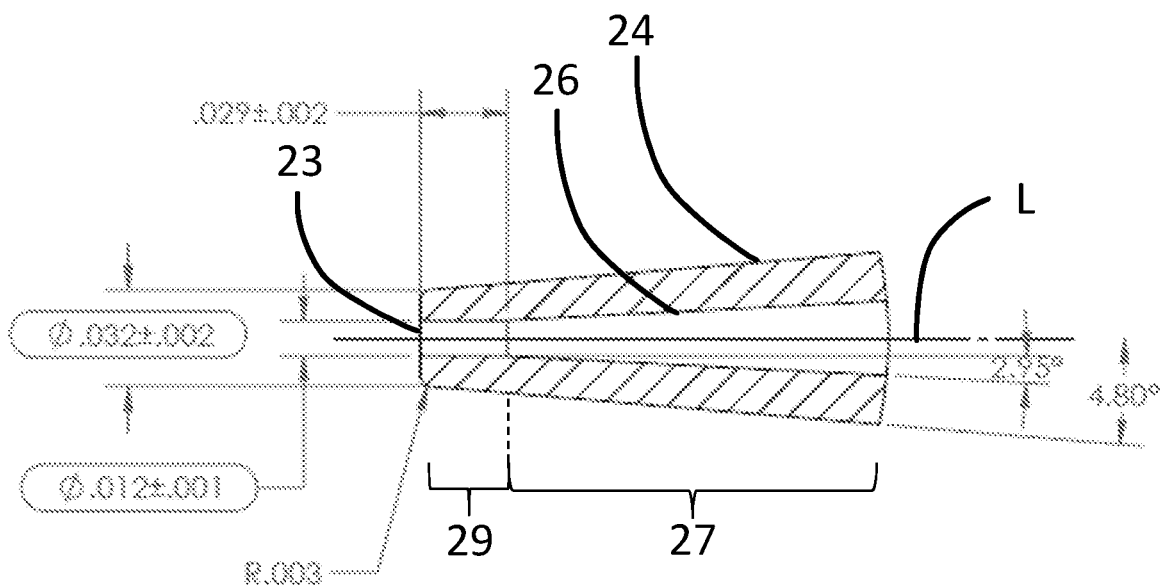
FIG. 9 is a detail view of the encircled region 9 of the dispenser tip of FIG. 7.

In one illustrative embodiment, shown in FIG. 9, which depicts a detail view of the encircled region 9 of the dispenser tip of FIG. 7, the tapered tip 22 has an outer surface 24 and an inner surface 26. The inner surface 26 has a first portion 27 that is tapered, and a second portion 29 that is straight, or has a taper angle that is different than that of the first portion. In some embodiments, the second portion may have a taper angle that is smaller than that of the first portion. As also seen in the embodiment of FIG. 9, the taper angle of the outer surface 24 is different than that of the taper angle of the first portion 27 of the inner surface 26.

In some embodiments, the inner surface of the dispenser tip has a taper angle of about 1 to about 5 degrees, about 2 to about 4 degrees, about 2.5 to about 3.5 degrees, about 2.5 to about 4 degrees, about 2.5 to about 4.5 degrees, about 2.5 to about 5 degrees, about 2.5 to about 5.5 degrees, or about 3.00 degrees.

In some embodiments, the outer surface of the dispenser tip has a taper angle of about 1 to about 10 degrees, about 2 to about 9 degrees, about 2.5 to about 5.5 degrees, about 2.5 to about 7 degrees, about 3 to about 8 degrees, about 4 to about 7 degrees, about 4.5 to about 5.5 degrees, about 4.7 degrees to about 5 degrees, or about 4.80 degrees.

Figure 6:
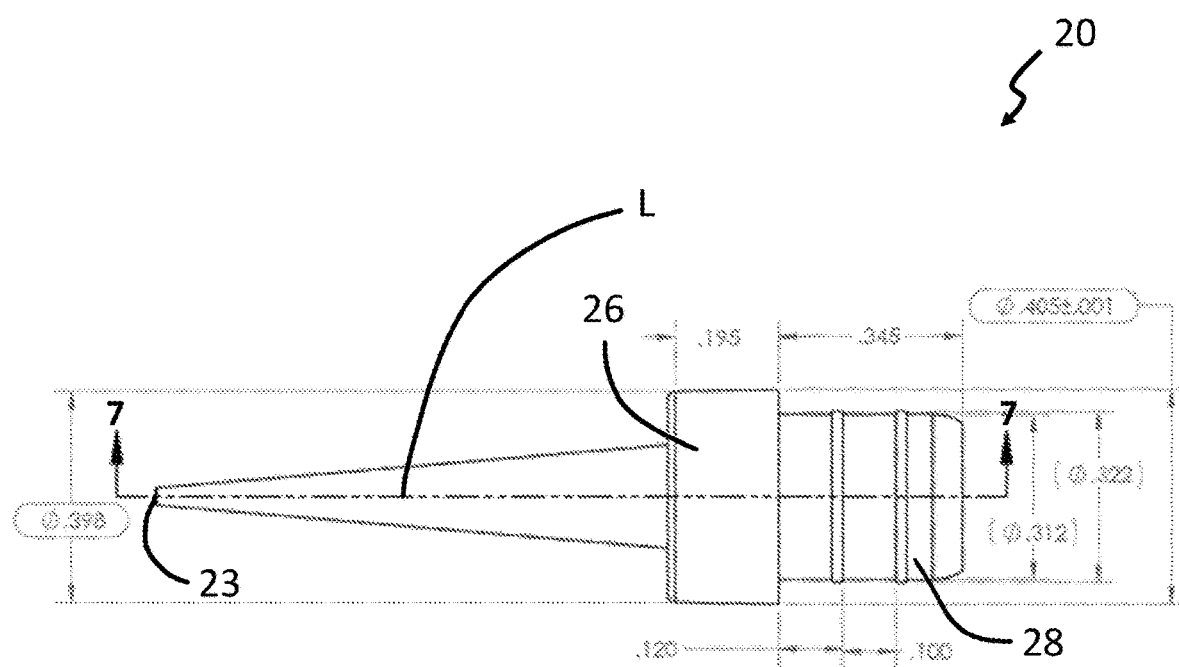
FIG. 6 is a side view of a dispenser tip of an applicator device as described herein.
Figure 8:
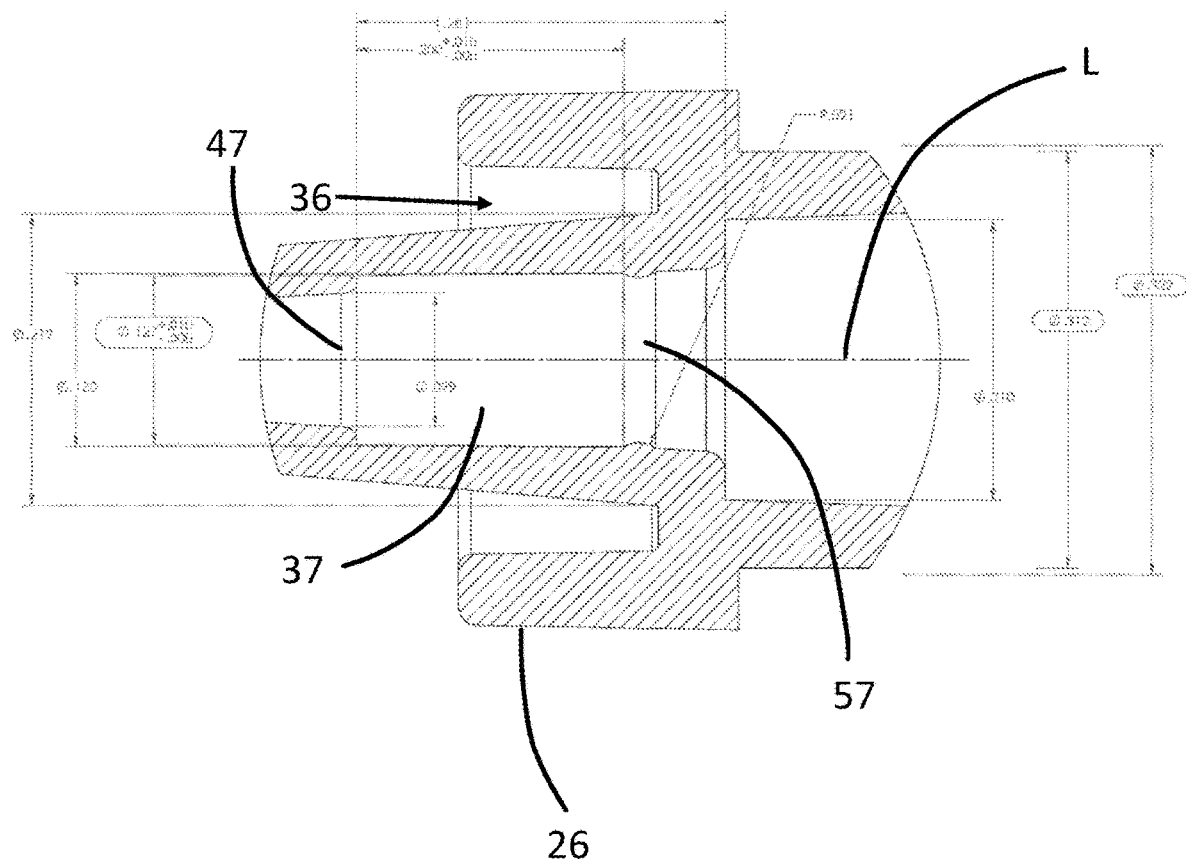
FIG. 8 is a detail view of the encircled region 8 of the dispenser tip of FIG. 7.

The tapered tip may have a longitudinal axis L, as shown in FIGS. 6, 8 and 9. The tapered tip may be rotationally symmetric about the longitudinal axis L.

The tapered tip may have a length along longitudinal axis L of about 0.1 to about 2 inches, about 0.3 to about 1.7 inches, about 0.5 inches to about 1.5 inches, about 0.7 inches to about 1.4 inches, about 0.8 inches to about 1.3 inches, about 0.9 inches to about 1.3 inches, about 1.1 to about 1.3 inches, or about 1.1 inches to about 1.2 inches.

In some embodiments, the inner surface of the dispenser tip at a distal portion of the tip has a decreased taper as compared to the rest of the inner surface, or is a straight-walled channel with no taper. In some embodiments, the distal portion of the tip having a straight-walled inner channel spans a distance along the longitudinal axis L of the dispenser tip that is about 0.01 to about 0.1 inch long, about 0.01 to about 0.05 inches long, about 0.02 to about 0.04 inches long, about 0.025 to about 0.035 inches long, or about 0.029 inches long.

According to one aspect of the invention, the size and shape of the tapered tip may help to control dispense of droplets of the composition onto desired areas of skin. In some embodiments, the tapered tip produces droplets of the composition having a size of about 0.1 mm to about 10 mm, about 0.5 mm to about 9 mm, about 0.7 mm to about 6 mm, or about 1 mm to about 4 mm in size. The controlled size of the droplet produced by the applicator tip may help to keep dispensed composition within a small area of skin and avoid dispensing of composition on unwanted areas of skin, e.g., limiting treatment only to areas of skin that are affected by a skin condition.

In some embodiments, the volume of each droplet of the composition administered by the applicator device may be at least 1 uL, at least 2 uL, at least 3 uL, at least 4 uL, at least 5 uL, at least 6 uL, at least 7 uL, at least 8 uL, at least 9 uL, at least 10 uL, at least 15 uL, at least 20 uL, at least 30 uL, at least 50 uL, at least 100 uL, at least 200 uL, at least 300 uL, at least 500 uL, at least 800 uL, at least 900 uL, at least 1 mL, or at least 5 mL. In some embodiments, the volume of each droplet administered by the applicator device may be less than 5 mL, less than 1 mL, less than 900 uL, less than 800 uL, less than 700 uL, less than 600 uL, less than 500 uL, less than 400 uL, less than 300 uL, less than 200 uL, less than 100 uL, less than 90 uL, less than 80 uL, less than 70 uL, less than 60 uL, less than 50 uL, less than 45 uL, less than 40 uL, less than 35 uL, less than 30 uL, less than 25 uL, less than 20 uL, less than 15 uL, less than 12 uL, less than 10 uL, less than 9 uL, less than 8 uL, less than 7 uL, less than 6 uL, or less than 5 uL. All combinations of the above-referenced ranges are possible. For example, the volume of each droplet administered by the applicator device may be about 1 uL to about 5 mL, or about 2 uL to about 1 mL, or about 3 uL to about 900 uL, or about 4 uL to about 900 uL, or about 5 uL to about 500 uL, or about 5 uL to about 400 uL, or about 5 uL to about 200 ul, or about 5 uL to about 100 uL, or about 5 uL to about 50 uL, or about 5 uL to about 20 uL, or about 5 uL to about 10 uL.

The dispenser tip may be able to deliver a plurality of droplets, e.g., 5, 10, 20, 30, 40, 50, 60 or more droplets.

In some embodiments, the applicator device includes a drip guard to aid in preventing the pharmaceutical composition from sliding down the sides of the device onto a user's hand that is holding the device. In some embodiments, the drip guard may be in the form of a moat having a trough for catching the pharmaceutical composition. In some embodiments, the drip guard surrounds at least a portion of the tapered tip of the dispenser tip.

As seen in FIGS. 5-8, the dispenser tip 20 includes a drip guard 26 in the form of an annular ring forming an annular trough 36 for receiving one or more droplets flowing down the sides of the tapered tip 22. The trough may be sized to hold at least 1, at least 2, at least 3, at least 4 or at least 5 droplets, or any other suitable number of droplets.

As seen in FIGS. 5 and 7, the dispenser drip guard 26 surrounds a proximal portion of the tapered tip 22.

In some embodiments, the drip guard defines the largest outer diameter of the dispenser tip. For example as seen in FIG. 7, the diameter of the drip guard 26 is the largest diameter of the dispenser tip 20.

In some embodiments, the drip guard has a diameter of about 0.1 to about 1 inch, about 0.15 to about 0.8 inches, about 0.2 to about 0.6 inches, about 0.3 to about 0.5 inches, about 0.3 to about 0.45 inches, or about 0.404 inches.

In some embodiments, the applicator device enables the ability to routinely deliver material with the same concentration as the concentration in the ampule and that at the time of contact with the skin the material delivered has a concentration of or about 0.7% w/v.

In some embodiments, the dispenser tip 20 includes an attachment portion 28 that may interface with the tube 50. In some embodiments, the attachment portion 28 is attached to the tube 50. For example, as shown in FIG. 4, at least a portion of the attachment portion 28 may contact at least a portion of the tube 50. The dispenser tip 20 and tube 50 may be attached to one another via adhesive, welding, ultrasonic welding, UV glue, interference fit, mechanical interlock, threaded engagement, snap fit engagement, fasteners, or via any other suitable arrangement. One or more intermediate components may be used to attach the dispenser tip to the tube. In some embodiments, the dispenser tip 20 and tube 50 are attached to one another to form a hermetic seal.

The tip may be made of a polymeric material, such as plastic or thermoplastic. In some embodiments, the tip is made of a polypropylene homopolymer. In some embodiments, the tip is made of a transparent or translucent material. The transparent or translucent material may permit a user to see composition flowing through the tip during administration. In some embodiments, the composition is colored to help the user see the composition as it flows through the tip. Other portions of the applicator device may also be transparent or translucent, such as the tube, the ampule, and the cap.

In some embodiments, the applicator device includes a filter that permits passage of the pharmaceutical composition and inhibits passage of broken ampule shards.

The filter may filter out aggregates, particles, pieces of material or the like. These aggregates, particles, or piece of materials may be but are not limited to glass particles, plastic particles, precipitates from the liquid drug formulation or other aggregates.

The filter can made of plastic with one or more holes or alternatively can be a mesh material. The filter can be made of polyester, polyethylene, polyethylene terephthalate (PET), coPET or other polymer or fiber-based materials.

In some embodiments, the filter has the shape of a cylinder, a rectangular prism, a cube, or any other suitable shape.

In some embodiments, the filter is a cylinder having an outer diameter and a length. In some embodiments, the filter may have an outer diameter of about 0.05 inches to about 0.5 inches, 0.1 inches to about 0.3 inches, 0.12 inches to about 0.14 inches, or about 0.135 inches. In some embodiments, the filter may have a length of about 0.1 inches to about 0.3 inches, 0.12 inches to about 0.18 inches, 0.13 inches to about 0.17 inches, 0.14 inches to about 0.15 inches, or about 0.147 inches, or about 0.169 inches.

In some embodiments, the filter has a density of greater than or equal to about 2 grams per cubic inch, greater than or equal to about 2.5 grams per cubic inch, or greater than or equal to about 3 grams per cubic inch. In some embodiments, the filter has a density of less than about 5 grams per cubic inch, less than about 4 grams per cubic inch, or less than about 3.5 grams per cubic inch. In some embodiments, the filter may have a density of about 2 to about 4 grams per cubic inch, or about 2.5 to about 3.5 grams per cubic inch, or about 3 grams per cubic inch.

Figure 10A:
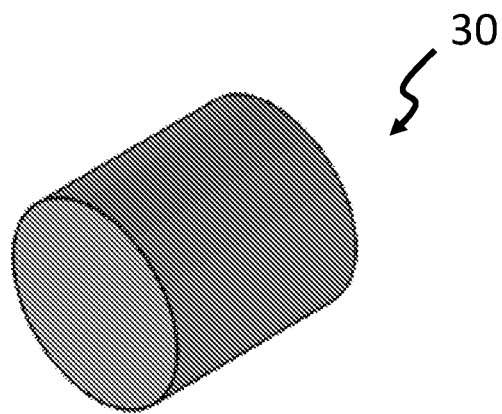
FIG. 10A is a perspective view of a filter of an applicator device according to some aspects of the invention.
Figure 10B:
FIG. 10B is a side view of the filter of FIG. 10A.
Figure 10C:
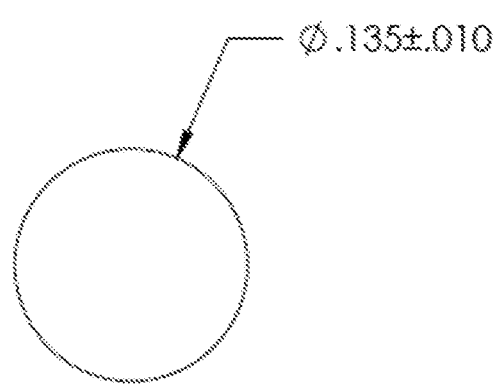
FIG. 10C is a top plan view of the filter of FIG. 10A.

In the illustrative example shown in FIGS. 10A, 10B and 10C, the filter 30 is in the shape of a cylinder having a length of about 0.147 inches and a diameter of about 0.135 inches. In an alternative embodiment, the filter is in the shape of a cylinder having a length of about 0.169 inches and a diameter of about 0.135 inches.

In some embodiments, the filter is constructed and arranged to permit passage of a fluid having a viscosity of 30 to 100 cps. In some embodiments, the filter is constructed and arranged to prevent passage of broken ampule shards having a particle size of at least 20 µm, at least 50 µm, at least 100 µm, at least 120 µm, at least 130 µm, at least 140 µm, at least 150 µm, at least 200 µm, at least 250 µm, at least 300 µm, or at least 400 µm. In some embodiments, the filter is constructed and arranged to prevent passage of broken ampule shards having a particle size of less than 1 mm, less than 800 µm, less than 700 µm, less than 500 µm, less than 400 µm, less than 300 µm, less than 200 µm, or less than 100 µm. In some embodiments, the filter is constructed and arranged to prevent passage of broken ampule shards having a particle size of about 20 µm to about 1 mm, of about 30 µm to about 800 µm, of about 50 µm to about 500 µm, of about 100 µm to about 300 µm, of about 100 µm to about 200 µm, or of about 120 µm to about 170 µm.

As used herein, the "particle size" of a particle refers to the largest dimension of the particle. For example, if the longest dimension of a particle is 200 µm, but the particle also has a width of only 20 µm and a depth of only 30 µm, the particle size of such a particle would be considered its longest dimension, which is 200 µm.

Filter performance in prohibiting particles of a certain particle size can be tested in accordance with the version of United States Pharmacopoeia (USP) Chapter <788>"Particular Matter in Injections" that is current as of Jun. 15, 2017.

In some embodiments, the filter is constructed and arranged to avoid absorbing more than 35 µL of volume of the pharmaceutical composition as the composition flows through the filter.

According to one aspect of the invention, in some embodiments, the filter is positioned within the dispenser tip of the applicator device. In some embodiments, the dispenser tip has a tapered tip, and the filter is positioned within the walls of the tapered tip. In some embodiments, the filter is held within the tapered tip via an interference fit between the filter and the inner surface of the tapered tip.

In one illustrative embodiment shown in FIG. 4, the filter 30 is positioned within the walls of the tapered tip 22 of the dispenser tip 20.

In some embodiments, a distal end of the filter is compressed more than a proximal end of the filter. This may help to ensure that all materials (e.g. pharmaceutical composition and shards) passing through the tip also pass through the filter rather than around the filter.

In some embodiments, the dispenser tip includes a recess to receive the filter.

In the embodiment shown in FIGS. 7 and 8, the dispenser tip 20 includes a recess 37 sized and shaped to receive the filter 30. The recess may be flanked by narrowing channels on the distal and proximal sides of the recess to help keep the filter positioned within the recess 37. For example, as seen in FIG. 7, a channel portion 47 at the distal end of the recess 37 has a diameter that is smaller than that of the recess 37, and a channel portion 57 at a proximal end of the recess 37 has a diameter that is smaller than that of the recess 37.

In some embodiments, the applicator device has a cap. According to one aspect of the invention, the cap is used to protect the dispenser tip from being damaged. In some embodiments, the cap does not actually create a seal when in a closed position, but instead permits venting of the dispenser tip through the cap, e.g. through a through-hole opening in the cap, or through an opening between the dispenser tip and the cap. In some embodiments, vent channels in the dispenser tip permit venting of the dispenser tip through the cap. In some embodiments, undesired pharmaceutical composition can be dispensed controllably into the cap rather than onto the patient or another containment device.

In some embodiments, the cap has an opening that receives at least a portion of one or more other applicator device components. The cap opening may removably couple to at least a portion of one or more other applicator device components when in the closed position. For example, in some embodiments, the cap may receive at least a portion of the dispenser tip and may couple to the dispenser tip when in the closed position. In some embodiments, the cap receives at least a portion of the tube and couple to the tube when in the closed position.

In the illustrative embodiment shown in FIG. 4, the cap 10 has an opening that receives a portion of the dispenser tip 20 and couples to the dispenser tip 20 when the cap is in the closed position. The opening 11 may be seen in FIG. 11. The cap may have a coupling feature that may permit the cap to couple to another component of the applicator device. According to one aspect of the invention, the cap may have a coupling feature that permits the cap to couple to another component of the applicator device without creating a seal against the component to which the cap is coupled to. In other words, in some embodiments, the coupling feature permits venting of the dispenser tip through the cap, e.g., through vent channels in the dispenser tip when the cap is in a closed position.

In one illustrative embodiment, the coupling feature of the cap comprises one or more ribs located within the inside of the cap. The ribs may protrude radially inwardly from the inner surface of the cap. When another component of the applicator device is inserted into the cap opening, the ribs may come into contact against a surface of the component. The ribs may be sized and positioned such that the amount of clearance between the ribs is smaller than the area occupied by the portion of the component received into the cap. As a result, the ribs may press radially inwardly upon the surface of the component, and the cap may be coupled to the component via an interference fit.

Figure 11:
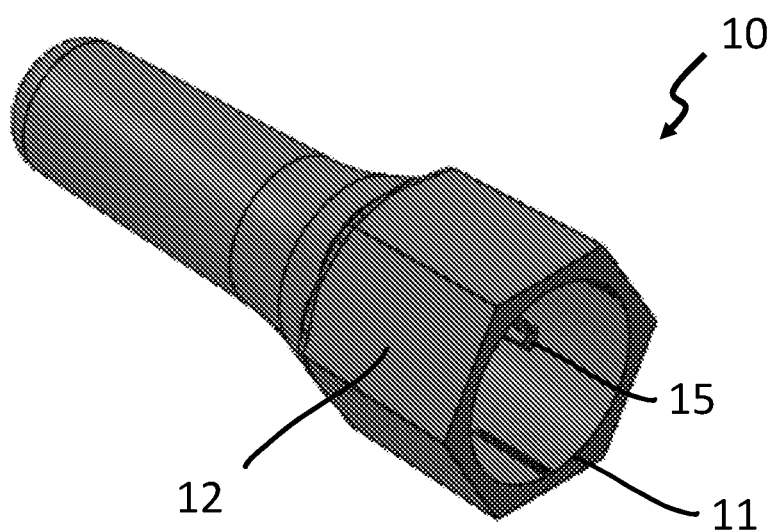
FIG. 11 is a perspective view of a cap of an applicator device according to some aspects of the invention.
Figure 13:
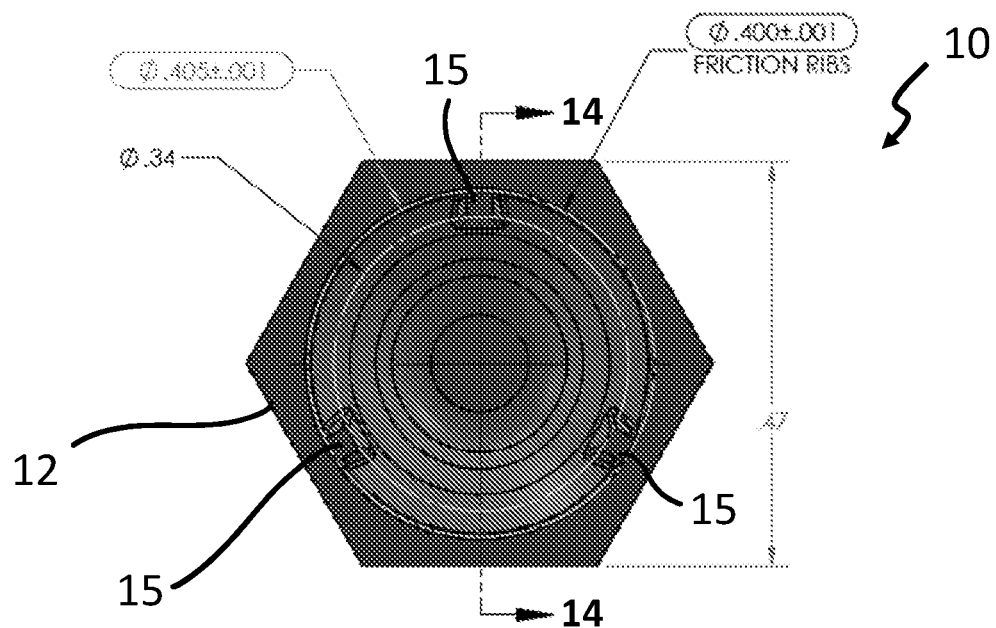
FIG. 13 is a bottom plan view of the cap of FIG. 11.
Figure 14:
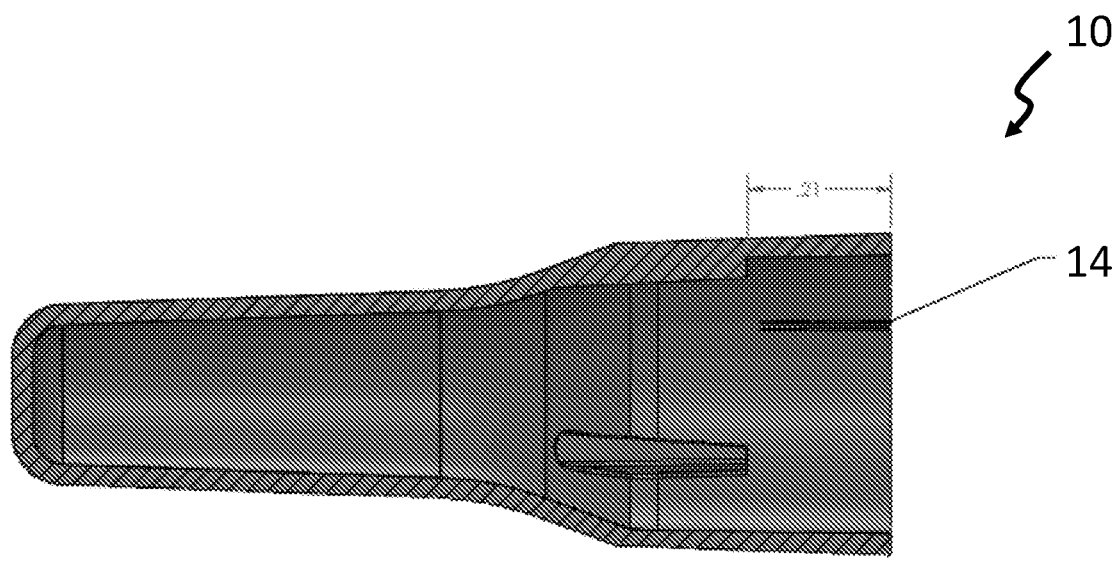
FIG. 14 is a cross-sectional view of the cap of FIG. 13 taken along line 14-14 of FIG. 13.

In the illustrative embodiment shown in FIGS. 4, 11 and 13, the applicator device has a cap 10 that includes a plurality of ribs 15. As best seen in FIG. 13, the ribs 15 may be evenly spaced from one another. While this illustrative embodiment uses three ribs, it should be appreciated that any suitable number of ribs may be used, such as 2, 3, 4, 5, 6, 7 or 8 ribs.

As best seen in FIG. 4, the cap 10 engages with a portion of the dispenser tip 20. When the dispenser tip is received within the cap, the ribs 15 may press against an outer surface of the dispenser tip to couple the cap to the dispenser tip. The cap may engage with a portion of the dispenser tip having the largest diameter. In some embodiments, the cap engages with the drip guard 26 of the dispenser tip. The ribs 15 may press against an outer surface of the drip guard 26.

In some embodiments, although the ribs create an interference fit against a portion of the dispenser tip 20, the ribs do not create a seal between the cap and the dispenser tip. In some embodiments, the ribs may be fused to the tube via ultrasonic welding.

It should be appreciated that other coupling arrangements may be used. For example, the coupling feature may operate via mechanical interlock, via a threaded engagement, or any other suitable coupling arrangement.

In some embodiments, in addition to or instead of engaging with the dispenser tip, the cap may engage with the tube when in the closed position. For example, the cap may press against an outer surface of the tube, connect with the tube via corresponding threads, etc.

According to one aspect of the invention, the cap permits venting through the opening that receives another component of the applicator device. In some embodiments, the cap has only one opening, and no other holes besides the opening for venting. In such embodiments, the cap has continuous, unbroken outer surface devoid of holes, besides the opening. In other embodiments, in addition to the opening, the cap may have one or more holes for venting.

In some embodiments, after a period of time, at least a portion of the pharmaceutical composition (e.g., a portion of the pharmaceutical composition in the dispenser tip positioned towards the distal opening) may harden to create a seal, enabling a self-sealing effect, and may prevent the pharmaceutical composition from flowing out of the dispenser tip and/or prevent exposure of the pharmaceutical composition to ambient air. In some embodiments, the self-sealing effect may be caused by evaporation of solvent (e.g., water or alcohol) from the pharmaceutical composition, which may leave behind a solid. In some embodiments, the venting feature of the cap allows solvent to evaporate and thus may enable the self-sealing effect.

In some embodiments, the self-sealing feature may serve as a safety feature, e.g., to prevent unwanted release of the pharmaceutical composition after treatment, to prohibit subsequent use which could, for example, cause cross-contamination between different patients. The self-sealing feature could serve as a tamper-evident feature that could prevent users from being able to use an applicator that had previously been activated. In some embodiments, the self-sealing feature may help to prevent degradation of oxidation of the active ingredient of the pharmaceutical composition.

In some embodiments the applicator is used to treat a subject (e.g., a child) with multiple skin lesions, and the user may need to set the applicator down midway through dispensing the pharmaceutical composition. The user may need to start and stop application multiple times during a single treatment while attending to a patient. In some embodiments, the applicator would not dry out for at least 1, 5, 10, 20, 30, 45, 60 minutes when not in use, but after the first lesion has been treated.

Figure 12:
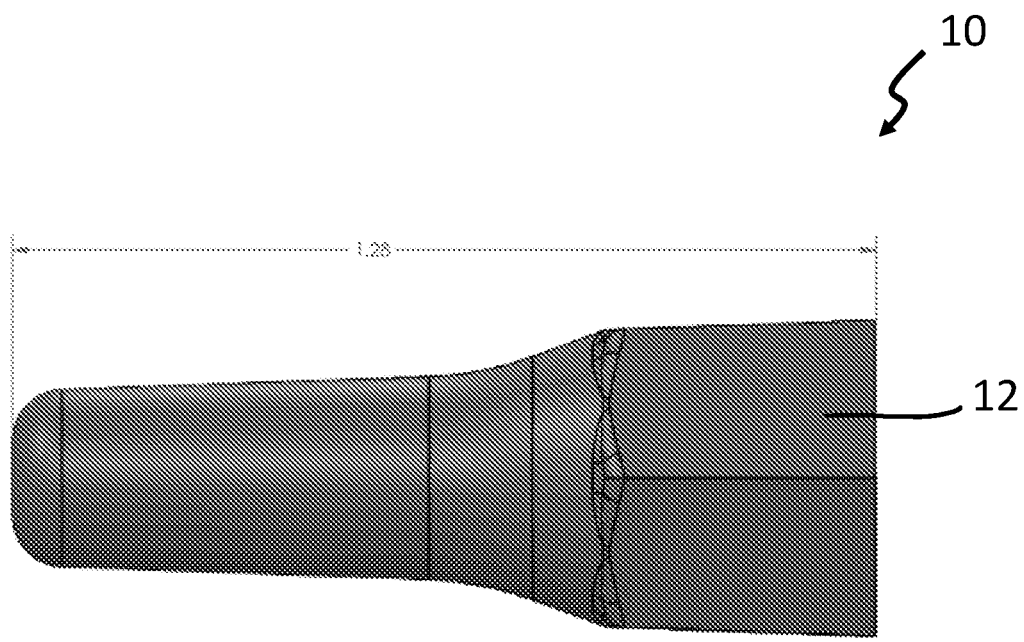
FIG. 12 is a side view of the cap of FIG. 11.

In some embodiments, the cap includes a feature that prevents rolling of the cap and the entire device applicator when the cap is in the closed position. In some embodiments, the cap may include one or more flat surfaces that prevent the cap from rolling. As seen in FIGS. 11-13, the cap 10 may include six flat surfaces 12. It should be appreciated that any number of flat surfaces may be used. In some embodiments, the cap includes 1, 2, 3, 4, 5, 6, 7, 8, 9, 10 or any other suitable number of flat surfaces. The flat surfaces may be the same size to form a regular shape. For example, in the embodiment shown in FIGS. 11-13, the flat surfaces 12 form a hexagon.

In some embodiments, the flat surfaces are positioned at a proximal end the cap that receives the dispenser tip.

FIGS. 11-14 provide dimensions (shown in inches) for one illustrative embodiment of a cap. It should be understood that such dimensions are provided as an illustrative example, and that the applicator device may include a cap having different dimensions than those shown in FIGS. 11-14.

In some embodiments, the cap may have a length of about 0.5 to about 3 inches, about 1 inch to about 2 inches, about 1 inch to about 1.5 inches, or about 1.28 inches.

In some embodiments, the cap may have a maximum outer width (e.g., measured from one flat surface 12 to another) of about 0.1 to about 1 inch, about 0.3 to about 0.8 inches, about 0.4 to about 0.5 inches, or about 0.47 inches. In some embodiments, the cap includes an opening for receiving the dispenser tip and/or the tube. The opening may be circular and may have a diameter of about 0.1 to about 1 inch, about 0.2 to about 0.9 inches, about 0.3 to about 0.8 inches, about 0.3 to about 0.5 inches, about 0.35 to about 0.45 inches, or about 0.4 inches.

In some embodiments, the cap may be used to collect undesired drops—e.g., if, during administration of drug, the user has squeezed too hard such that more drops than desired are released, the cap may be used to catch the excess drops.

In some embodiments, to aid in venting, one or more grooves may be present on a surface of the dispenser tip that interfaces with the cap, and/or on a surface of the cap that interfaces with the dispenser tip. Such groove may create one or more gaps between the dispenser tip and the cap when the cap is in the closed position to prevent sealing between the cap and the dispenser tip, and to promote venting of solvent as discussed above. In some embodiments, when the cap is in the closed position, the cap attaches to and interfaces with an interfacing surface of the dispenser tip, such as an outer surface of a drip guard of the dispenser tip. In some embodiments, the interfacing surface of the dispenser tip may have one or more grooves. Alternatively or in addition, a surface of the cap, e.g., an inner surface of the cap that interfaces with the surface of the dispenser tip may have one or more grooves.

Figure 15:
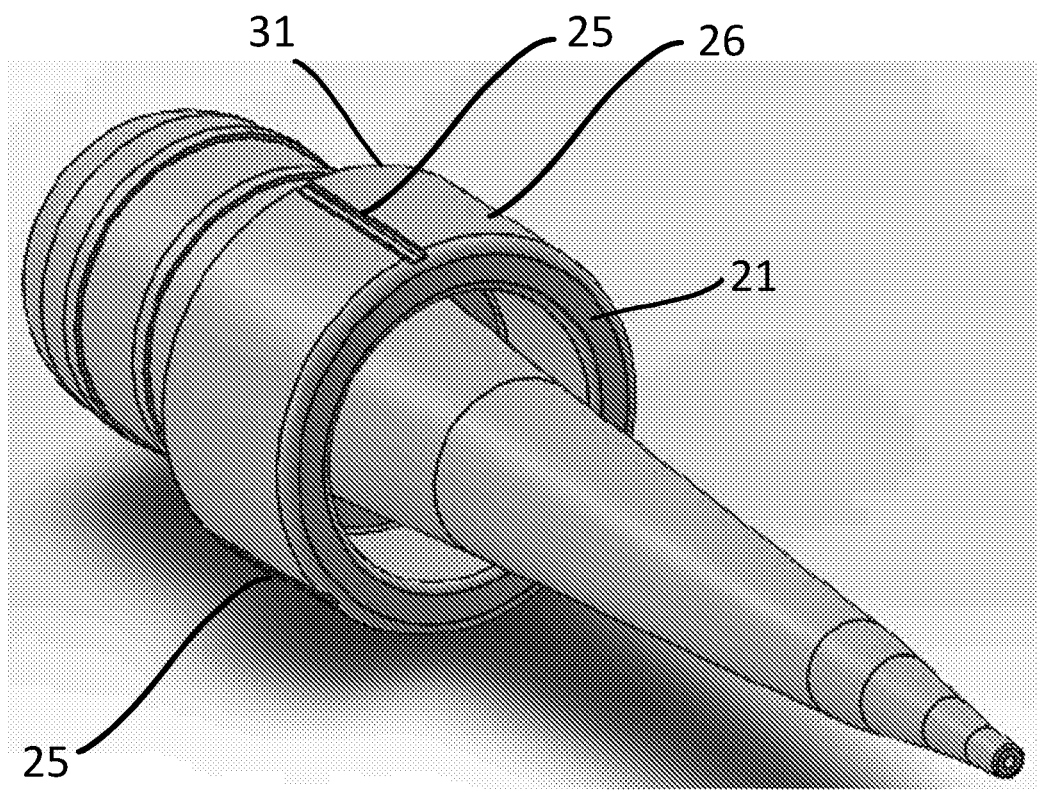
FIG. 15 is a perspective view of a dispenser tip of an applicator device having a plurality of vents.
Figure 16:
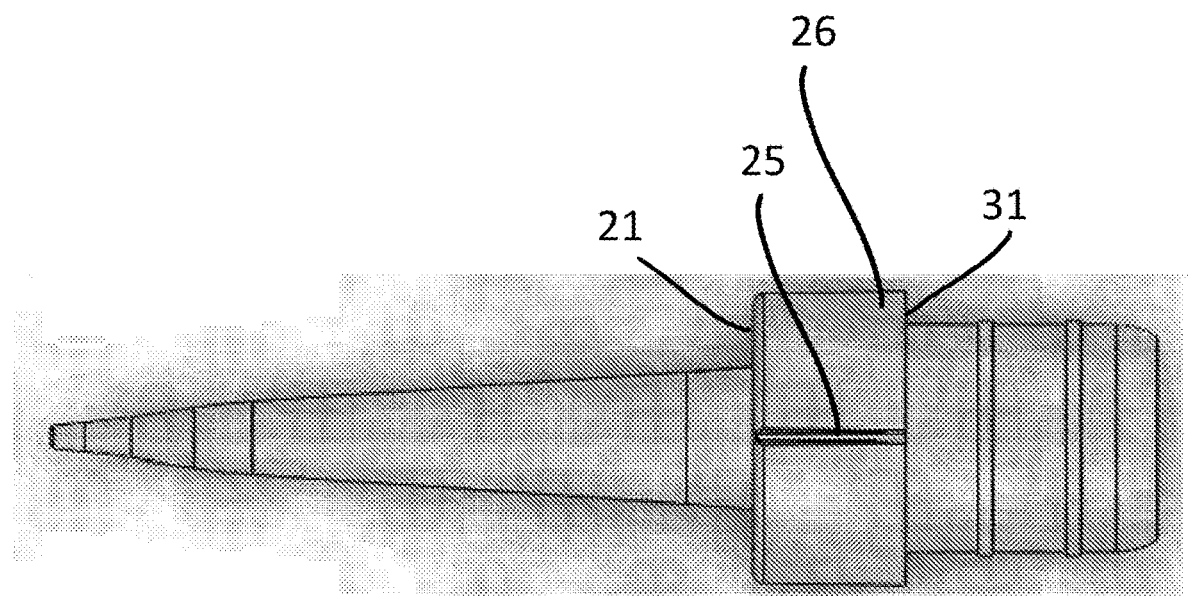
FIG. 16 is a side view of the dispenser tip of FIG. 15.
Figure 17:
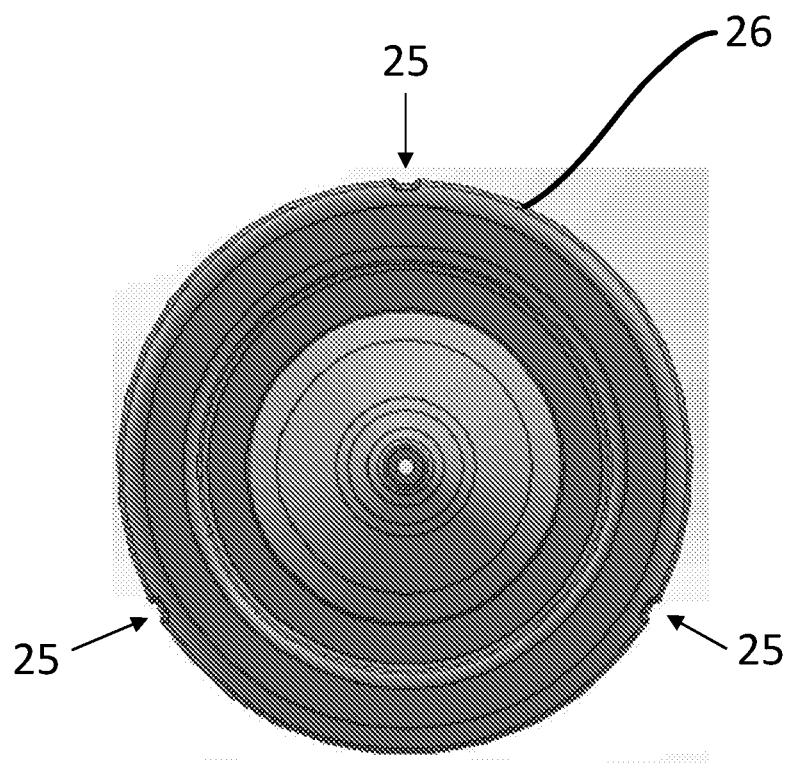
FIG. 17 is a top plan view of the dispenser tip of FIG. 15.

One illustrative embodiment of a dispenser tip having one or more grooves is shown in FIGS. 15-17. As seen in FIG. 15, the grooves 25 are formed in the outer surface of the drip guard 26. In some embodiments, the groove extends from a distal edge 21 of the drip guard 26 to a proximal edge 31 of the drip guard 26. However, it should be appreciated that, in other embodiments, the groove may be of a different length. For example, the groove may extend from the distal edge of the drip guard to a point on the surface such that the groove extends partially across the surface but not from distal edge to proximal edge. In the embodiment of FIG. 15-17, the groove is linear. However, it should be appreciated that other groove shapes can be used. For example, the groove may have a tortuous, curved, or other non-linear path. As seen in FIG. 17, in some embodiments, the dispenser tip includes more than one vent. The embodiment shown in FIG. 17 includes three vents. However, it should be appreciated that other numbers of vents can be used, such as 1, 2, 3, 4, 5, 6, 7, 8, 9, 10 vents, or any other suitable number of vents. In some embodiments, the vents are equally spaced from one another. The vents may be radially spaced from one another on the circumference of a surface. The vents may be positioned on a surface of a portion of the dispenser tip that has the largest diameter. As seen in FIG. 17, with three vents 25, the vents are spaced 120 degrees from one another along the circumference of the drip guard 26. However, it should be appreciated that, in other embodiments, the vents may be non-uniformly spaced from one another.

FIGS. 18-21 provide dimensions (shown in inches for distances and degrees for angles) for one illustrative embodiment of a dispenser tip. It should be understood that such dimensions are provided as an illustrative example, and that the applicator device may include a dispenser tip having different dimensions than those shown in FIGS. 18-21.

Figure 21:
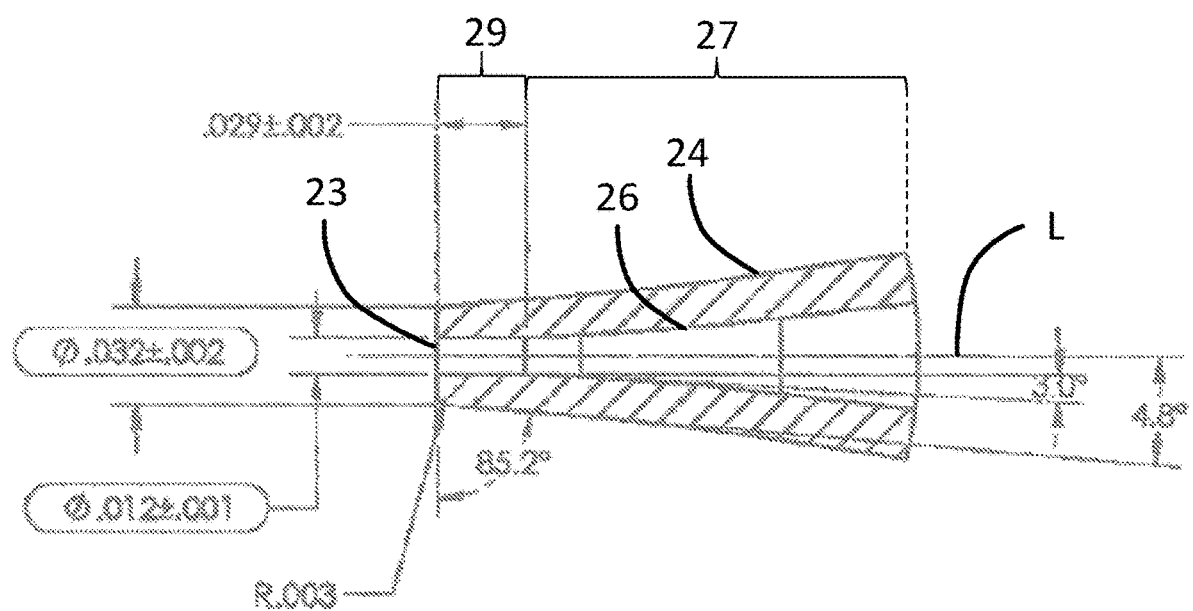
FIG. 21 is a detail view of the encircled region 21 of the dispenser tip of FIG. 19.

As seen in FIG. 21, the opening 23 may have an outer diameter of about 0.032 inches+/−0.002 inches, and an inner diameter of about 0.012 inches+/−0.001 inches.

The dispenser tip 20 includes a tapered tip 22, which includes an outer surface and an inner surface. As seen in FIG. 21, which depicts a detail view of the encircled region 21 of the dispenser tip of FIG. 19, the tapered tip 22 has an outer surface 24 and an inner surface 26. The inner surface 26 has a first portion 27 that is tapered, and a second portion 29 that is straight, or has a taper angle that is different than that of the first portion. In some embodiments, the second portion may have a taper angle that is smaller than that of the first portion. As also seen in the embodiment of FIG. 9, the taper angle of the outer surface 24 is different than that of the taper angle of the first portion 27 of the inner surface 26. In the embodiment of FIG. 21, the inner surface has a taper angle of about 3 degrees, and the outer surface has a taper angle of about 4.8 degrees.

Figure 18:
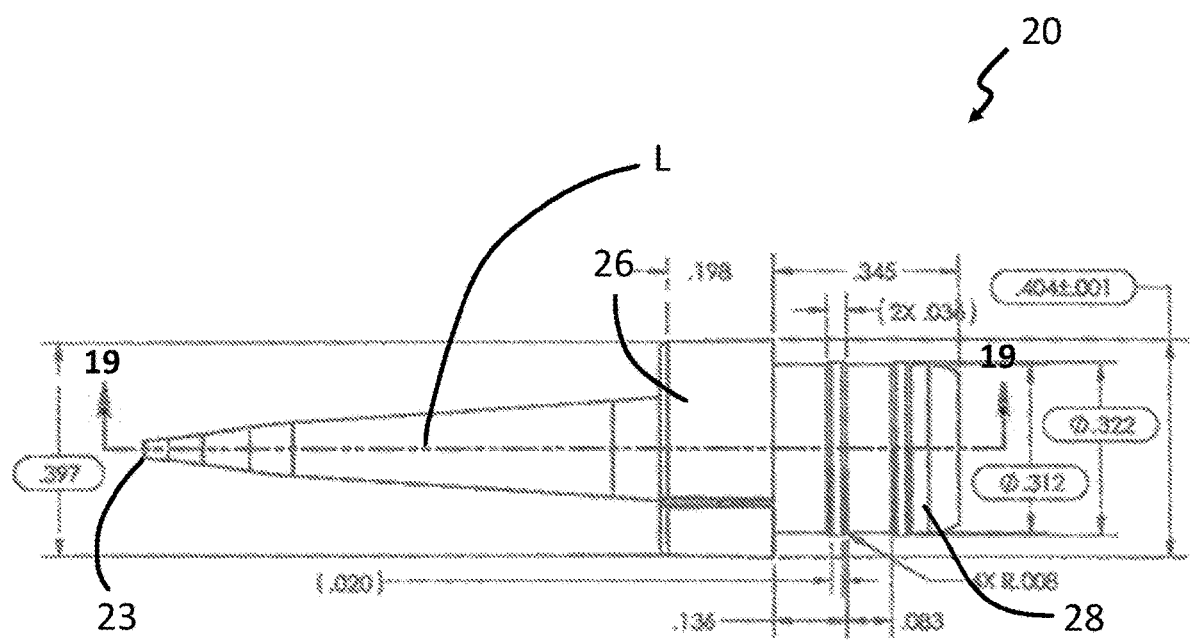
FIG. 18 is a side view of the dispenser tip of FIG. 15.
Figure 20:
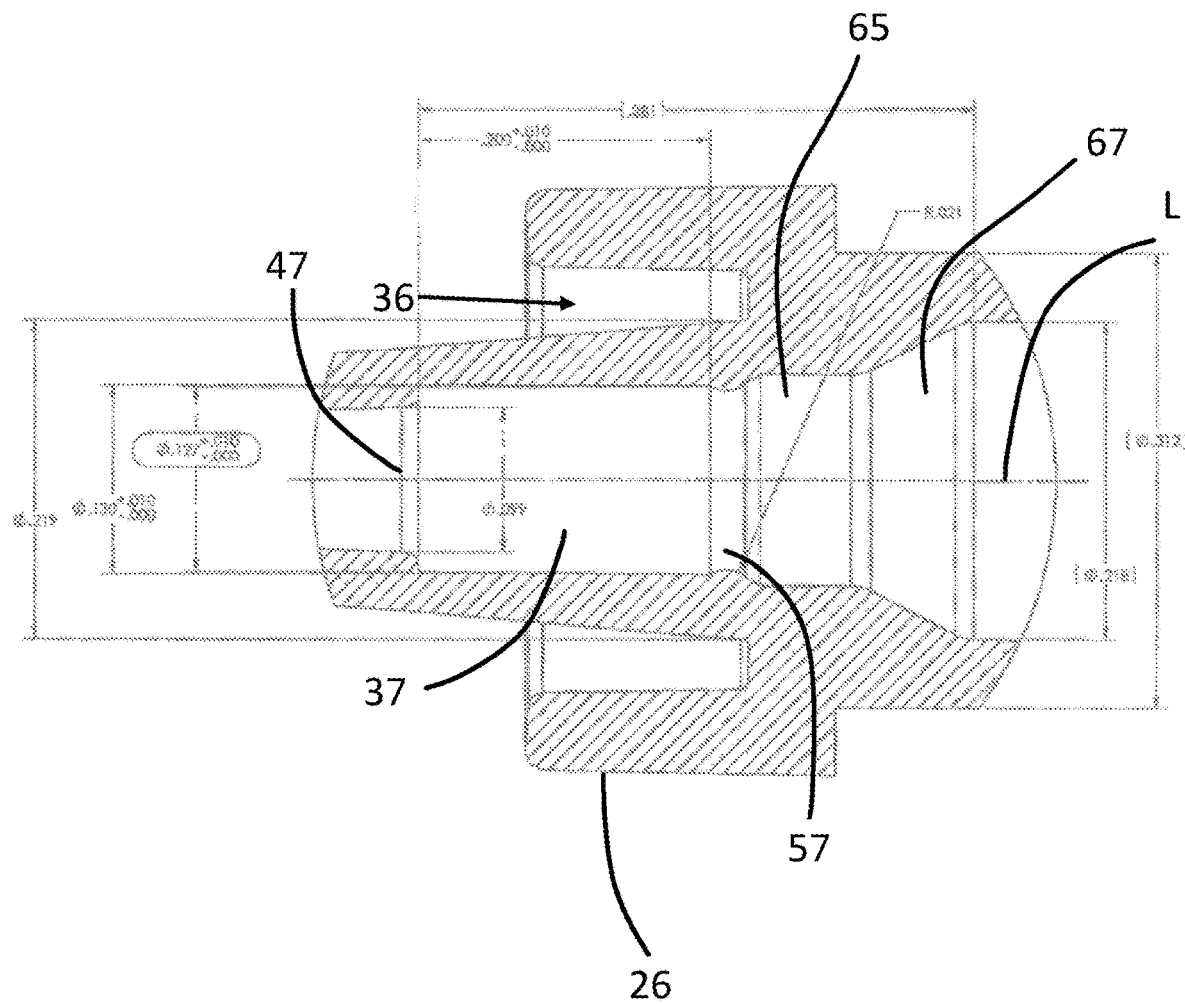
FIG. 20 is a detail view of the encircled region 20 of the dispenser tip of FIG. 19.

The tapered tip has a longitudinal axis L, as shown in FIGS. 18, 20 and 21. The tapered tip is rotationally symmetric about the longitudinal axis L.

As shown in FIG. 21, the inner surface 26 of the dispenser tip at a distal portion of the tip has a decreased taper as compared to the rest of the inner surface, or is a straight-walled channel with no taper. In some embodiments, the distal portion of the tip having a straight-walled inner channel spans a distance along the longitudinal axis L of the dispenser tip that is about 0.029+/−0.002 inches long.

The dispenser tip 20 includes an attachment portion 28 that interfaces with the tube 50. In some embodiments, the attachment portion 28 is attached to the tube 50.

Figure 19:
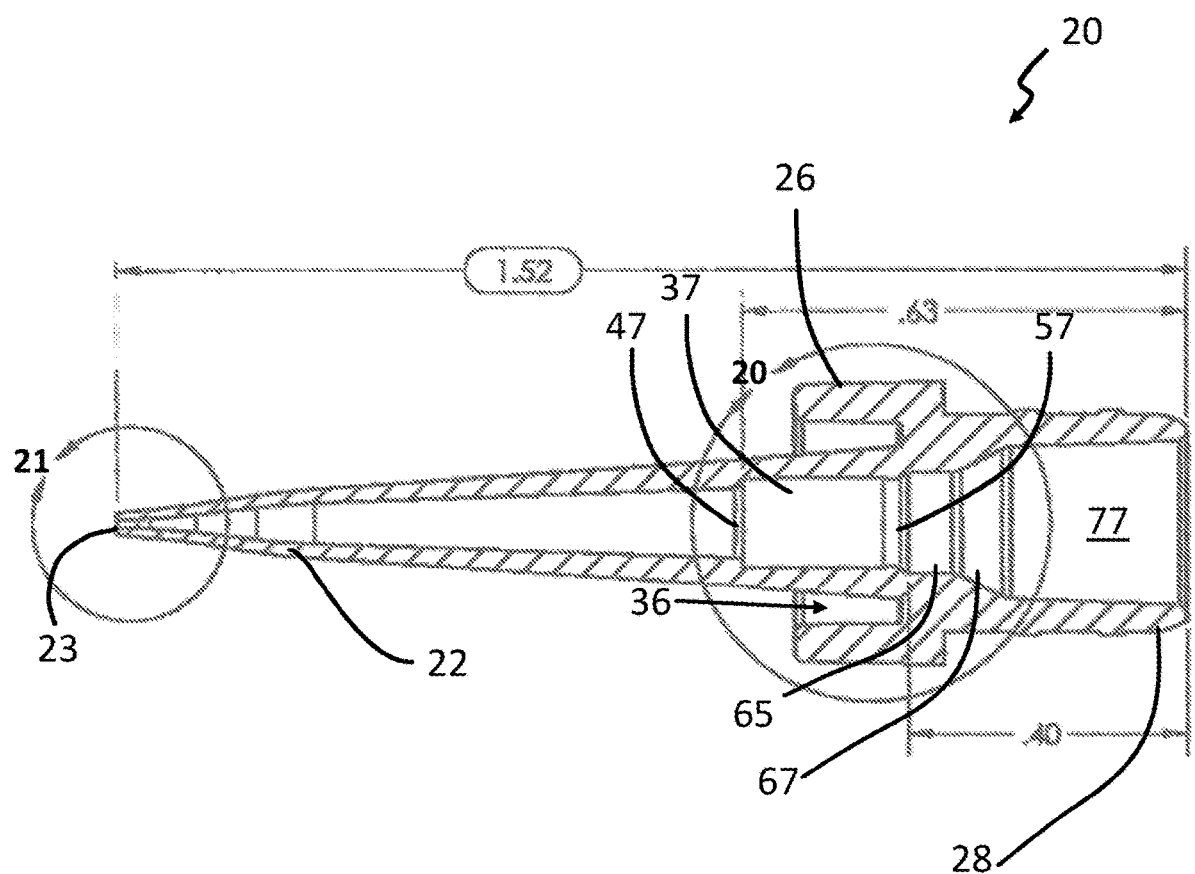
FIG. 19 is a cross-sectional view of the dispenser tip of FIG. 18 taken along line 19-19 of FIG. 18.

The applicator device includes a filter that is positioned within the dispenser tip of the applicator device. In the embodiment shown in FIGS. 19 and 20, the dispenser tip 20 includes a recess 37 sized and shaped to receive the filter 30. The recess may be flanked by narrowing channels on the distal and proximal sides of the recess to help keep the filter positioned within the recess 37. For example, as seen in FIGS. 19 and 20, a channel portion 47 at the distal end of the recess 37 has a diameter that is smaller than that of the recess 37, and a channel portion 57 at a proximal end of the recess 37 has a diameter that is smaller than that of the recess 37. In the embodiment of FIGS. 19 and 20, the dispenser tip also includes a funnel region 67 that serves as a transition from the smaller-diameter filter recess 37 to the larger-diameter chamber 77 that is inserted into the dispenser tube. In the embodiment of FIGS. 19 and 20, the dispenser tip further includes a straight-walled channel region 65 between the filter recess 37 and the funnel region 67.

According to one aspect, the tube is compressible to induce a pressure increase inside the tube to dispense the pharmaceutical composition out of the dispenser tip. In some embodiments, the tube can be compressible to induce a pressure increase inside the tube in excess of about 1.0 atm, 1.1 atm, 1.2 atm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm, or 40 atm. The tube can be compressible to induce a pressure increase inside the tube greater than or equal to about 1.0 atm, 1.1 atm, 1.2 atm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm, or 40 atm. In some cases, the pressure in the tube is increased by a factor of at most about 100 atm, 50 atm, 40 atm, 30 atm, 20 atm, 10 atm or 5 atm. In some examples, the tube is compressible to induce a pressure increase in the tube from about 1 atm to 20 atm, 1 atm to 15 atm, 1 atm to 10 atm, or 1 atm to 5 atm.

In some cases, the tube can be compressible to induce a pressure inside the tube that is greater than about 1.0 atm, 1.1 atm, 1.2 atm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm, or 40 atm. The tube can be compressible to induce a pressure inside the tube that is greater than or equal to about 1.0 atm, 1.1 atm, 1.2 atm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm, or 40 atm. In some cases, the pressure in the tube is increased to at most about 100 atm, 50 atm, 40 atm, 30 atm, 20 atm, 10 atm or 5 atm. In some examples, the tube is compressible to induce a pressure in the tube from about 1 atm to 20 atm, 1 atm to 15 atm, 1 atm to 10 atm, or 1 atm to 5 atm.

The tube can have a shape that is mainly or substantially cylindrical or spherical. Alternatively, the tube can have a shape that is mainly or substantially rectangular. The tube can have 1 edge. Alternatively, the tube can have 2 or more edges. Further, the tube can have an irregular shape.

The tube can be at least partially or wholly formed of a polymeric material (e.g., plastic). The plastic used can be but is not limited to polypropanol, low-density polyethylene, medium-density polyethylene, high-density polyethylene, or polytetrafluoroethylene or some combination thereof. As an alternative, the tube can be at least partially or wholly formed of a metallic material (e.g., stainless steel or aluminum). In an example, a portion of the tube is formed of a polymeric material, and a remainder of the tube is formed of a metallic material.

The tube can be at least partially or wholly formed of a polymeric material (e.g., plastic). As an alternative, the tube can be at least partially or wholly formed of a metallic material (e.g., stainless steel or aluminum). In an example, a portion of the tube is formed of a polymeric material, and a remainder of the tube is formed of a metallic material.

In some embodiments, the tube can have a volume from about 0.1 mL to 10 mL, or about 0.2 mL to 9 mL, or about 0.3 mL to 8 mL, or about 0.4 mL to 8 mL, or about 0.5 to 6 mL, or about 2 mL to 4 mL or less or equal to about 3 mL. The tube can have a volume less than or equal to about 10 mL, about 8 mL, about 6 mL, about 5 mL, about 4 mL, about 3 mL, about 2.5 mL, or about 2 mL.

In some embodiments, the tube has a length of about 0.5 inches to about 5 inches, about 1 inch to about 4 inches, about 1.5 inches to about 3.5 inches, about 2 inches to about 3 inches, or about 2.5 inches.

In some embodiments, the tube has an internal diameter of about 0.1 inches to about 1 inch, about 0.15 to about 0.7 inches, about 0.2 to about 0.6 inches, about 0.25 to about 0.4 inches, about 0.3 to about 0.35 inches, or about 0.31 inches.

In some embodiments, the tube may sit within a paperboard or cardboard sleeve that may protect the pharmaceutical composition from light and may decrease the risk of glass poking the user in the case a glass shard punctures the tube.

The applicator can contain an ampule that holds the pharmaceutical composition. The ampule may be constructed and arranged to be broken to release the pharmaceutical composition. In some cases, the ampule can be crushed into several pieces. In some cases, the outer tube can be compressed to crush and break the ampule, thereby releasing the pharmaceutical composition. FIGS. 2 and 4 depict an illustrative embodiment of an ampule 60.

In some embodiments, the force needed to crush the ampule is about 1 to 20 lbf, about 5 to 15 lbf, about 7 to 13 lbf, or about 9-10 lbf.

In some embodiments, an ampule is made of USP type I borosilicate glass, USP type II borosilicate glass, or USP type III borosilicate glass. As an alternative, the ampule can be formed of a polymeric material, such as plastic or rubber. As another alternative, the ampule could be made out of plastic lined with PTFE or plastic lined with metallic foil. As another alternative, the ampule could also be made out of ceramic. The ampule in such cases may be punctured, crushed or torn open to release the pharmaceutical composition.

In some embodiments, the pharmaceutical composition may be contained in a different container other than an ampule. For example, the container may be a pouch with flexible walls. In some embodiments, the pharmaceutical composition is held directly in the tube itself without an additional container to contain the pharmaceutical composition.

In some embodiments, the pharmaceutical composition may be separated into two or more components and are combined together shortly before use. The user may break a seal or other separating barrier to combine the two components together.

In some embodiments, the ampule can have a volume of less than or equal to about 3000 mL, less than or equal to about 2000 mL, less than or equal to about 1000 mL, less than or equal to about 500 mL, less than or equal to about 300 mL, or less than or equal to about 100 mL. In some embodiments, the ampule can have a volume of greater than about 100 mL, greater than about 300 mL, greater than about 500 mL, greater than about 1000 mL, greater than about 2000 mL, or greater than about 3000 mL. In some embodiments, the ampule can have a volume from about 10 mL to 3000 mL, or about 50 mL to 2500 mL, or about 100 mL to 2000 mL, or about 200 mL to 1400 mL, or about 300 mL to 1000 mL, or about 400 mL to 800 mL, or about 500 mL to 700 mL.

In some embodiments, the ampule contains about 100 to 2000 mL of a pharmaceutical composition.

In some embodiments, the ampule has a length of about 10 mm to about 100 mm, about 20 mm to about 90 mm, about 30 mm to about 80 mm, about 40 mm to about 60 mm, about 45 mm to about 55 mm, or about 48.99 mm.

In some embodiments, the ampule has an outer diameter of about 1 mm to about 15 mm, about 3 mm to about 12 mm, about 5 mm to about 9 mm, about 6 mm to about 8 mmo about 6.5 mm to about 7.5 mm, or about 7 mm.

Examples of different topical compositions held within and delivered by the device applicator include, but are not limited to: vesicants such as cantharidin, ingenol melbutate or nitrogen mustard, antibacterials such as mupirocin and clindamycin, anthralin, antifungal agents such as clotrimazole, ketoconazole and terbafine, benzoyl peroxide, tea tree oil, sandalwood extracts, *solanum* undatum extract, *thuja* extract, podophyllin, podofilox, digoxin, furosemide, sinecatechins, nitric oxide, green tea extracts, salicylic acid, coal tar, corticosteroids, retinoids, antibiotics, anti-inflammatory agents, anesthetics, decongestants, steroids, anti-itch medications, immunomodulatory skin medications, haptens, contact allegens, squaric acid dibutylester, diphenylcyclopropenone, sunscreen, topical cosmetics, self-tanning agents, hyaluronic acid, dihydroxyacetone, hydrogen peroxide, tretinoin, bichloracetic acid, trichloroacetic acid, lactic acid, glycolic acid, silver nitrate, potassium hydroxide, sodium hydroxide, dilute povidone iodine, anorectal preparations, antiseptic and germicides, dermatological agents, anti-invectives, anti-rosacea agents, antihistamines, antineoplastics, antivirals, astringents, debriding agents, depigmenting agents, emollients, keratolytics, non-steroidal anti-inflammatories, photochemotherapeutics, rubefacient, nasal preparations, lubricants, irrigations, ophthalmic agents, anti-angiogenic ophthalmic agents, mydriatics, glaucoma agents, otic agents, cerumenolytics, vaginal agents, spermicides, povidine iodine, imiquimod, oxidizers, hydrogen peroxide, or other toll-like receptor agonists or antagonists.

In some embodiments, the pharmaceutical composition may include at least 20% or greater of at least one non-aqueous solvent, e.g., acetone, ether, ethanol, DMSO, amyl acetate or chloroform). In some embodiments, the ampule may be constructed and arranged to maintain the stability of the pharmaceutical composition such that, after a period of one month, the concentration of the active ingredient is at least 98% of the starting concentration and after a period of six months, the concentration is at least 96% of the starting concentration.

In some embodiments, the ampule contains an overlay of inert gas, such as nitrogen or argon.

In some embodiments, the applicator device may be used to topically administer a composition to a subject. The applicator device may topically administer the composition to various body surfaces, including, but not limited to, skin, mucous membranes, genitalia, vagina, anus, nails, hair, nose, eye, ear, or mouth, including lips, teeth, tongue, and gums.

The applicator device may be used to treat different conditions, such as, but not limited to, warts, molluscum contagiosum, mucous membrane phemphigoid, nasal polyps, conjunctivitis, otitis, cold sores, dentin hypersensitivity, tooth discoloration, halitosis, glossitis, periodontal disease, yeast infections, fungal infections, hemorrhoids, or any other body surface condition. Examples of other body surface conditions include, but are not limited to, seborrheic keratosis, actinic keratosis, milia, age spots, porokeratosis, skin cancer, or other types of skin conditions. While some of the examples and/or embodiments described herein refer to treatment of skin conditions such as skin lesions, it should be appreciated that the applicator device is not limited to use with or on skin, and may be used for topical administration of a composition to any body surface, including mucous membranes, eye, mouth, ear, etc. The inventors have recognized the need for an applicator that can controllably administer a composition to an intended body surface area of a subject.

Examples of conditions of the skin that may be treated by the applicator device include, but are not limited to: fungal infections, athlete's foot, acne, benign epidermal cysts, birthmarks, carbuncle, calluses, cellulitis, cold sores, corns, cutaneous candidiasis, eczema, freckles, hemangioma, hives, lupus, measles, moles, necrotizing fasciitis, pigmentation disorders (drug-induced hyperpigmentation, Dyschromatosis *symmetrica* hereditaria, dyschromatosis universalis hereditaria, familial progressive hyperpigmentation, Galli-Galli disease, hemosiderin hyperpigmentation, idiopathic guttate hypomelanosis, iron metallic discoloration, leukoderma, melasma, Mukamel syndrome, Necklace of Venus, nevus anemicus, nevus depigmentosus, Pallister-Killian syndrome, phylloid hypomelanosis, piebaldism, pigmentatio *reticularis* faciei et colli, pilar cysts, *pityriasis* alba, poikiloderma of civatte, poikiloderma vasculare atrophicans, postinflammatory hyperpigmentation, progressive macular hypomelanosis, pruritus, reticular pigmented anomaly of the flexures, reticulate acropigmentation of Kitamura, Riehl melanosis, Shah-Waardenburg syndrome, shiitake mushroom dermatitis, tar melanosis, titanium metallic discoloration, transient neonatal pustular melanosis, Vagabond's leukomelanoderma, vasospastic macules, Wende-Bauckus syndrome, X-linked reticulate pigmentary disorder, Yemenite deaf-blind hypopigmentation syndrome), psoriasis, rosacea, scars, skin cancer, skin tags, tattoo removal, vitiligo (including, but not limited to, non-segmented vitiligo, and/or segmented vitiligo trichome vitiligo, quadrichrome vitiligo, vitiligo ponctud), warts, hypohidrosis, impetigo, cutis *laxa*, decubitus ulcer, erysipelas, diaper rash, dyshidrotic eczema, canker sore, herpes stomatitis, ichthyosis vulgaris, dermatomyositis, ingrown nails, acrodermatitis, sebaceous cyst, seborrheic keratosis, pilonidal sinus, keloid, lichen planus, actinic keratosis, statis dermatitis, calluses, tinea *versicolor* pemphigoid, mouth ulcers, or shingles.

Examples of conditions of the eye that may be treated by the applicator device include, but are not limited to: conjunctivitis, keratitis, keratoconjunctivitis, allergic conjunctivitis, corneal ulcer, Thygeson's superficial punctate keratitis, vernal keratoconjunctivitis, herpes simplex keratitis, ophthalmic diseases, ocular hypertension, ocular rosacea, keratoconjunctivitis sicca, ocular inflammatory disease, ocular surface disease, corneal inflammation, intraocular inflammation, uveitis, cataracts, glaucoma, fungal eye infections or blepharitis.

Examples of conditions of the ear that may be treated by the applicator device include, but are not limited to: dermatitis of the ear canal, otitis media, otitis externa, vertigo, Meniere's disease, tympanostomy tube otorrhea, chronic suppurative otitis media, cerumen impaction, seborrheic dermatitis, seborrheic keratosis, contact dermatitis, aural eczematoid dermatitis, acute external otitis, granuloma fissuratum, actinic keratoses, cornu cutaneum, basal cell carcinoma, keloid, Hutchinson's freckle, Winkler Disease, auricular chondritis and perichondritis, cylindroma, blue nevus, auricular appendages, Osler-Weber-Rendu Disease, atopic dermatitis, or photoallergic dermatitis.

Examples of conditions of the nose include, but are not limited to: nasal polyps, bacterial nasal infections, rhinitis, rhinosinusitis, sinus infections, allergic rhinitis, chronic atrophic rhinitis, fungal sinusitis, post-nasal drip, or rhinophyma, rhinorrhea.

Some embodiments of the applicator device or system can be used to treat the following: Acral fibrokeratoma, Acrodermatitus enterpathica, Acrokeratoelastoidosis, Actinic keratosis (solar keratoses), Adenoma sebaceum, Angiokeratoma, Atopic Dermatitis, Basal cell carcinoma, Benign fibrous histiocytomas, Bladder cancer, Bowen's disease, Breast cancer, Buschke-Ollendorff syndrome, Cervical cancer, Cervical dysplasia, Cherry angiomas, Chondrodermatitis nodularis chronica helicis, Cutaneous endometriosis, Cutaneous Leukemia, Cutaneous Lymphoma, Cutaneous meningioma, Cutaneous myxoma, Darier's disease, Dermal dendrocyte hamartoma, dermatofibroma, Dermatofibrosarcoma protuberans, Eccrine angiomatous hamartoma, Ectodermal dysplasia, Epidermal inclusion cysts, Epidermal Naevi (including but not limited to naevus sebaceous, Comedone naevus, Proteus syndromebecker naevus), Epithelioid cell histiocytoma, Familial myxovascular fibromas, Fungal skin disease (including Lobomycosis), Granular cell tumor, Glucaonoma syndrome, Genital warts, Ichthyosis (including but not limited to Ichthyosis vulgaris, Ichthyosis lamellaria, X-linked Ichthyosis, epidermolytic hyperkeratosis, Ichthyosis acquista and keratosis palmoplantaris), Idiopathic guttate hypomelanosis, Infantile acropustulosis, Infantile fibromatosis, Kaposi's sarcoma, Keloid, Keratoacanthoma, Keratocyst, Knuckle pads, Lentigo, Melanoma, Microvenular hemangioma, Morton's neuroma, Multifocal lymphangioendotheliomatosis, Multinucleate cell angiohistocytoma, Multiple cutaneous leiomyomas, Mycosis fungoides, Neuroma cutis, Neurothekeoma, Nevus flammeus, Nevus lipomatosus superficialis, Pachydermodactyly, Palisaded encapsulated neuroma, Parasitic skin diseases (including but not limited to Scabies, Pediculosis, Tungiasis, Hookwork-related cutaneous larva migrans), Pityriasis ruba pilaris, Piloleiomyomas, Plexiform fibrohistiocytic tumor, Porokeratotic eccrine ostial and Dermal duct nevus, Progressive nodular histiocytoma Psoriasis (including but not limited to Psoriatic erytroderma, Palmoplantat psoriasis, Palmoplantar pustolosis, Generalized pustular psoriasis of Zumbusch, Lingua geographica), Porokeratosis, Seborrheic dermatitis, Seborrhoeic keratosis, Rhinophyma, Solitary cutaneous leiomyoma, Spider angioma, Targetoid hemosiderotic hemangioma, Squamous cell carcinoma, Tufted angioma, Venous lake, Urticaria pigmentosa, Xanthelasmoidal mastocytosis or Zosteriform metastasis.

There may also be a use for some embodiments of the device applicator in epidermal skin rejuvenation, such as a skin peel or exfoliation, in individuals with sun damage or wrinkles.

In some embodiments, the pharmaceutical composition is a composition that includes cantharidin. In some embodiments, the ampule is capable of maintaining the stability of a composition suitable for topical administration comprising a cantharidin formulation at a starting concentration of 0.1 to 1.5% weight to volume, where in after a period of one month, the concentration of cantharidin is at least 98% of the starting concentration and after a period of six months the cantharidin concentration is at least 96% of the starting concentration. In some embodiments, the ampule is capable of maintaining the stability of a composition suitable for topical administration comprising a cantharidin at a starting concentration of 0.1 to 1.5% weight to volume, where in after a period of one month, no significant related substances have formed and after a period of six months no significant related substances have formed.

In some embodiments, a method of treating a subject having one or more skin lesions may involve administering a composition comprising cantharidin to the skin. For instance, the composition may be administered to one or more skin lesions (e.g., resulting from a molluscum cantagiosum infection, seborrheic keratosis, actinic keratosis, milia, age spots, porokeratosis or skin cancer) on the skin. The method may allow for the efficacious treatment (e.g., removal) of the skin lesion(s) with minimal or no adverse side effects (e.g., severe adverse side effects, permanent damage of the dermal tissue, scarring, excessive blistering of skin surrounding the lesion, elevated plasma cantharidin concentration, systemic exposure to cantharidin). The efficacy and/or safety of the treatment may be due, to certain features of the composition and/or prolonged exposure of the skin lesion(s) to cantharidin. For instance, a relatively high percentage of the cantharidin administered to the skin lesion(s) may be retained on the skin lesion for a relatively long period of time (e.g., greater than 6 hours). In some embodiments, the composition comprising cantharidin that is administered to the skin may allow for localized delivery of the composition and therefore cantharidin to the skin lesion(s) (e.g., to prevent exposure of surrounding skin to the composition or cantharidin and/or to prevent systemic exposure to the composition or cantharidin), relatively good adherence to the skin lesion(s), relatively high penetration of cantharidin into the skin lesion(s) over time, and/or use of a relatively low concentration (e.g., less than or equal to about 1.2% w/v) and/or bioavailability of cantharidin. In some embodiments, the methods described herein may be used for a wide variety of cutaneous disorders, including skin disorders that primarily affects the epidermis of skin. For example, the method may be used to treat molluscum cantagiosum infection, seborrheic keratosis, actinic keratosis, milia, skin cancer, age spots, and other disorders not caused by human papilloma virus.

In some embodiments, the device applicator described herein may be used to administer a composition, and the methods described herein may comprise administering a composition. Compositions suitable for use in some embodiments are described in U.S. Provisional Application, No. 62/516,061, filed Jun. 6, 2017, and entitled "Treatment of Cutaneous Disorders," and International Patent Application No. PCT/US18/36353, filed Jun. 7, 2018, and entitled "Treatment of Cutaneous Disorders," each of which are incorporated herein by reference in their entireties. Compositions suitable for use in some embodiments are also described in International Application No. PCT/US2014/052184 filed Aug. 21, 2014 and entitled "Compositions, Methods, and Systems for the Treatment of Cutaneous Disorders," which is incorporated herein by reference in its entirety.

Cantharidin is used as a blistering agent for the treatment of certain skin disorders. However, cantharidin is also classified as an extremely hazardous substance in the United States and may cause severe chemical burns as well as toxicity when ingested. Accordingly, cantharidin may cause adverse side effects (e.g., scarring) under certain conditions. For instance, historically, certain adverse effects, such as damage of the dermal tissue, blistering of normal skin surrounding the lesion, pain, and elevated plasma cantharidin concentration, have occurred during the treatment of certain skin disorders using cantharidin. Current best practices for the treatment of certain skin disorders using cantharidin include brief exposure (e.g., less than about 4 hours) of the lesion to cantharidin to prevent these adverse side effects (e.g., severe adverse side effects).

Certain aspects of the present disclosure relate to methods of treating one or more skin lesions using a pharmaceutical composition comprising cantharidin with an applicator device resulting in improved skin lesion clearance outcomes as compared to application of the pharmaceutical composition with a conventional wood stick applicator. For instance, the composition may be locally administered to one or more skin lesions (e.g., resulting from a molluscum contagiosum infection) on the skin using an applicator device. In certain embodiments, the method may comprise administering the composition two or more (e.g., three, four, five, six) times to the skin lesion(s) at a certain time interval (e.g., every 2-4 weeks, every 3 weeks±4 days) over a relatively short period of time (e.g., 12 weeks, 15 weeks). The method may allow for more efficacious treatment (e.g., shorter treatment duration, reduced frequency of administration, complete removal, higher percent reduction) of the skin lesion(s) than other methods (e.g., administration without an applicator device). For example, the present methods may allow for a relatively high percent reduction of lesions (e.g., greater than or equal to about 50%, complete removal) after one or more administrations (e.g., one, two, three, four) using the applicator device. In some instances, the present methods may allow for complete clearance (i.e., complete removal) of lesions in a relatively large percentage of subjects (e.g., greater than or equal to about 50%, greater than or equal to about 70%) after six or less (e.g., five or less, four or less) administrations of the composition using the applicator device. The enhanced efficacy of the treatment may be due to the combination of the advantageous features of the applicator device and the composition. For example, the enhanced efficacy of the treatment may be due, in part, to the ability of the applicator device to administer a composition of a given viscosity and/or phase (e.g., liquid) directly to the skin lesion(s). The methods described herein may be used for a wide variety of cutaneous disorders, including skin disorders that primarily affects the epidermis of skin. For example, the method may be used to treat molluscum contagiosum infection, seborrheic keratosis, actinic keratosis, milia, skin cancer, age spots, and other disorders not caused by human papilloma virus.

In some embodiments, a method of treating a subject having a skin lesion (e.g., resulting from a molluscum contagiosum infection) may comprise administering a composition comprising cantharidin to the skin lesion using an applicator device described herein. In certain embodiments, the composition comprises a relatively low concentration of cantharidin and have a relatively low vapor pressure (e.g., less than or equal to about 210 mm Hg at 20° C., less than or equal to about 126 mm Hg at 20° C.). For instance, the composition may comprise a relatively low concentration of cantharidin (e.g., less than or equal to about 1.2% w/v or 1.5% w/v, less than or equal to about 1% w/v, greater than or equal to about 0.5% w/v and less than or equal to about 1% w/v). The cantharidin may be dissolved or otherwise dispersed in a solvent (e.g., non-aqueous solvent). In some embodiments, the solvent in the composition may have an increased long-term stability and/or stability during use compared to solvents traditionally used in cantharidin composition, such as diethyl ether. In some such cases, the compositions, described herein, may be less susceptible to fluctuations in cantharidin concentration, e.g., due to solvent evaporation from the composition while stored in the applicator device used to house or otherwise retain the composition for a period of time. For instance, the concentration of cantharidin in the device (e.g., applicator) may remain relatively constant over time and/or after several uses. In certain embodiments, the solvent in the composition is less volatile than solvents utilized in existing and/or traditional cantharidin compositions. In certain embodiments, the solvent has a vapor pressure of less than or equal to about 350 mm Hg (e.g., less than or equal to about 210 mm Hg) at 20° C. In some such cases, the solvent is an alcohol (e.g., ethanol) and acetone. In certain cases, the solvent is a non-ether solvent and/or does not comprise diethyl ether. In certain embodiments, the composition has a vapor pressure of less than or equal to about 210 mm Hg (e.g., less than or equal to about 126 mm Hg) at 20° C. In some cases, the composition comprises a relatively small weight percentage (e.g., less than or equal to about 20 wt. %, less than or equal to about 10 wt. %) of an ether, such as diethyl ether. In certain embodiments, the composition may comprise one or more components in addition to the cantharidin and a pharmaceutically acceptable excipient (e.g., solvent). For instance, the composition may comprise a film-forming agent (e.g., polymer, nitrocellulose and/or hydroxypropyl cellulose), a plasticizer (e.g., penetration enhancer, oil, camphor and/or castor oil), a dye (e.g., gentian violet), and/or a bittering agent (e.g., denatonium benzoate). In certain embodiments, the viscosity of the composition may be less than 100 cps, less than 90 cps, less than 80 cps, less than 70 cps, less than 60 cps, less than 55 cps, more than 30 cps, more than 35 cps, about 30-100 cps, about 30-70 cps, about 35-60 cps or about 40-50 cps.

In some embodiments, the composition may have a viscosity of at least about 20 cps, at least about 30 cps, at least about 35 cps, at least about 40 cps, at least about 50 cps, at least about 55 cps, at least about 60 cps, at least about 70 cps, at least about 80 cps, at least about 90 cps, at least about 100 cps, at least about 110 cps, at least about 120 cps, or at least about 130 cps. In some embodiments, the composition may have a viscosity of less than or equal to about 150 cps, less than or equal to about 140 cps, less than or equal to about 130 cps, less than or equal to about 120 cps, less than or equal to about 110 cps, less than or equal to about 100 cps, less than or equal to about 90 cps, less than or equal to about 80 cps, less than or equal to about 70 cps, less than or equal to about 60 cps, less than or equal to about 55 cps, less than or equal to about 50 cps, less than or equal to about 40 cps, less than or equal to about 35 cps, less than or equal to about 30 cps, less than or equal to about 20 cps. Combinations of the above-referenced ranges are also possible. For example, in some embodiments, the composition may have a viscosity of about 20 cps to about 150 cps, or about 20 cps to about 130 cps, or about 30 cps to about 100 cps, or about 30 cps to about 90 cps, or about 35 cps to about 100 cps, or about 30 cps to about 110 cps, or about 30 cps to about 70 cps, or about 35 cps to about 60 cps, or about 40 cps to about 50 cps, or about 40 cps to about 80 cps.

In some embodiments, the applicator device enables the ability to routinely deliver material with the same viscosity as the viscosity of the material in the ampule. In some embodiments, at the time of contact with the skin, the delivered material has a viscosity of at least about 20 cps, at least about 30 cps, or at least about 35 cps. In some embodiments, at the time of contact with the skin, the delivered material has a viscosity of less than or equal to about 120 cps, less than or equal to about 110 cps, less than or equal to about 100 cps, or less than or equal to about 50 cps. Combinations of the above-referenced ranges are also possible. For example, in some embodiments, at the time of contact with the skin, the delivered material has a viscosity of about 20 cps to about 120 cps, or about 30 cps to about 110 cps, or about 35 cps to about 100 cps.

In some embodiments, the method comprises repeated administration of the composition using the applicator device. For instance, the method may comprise a second administration of the composition comprising cantharidin to at least a portion of the skin lesion using an applicator device. The second administration may deliver substantially the same amount of cantharidin as the first administration. In some instances, the second administration may be substantially the same as the first administration. In some embodiments, the second administration may occur a certain period of time (e.g., greater than or equal to about 1 day, greater than or equal to about 3 days, greater than or equal to about 5 days, greater than or equal to about one week, greater than or equal to about 2 weeks, greater than or equal to about 3 weeks) after the first administration. For instance, the second administration may occur greater than or equal to about 2 weeks and less than or equal to about 4 weeks (e.g., greater than or equal to about 14 days and less than or equal to about 28 days, greater than or equal to about 17 days and less than or equal to about 25 days, greater than or equal to about 18 days and less than or equal to about 24 days, greater than or equal to about 19 days and less than or equal to about 23 days, greater than or equal to about 20 days and less than or equal to about 22 days, 21 days) after the first. For instance, the second administration may be occur about 3 weeks after the first administration. In some embodiments, the second administration may occur about 3 weeks±4 days after the first administration. In some embodiments, the second administration may occur about 3 weeks±6 days after the first administration. In some embodiments, the second administration may occur about 3 weeks±5 days after the first administration. In some embodiments, the second administration may occur about 3 weeks±3 days after the first administration. In some embodiments, the second administration may occur about 3 weeks±2 days after the first administration. In some embodiments, the second administration may occur about 3 weeks±1 day after the first administration.

In some embodiments, the method may comprise a third administration of the composition comprising cantharidin to at least a portion of the skin lesion using an applicator device. In certain embodiments, the third administration may deliver substantially the same amount of cantharidin as one or more prior administrations. In some instances, the third administration may be substantially the same as the first and/or second administration. In some embodiments, the third administration may occur a certain period of time (e.g., greater than or equal to about 1 day, greater than or equal to about 3 days, greater than or equal to about 5 days, greater than or equal to about one week, greater than or equal to about 2 weeks, greater than or equal to about 3 weeks) after the second administration. For instance, the third administration may occur greater than or equal to about 2 weeks and less than or equal to about 4 weeks (e.g., greater than or equal to about 14 days and less than or equal to about 28 days greater than or equal to about 17 days and less than or equal to about 25 days, greater than or equal to about 18 days and less than or equal to about 24 days, greater than or equal to about 19 days and less than or equal to about 23 days, greater than or equal to about 20 days and less than or equal to about 22 days, 21 days) after the second administration. For instance, the third administration may occur about 3 weeks after administration of the second administration. In some embodiments, the third administration may occur about 3 weeks±4 days after the second administration. In some embodiments, the third administration may be occur about 3 weeks±6 days after the second administration. In some embodiments, the third administration may occur about 3 weeks±5 days after the second administration. In some embodiments, the third administration may occur about 3 weeks±3 days after the second administration. In some embodiments, the third administration may occur about 3 weeks±2 days after the second administration. In some embodiments, the third administration may occur about 3 weeks±1 day after the second administration.

In some embodiments, the method may comprise a fourth administration of the composition comprising cantharidin to at least a portion of the skin lesion using an applicator device. In certain embodiments, the fourth administration may deliver substantially the same percent (w/v) of cantharidin as one or more prior administrations. In some instances, the fourth administration may be substantially the same as the first, second, and/or third administrations. In some embodiments, the fourth administration may occur a certain period of time (e.g., greater than or equal to about 1 day, greater than or equal to about 3 days, greater than or equal to about 5 days, greater than or equal to about one week, greater than or equal to about 2 weeks, greater than or equal to about 3 weeks) after the third administration. For instance, the fourth administration may occur greater than or equal to about 2 weeks and less than or equal to about 4 weeks (e.g., greater than or equal to about 14 days and less than or equal to about 28 days greater than or equal to about 17 days and less than or equal to about 25 days, greater than or equal to about 18 days and less than or equal to about 24 days, greater than or equal to about 19 days and less than or equal to about 23 days, greater than or equal to about 20 days and less than or equal to about 22 days, 21 days) after the third administration. For instance, the fourth administration may occur about 3 weeks after administration of the third administration. In some embodiments, the fourth administration may be occur about 3 weeks±4 days after the third administration. In some embodiments, the fourth administration may occur about 3 weeks±6 days after the third administration. In some embodiments, the fourth administration may be occur about 3 weeks±5 days after the third administration. In some embodiments, the fourth administration may be occur about 3 weeks±3 days after the third administration. In some embodiments, the fourth administration may be occur about 3 weeks±2 days after the third administration. In some embodiments, the fourth administration may be occur about 3 weeks±1 day after the third administration.

In some embodiments, the method may comprise subsequent (e.g., fifth, sixth) administrations of the composition comprising cantharidin to at least a portion of the skin lesion using an applicator device. In certain embodiments, the subsequent administration may deliver substantially the same percent (w/v) of cantharidin as one or more prior administrations. In some instances, the subsequent administration may be substantially the same as the first, second, third, fourth or any other prior administrations. A subsequent administration (e.g., fifth administration) may occur a certain period of time (e.g., greater than or equal to about 1 day, greater than or equal to about 3 days, greater than or equal to about 5 days, greater than or equal to about one week, greater than or equal to about 2 weeks, greater than or equal to about 3 weeks) after the administration that is immediately prior (e.g., fourth administration). For instance, a subsequent administration may occur greater than or equal to about 2 weeks and less than or equal to about 4 weeks (e.g., greater than or equal to about 14 days and less than or equal to about 28 days, greater than or equal to about 17 days and less than or equal to about 25 days, greater than or equal to about 18 days and less than or equal to about 24 days, greater than or equal to about 19 days and less than or equal to about 23 days, greater than or equal to about 20 days and less than or equal to about 22 days, 21 days) after the prior administration. For instance, a subsequent administration may be occur about 3 weeks after the prior administration. In some embodiments, a subsequent administration may occur about 3 weeks±4 days after the prior administration. In some embodiments, a subsequent administration may occur about 3 weeks±6 days after the prior administration. In some embodiments, a subsequent administration may occur about 3 weeks±5 days after the prior administration. In some embodiments, a subsequent administration may occur about 3 weeks±3 days after the prior administration. In some embodiments, a subsequent administration may occur about 3 weeks±2 days after the prior administration. In some embodiments, the subsequent administration may occur about 3 weeks±1 day after the prior administration.

In general, the administration step may be repeated any suitable number of times required to treat the skin disorder. For instance, the administration step may be repeated 2 or more, 3 or more, 4 or more, 5 or more, 6 or more, 7 or more, 8 or more, 9 or more, or 10 or more times. In some embodiments, the administration step may be repeated greater than or equal to about 2 and less than or equal to about 6 times (e.g., greater than or equal to about 3 and less than or equal to about 5). In some embodiments, the administration step may be repeated 4 times. In some embodiments, the administration step may be repeated 5 times. In certain embodiments, the administration step may be repeated 3 times. In some instances, the administration step may be repeated 6 times. In some embodiments, a relatively high percent reduction of lesions may occur after greater than or equal to about 2 and less than or equal to about 6 administrations (e.g., four administrations, five administrations, six administrations). For instance, the percent reduction in lesions may be greater than or equal to about 90% (e.g., greater than or equal to about 95%, 97%) after four administration steps. As another example, the percent reduction in lesions may be greater than or equal to about 80% (e.g., greater than or equal to about 85%, 86%) after two administration steps. In some embodiments, a relatively large percentage of subjects may achieve complete clearance of skin lesions after greater than or equal to about 2 and less than or equal to about 6 administrations (e.g., four administrations, five administrations six administrations). For instance, greater than or equal to about 50% (e.g., greater than or equal to about 60%, greater than or equal to about 70%, 75%) of subjects may achieve complete clearance after four administration steps. In some instances, greater than or equal to about 70% (e.g., greater than or equal to about 80%, greater than or equal to about 90%, greater than or equal to about 95%, 100%) of subjects may achieve complete clearance after five or more administration steps (e.g., five administration steps, six administration steps). In some embodiments, a relatively large percentage of subjects may achieve 90% clearance of skin lesions after greater than or equal to about 2 and less than or equal to about 6 administrations (e.g., four administrations, five administrations six administrations). For instance, greater than or equal to about 70% (e.g., greater than or equal to about 80%, greater than or equal to about 90%, 100%) of subjects may achieve 90% clearance after four administration steps. For example, about 100% of subjects may achieve 90% clearance after four administration steps. In some embodiments, a relatively large percentage of subjects may achieve 75% clearance of skin lesions after greater than or equal to about 2 and less than or equal to about 6 administrations (e.g., four administrations, five administrations six administrations). For instance, greater than or equal to about 80% (e.g., greater than or equal to about 90%, greater than or equal to about 95%, 100%) of subjects may achieve 75% clearance after four administration steps. For example, about 100% of subjects may achieve 75% clearance after four administration steps.

In certain embodiments, the total number of administration steps performed within a certain timeframe (e.g., 3 weeks, 6 weeks, 9 weeks, 12 weeks, 15 weeks, 18 weeks, 21 weeks, 6 months, 8 months, 10 months, 12 months) and/or until a certain end point is reached (e.g., certain percent reduction in number of lesions, percent reduction in total volume of lesion(s)) may be greater than or equal to about 2 and less than or equal to about 10, greater than or equal to about 3 and less than or equal to about 10, greater than or equal to about 2 and less than or equal to about 8, greater than or equal to about 2 and less than or equal to about 6, or greater than or equal to about 3 and less than or equal to about 5. For example, the method may comprising performing two administration steps in a 6 week period of time. As another example, the method may comprise performing four administration steps in a 12 week period of time.

In general, the treatment duration may be any suitable timeframe required to treat the skin disorder. For instance, the treatment duration may be greater than or equal to about one week, greater than or equal to about 2 weeks, greater than or equal to about 3 weeks, greater than or equal to about 4 weeks, greater than or equal to about 1 month, greater than or equal to about 2 months, greater than or equal to about 3 months, greater than or equal to about 4 months, greater than or equal to about 6 months, greater than or equal to about 8 months, greater than or equal to about 10 months, greater than or equal to about 12 months. The treatment duration may refer to the time from the first administration until a certain end point is reached (e.g., certain percent reduction in number of lesions, percent reduction in total volume of lesion(s)) and/or a fixed time from the first administration. In some embodiments, the treatment duration is a fixed time from the first administration. In certain embodiments, the treatment duration is 12 weeks. In certain embodiments, the treatment duration is 13 weeks. In certain embodiments, the treatment duration is 14 weeks. In certain embodiments, the treatment duration is 15 weeks.

In some embodiments, the treatment duration may be relatively short. For instance, the treatment duration may be less than or equal to about 18 weeks, less than or equal to about 17 weeks, less than or equal to about 16 weeks, less than or equal to about 15 weeks, less than or equal to about 14 weeks, less than or equal to about 13 weeks, less than or equal to about 12 weeks, less than or equal to about 11 weeks, less than or equal to about 10 weeks, less than or equal to about 9 weeks, less than or equal to about 8 weeks, less than or equal to about 7 weeks, less than or equal to about 6 weeks, less than or equal to about 5 weeks, less than or equal to about 4 weeks, or less than or equal to about 3 weeks. In some embodiments, the treatment duration may be 12 weeks from the first administration. In some embodiments, the treatment duration may be 15 weeks from the first administration. In some embodiments, the treatment duration may be 18 weeks from the first administration. In some embodiments, the treatment duration may be 9 weeks from the first administration. In some embodiments the treatment duration may be greater than or equal to about 9 weeks and less than or equal to about 18 weeks (e.g., greater than or equal to about 9 weeks and less than or equal to about 15 weeks, greater than or equal to about 12 weeks and less than or equal to about 15 weeks, greater than or equal to about 12 weeks and less than or equal to about 18 weeks).

In some embodiments, the interval of time between each administration step (e.g., a first administration and a second administration) may be selected as desired. In some embodiments, the interval of time between at least some (e.g., each) administration step may be substantially the same. For instance, the time interval between at least some (e.g., each) administration step may be days (e.g., about 1 day, about 2 days, about 3 days, about 4 days, about 5 days, about 6 days), weeks (e.g., 1 week, 2 weeks, 3 weeks, 4 weeks), months (e.g., 1 month, 2 months, 3 months, 4 months, 5 months, 6 months, 7 months, 8 months, 9 months, 10 months, 11 months), or years (e.g., 1 year, 2 or more years). In some cases, the interval of time between each administration step (e.g., a first administration and a second administration, third administration) may be about 3 weeks (e.g., every 21 days±4 days). For example, the method may comprise administering a composition comprising cantharidin about every 3 weeks (e.g., every 21 days±4 days) for about 9 weeks. In such cases, the method comprises performing four administration steps and the interval of time between each administration step is about 3 weeks (e.g., every 21 days±4 days). In certain embodiments, the interval of time between at least some (e.g., each) administration steps may be different.

In one embodiment, the treatment method may comprise administering a composition comprising cantharidin to one or more skin lesions (e.g., resulting from a molluscum contagiosum infection) on the skin using an applicator device. The treatment duration may be greater than or equal to about 9 weeks and less than or equal to about 15 weeks (e.g., greater than or equal to about 11 weeks and less than or equal to about 13 weeks). In some cases, the treatment duration may be 12 weeks from the first administration. The method may further comprise repeating the administering step. For instance, the method may comprise two or more (e.g., three or more, four or more) administration steps. In some cases, the method may comprise four administration steps and have a treatment duration may be 12 weeks from the first administration. The interval of time between each administration step may be greater than or equal to about 1 weeks and less than or equal to about 6 weeks (e.g., greater than or equal to about 2 weeks and less than or equal to about 4 weeks). In some cases, the interval of time between the four administrations may be about 3 weeks (e.g., every 21±4 days). In some such embodiments, the composition may comprise cantharidin, a solvent (e.g., non-aqueous, non-ether, ethanol and acetone), a film-forming agent (e.g., polymer, nitrocellulose and/or hydroxypropyl cellulose), and a plasticizer (e.g., penetration enhancer, oil, camphor and/or castor oil). The composition may optionally also comprise a dye (e.g., gentian violet) and/or a bittering agent (e.g., denatonium benzoate).

For example, the composition may comprise cantharidin (e.g., greater than or equal to about 0.1 and less than or equal to about 1.2 or 1.5 weight per volume percent), acetone (e.g., greater than or equal to about 55 and less than or equal to about 65 weight per weight percent), ethanol (e.g., greater than or equal to about 25 and less than or equal to about 35 weight per weight percent), castor oil (e.g., greater than or equal to about 0.5 and less than or equal to about 2 weight per weight percent of castor oil), nitrocellulose (e.g., greater than or equal to about 2 and less than or equal to about 10 weight per weight percent), hydroxypropyl cellulose (e.g., greater than or equal to about 0.1 and less than or equal to about 2 weight per weight percent of hydroxypropyl cellulose), camphor (e.g., greater than or equal to about 0.1 and less than or equal to about 2 weight per weight percent), denatonium benzoate (e.g., greater than or equal to about 0.001 and less than or equal to about 0.01 weight per weight percent), and gentian violet (e.g., greater than or equal to about 0.0001 and less than or equal to about 0.001 weight per weight percent).

In some embodiments, the method may further comprise allowing the composition comprising cantharidin to remain on the skin lesion for greater than 6 hours (e.g., greater than or equal to 18 hours and less than or equal to about 24 hours). In some embodiments in which the administration step is repeated, the allowing step may also be repeated. In certain embodiments, the allowing step may be repeated after each administration. In some embodiments, the allowing step may be repeated after at least some but not all of the administration steps. In general, the repeated allowing step(s) may be repeated as described herein with respect to the administration steps.

In some embodiments, at least a portion of the composition may be allowed to remain on the skin lesion for a certain period of time (e.g., greater than 6 hours, greater than or equal to about 18 hours and less than or equal to about 24 hours). For example, at least some or substantially all of the solvent in the composition may evaporate leaving a material (e.g., film) on the skin (e.g., skin lesion). The material may comprise the cantharidin and a film-forming agent (e.g., nitrocellulose). In certain embodiments, the material may also comprise other components, such as a penetration enhancer, a dye, an aversive agent. In some embodiments, the remaining composition (e.g., portion of the composition remaining on the skin lesion) may have beneficial skin adhesion, flexibility, and/or safety (e.g., relatively low or no blister formation outside of the margins of the lesion) properties. For example, the remaining composition may form a film on the skin lesion. In certain embodiments, the film forms as a result of removal (e.g., via evaporation) of the solvent (e.g., substantially all) during and/or after the administration step. In some cases, the film may remain adhered to the skin lesion during normal activity by the subject and/or during minor exposure to water for a certain period of time (e.g., greater than about 6 hours, greater than about 8 hours, greater than about 12 hours, greater than about 18 hours, greater than about 24 hours, indefinitely). In certain cases, the film is relatively flexible. For instance, the film may remain relatively continuous with relatively few or no discontinuous regions during normal activity for a certain period of time. In such cases, the film may undergo minimal flaking and/or form few or no cracks during normal activity.

In some embodiments, the remaining composition may be safe. In some such cases, the composition may not induce a blister on the skin surrounding the skin lesion within about 12 or more hours (e.g., about 24 or more hours) after the administration of the composition comprising cantharidin. For example, the composition may not result in blister formation (e.g., blistering) at distance of at least about 2 mm (e.g., about 5 mm, about 10 mm, about 15 mm, about 20 mm, about 30 mm) from the margin of the skin lesion within at least 6 hours (e.g., at least about 12 hours, at least about 24 hours) after the administration step and/or after continuous contact with the composition. As another example, the composition may not cause blisters outside of the margins of the skin lesion and/or the location of administration at least 6 hours (e.g., at least about 12 hours, at least about 24 hours) after the administration step and/or after continuous contact with the composition. In some embodiments, the composition does not produce blisters having a diameter of greater than about 10 mm (e.g., about 15 mm, about 20 mm, about 25 mm, about 30 mm, about 40 mm, about 50 mm) at a certain distance (e.g., at least 1 mm, at least about 2 mm) from the margin of the skin lesion after at least 6 hours (e.g., at least about 12 hours, at least about 18 hours, at least about 24 hours) of continuous contact with the skin when a 5 mm droplet of the composition is administered to the skin. In some embodiments, the composition does not produce blisters having a diameter of greater than about 10 mm (e.g., about 15 mm, about 20 mm, about 25 mm, about 30 mm, about 40 mm, about 50 mm) at a certain distance (e.g., at least 1 mm, at least about 2 mm) from the margin of the skin lesion after at least 6 hours (e.g., at least about 12 hours, at least about 18 hours, at least about 24 hours) of continuous contact with the skin when a droplet of the composition having a volume of less than or equal to about 10 µL is administered to the skin, e.g., over a 5 mm diameter area on the skin.

In general, the treatment methods described herein may result in the separation of at least a portion of the epidermal tissue within the skin lesion from the dermal tissue without removing and/or damaging the dermal tissue. The treatment methods described herein may have a relatively high efficacy. For instance, one or more administrations of the composition using the applicator device and/or allowing the composition to remain after one or more administrations may result in the removal of the skin lesion or substantial reduction of the volume of the lesion. In some embodiments, the treatment method may have a higher efficacy than other treatment methods, including, e.g., administration of the same composition without an applicator and administration of a different composition with the same applicator. For instance, the treatment method may have a relatively high percent lesion reduction (e.g., greater than or equal to about 95%), relatively high percentage of complete clearance in subjects (e.g., greater than or equal to about 75%), relatively short treatment duration, and/or relatively low frequency of administration.

In some embodiments, the treatment methods described herein may have a relatively high percent lesion reduction. In some embodiments in which more than one skin lesions (e.g., resulting from a molluscum contagiosum infection) is present on a subject, and the composition is administered to at least some (e.g., substantially, each) of the lesions, a relatively high percentage of the treated lesions may be removed and/or the total volume of the lesions may be reduced by a relatively high percentage (e.g., greater than or equal to about 50%, greater than or equal to about 70%, greater than or equal to about 90%). For instance, in some embodiments in which more than one skin lesion is present on a subject and one or more compositions (e.g., one composition, two or more compositions, three compositions or more, four or more compositions) is administered to at least some (e.g., substantially, each) of the lesions, greater than or equal to about 40%, greater than or equal to about 45%, greater than or equal to about 50%, greater than or equal to about 55%, greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, greater than or equal to about 98%, greater than or equal to about 99%, or about 100% of the treated lesions may be removed. In certain embodiments, greater than or equal to about 40% (e.g., greater than or equal to about 45%, greater than or equal to about 50%) of the treated lesions may be removed after the first administration and/or allowing step. In some embodiments in which repeated administration is performed, greater than or equal to about 60% (e.g., greater than or equal to about 70%, greater than or equal to about 80%) of the treated lesions may be removed after the second administration and/or allowing step. In certain embodiments in which repeated administration is performed, greater than or equal to about 80% (e.g., greater than or equal to about 85%, greater than or equal to about 90%) of the treated lesions may be removed after the third administration and/or allowing step. In some embodiments in which repeated administration is performed, greater than or equal to about 90% (e.g., greater than or equal to about 92%, greater than or equal to about 95%) of the treated lesions may be removed after the fourth administration and/or allowing step. In some such embodiments, the treatment method may comprise performing four administration steps and have a duration of a 12 week period. In some instances, the interval between each administration step may be about 3 weeks (e.g., 21±4 days).

In certain embodiments, one or more administrations (e.g., two or more administrations, three or more administrations, four or more administrations) of the composition and/or allowing the composition to remain after one or more administrations may result in the complete clearance (i.e., complete removal) of the skin lesion(s) for a relatively high percentage of subjects. For instance, in some embodiments, greater than or equal to about 50%, greater than or equal to about 55%, greater than or equal to about 60%, greater than or equal to about 65%, greater than or equal to about 70%, or greater than or equal to about 75% of subjects may have complete clearance of the skin lesion(s) after two or more treatments (e.g., four or more treatments). In some instances, greater than or equal to about 70% of subjects may have complete clearance of the skin lesion(s) after two or more treatments (e.g., four or more treatments). In certain embodiments, between about 50% and about 100% (e.g., between about 50% and about 90%, between about 50% and about 100%) of subjects may have complete clearance of the skin lesion(s) after two or more treatments (e.g., four or more treatments). In some such embodiments, the treatment method may comprise performing four administration steps and have a duration of 12 weeks period.

In some embodiments, the volume of a single skin lesion may be reduced by a relatively high percentage (e.g., greater than or equal to about 50%, greater than or equal to about 60%, greater than or equal to about 75%, greater than or equal to about 90%, greater than or equal to about 99%, 100%).

It should be understood that though the methods, compositions, and devices, described herein, can be used to treat one or more body surface conditions, reference to a single skin lesion is for ease of explanation. In general, the methods, compositions, and devices, described herein, may be used to treat a plurality of skin lesions (e.g., 2 or more, 5 or more, 10 or more, 15 or more, 20 or more, 30 or more, 40 or more, 50 or more, 75 or more, 100 or more, 200 or more) on a subject having a skin disorder, such as a molluscum contagiosum infection.

In some embodiments, certain methods and compositions do not suffer from one or more limitations typically associated with cantharidin and their use. For instance, certain treatment methods may expose the skin lesion(s) to cantharidin for a relatively long period of time (e.g., greater than 6 hours, greater than or equal to 12 hours, greater than or equal to about 18 hours, greater than or equal to about 6 hours and less than or equal to about 72 hours, greater than or equal to about 18 hours and less than or equal to about 24 hours) with minimal or no adverse side effects (e.g., severe adverse side effects).

In some embodiments, the composition may be administered using the applicator device and/or the composition may be formulated such that a relatively large percentage of the composition does not spread outside the margins of the body surface area being treated after administration (e.g., topical administration). In certain embodiments, the spread of the composition to at least a portion of the body surrounding the affected area (e.g., normal tissue) may be minimized by delivering a certain volume to the affected area and/or through the use of certain applicators (e.g., precision applicator tips). In some embodiments, the composition may be formulated to allow for suitable coverage of the affected area while minimizing spread of the composition to the portion of the body surrounding the affected area. Regardless of whether the composition spreads, the composition may result in minimal or no adverse side effects (e.g., severe adverse side effects).

In some embodiments, at least a portion of the composition may be allowed to remain on the affected body area (e.g., skin lesion or other ailment) for a certain period of time (e.g., greater than 6 hours, greater than or equal to about 18 hours and less than or equal to about 24 hours). For example, at least some or substantially all of the solvent in the composition may evaporate leaving a material (e.g., film) on the affected body area (e.g., skin lesion). The material may comprise the cantharidin and a film-forming agent (e.g., nitrocellulose). In certain embodiments, the material may also comprise other components, such as a penetration enhancer, a dye, an aversive agent. In some embodiments, the remaining composition (e.g., portion of the composition remaining on the affected body area) may have beneficial adhesion, flexibility, and/or safety (e.g., relatively low or no blister formation outside of the margins of the lesion) properties. For example, the remaining composition may form a film on the skin lesion. In certain embodiments, the film forms as a result of removal (e.g., via evaporation) of the solvent (e.g., substantially all) during and/or after the administration step. In some cases, the film may remain adhered to the affected body area during normal activity by the subject and/or during minor exposure to water for a certain period of time (e.g., greater than about 6 hours, greater than about 8 hours, greater than about 12 hours, greater than about 18 hours, greater than about 24 hours, indefinitely). In certain cases, the film is relatively flexible. For instance, the film may remain relatively continuous with relatively few or no discontinuous regions during normal activity for a certain period of time. In such cases, the film may undergo minimal flaking and/or form few or no cracks during normal activity.

In some embodiments, the remaining composition may be safe. In some such cases, the composition may not induce a blister on the portion of the body surrounding the affected body area within about 12 or more hours (e.g., about 24 or more hours) after the administration of the composition comprising cantharidin. For example, the composition may not result in blister formation (e.g., blistering) at distance of at least about 2 mm (e.g., about 5 mm, about 10 mm, about 15 mm, about 20 mm, about 30 mm) from the margin of the affected body area within at least 6 hours (e.g., at least about 12 hours, at least about 24 hours) after the administration step and/or after continuous contact with the composition. As another example, the composition may not cause blisters outside of the margins of the affected body area and/or the location of administration at least 6 hours (e.g., at least about 12 hours, at least about 24 hours) after the administration step and/or after continuous contact with the composition. In some embodiments, the composition does not produce blisters having a diameter of greater than about 10 mm (e.g., about 15 mm, about 20 mm, about 25 mm, about 30 mm, about 40 mm, about 50 mm) at a certain distance (e.g., at least 1 mm, at least about 2 mm) from the margin of the affected body area after at least 6 hours (e.g., at least about 12 hours, at least about 18 hours, at least about 24 hours) of continuous contact with the skin when a 5 mm droplet of the composition is administered to the skin.

As noted above, in some embodiments, at least a portion of the composition may be allowed to remain on the affected body area for a certain period of time. In some embodiments, the composition may be allowed to remain on the affected body area for greater than about 6 hours, greater than or equal to about 8 hours, greater than or equal to about 10 hours, greater than or equal to about 12 hours, greater than or equal to about 14 hours, greater than or equal to about 16 hours, greater than or equal to about 18 hours, greater than or equal to about 20 hours, greater than or equal to about 22 hours, greater than or equal to about 24 hours, greater than or equal to about 28 hours, greater than or equal to about 32 hours, greater than or equal to about 36 hours, greater than or equal to about 40 hours, greater than or equal to about 44 hours, greater than or equal to about 48 hours, greater than or equal to about 52 hours, greater than or equal to about 56 hours, greater than or equal to about 60 hours, greater than or equal to about 64 hours, or greater than or equal to about 68 hours. In some instances, the composition may be allowed to remain on the affected body area for less than or equal to about 72 hours, less than or equal to about 68 hours, less than or equal to about 64 hours, less than or equal to about 60 hours, less than or equal to about 56 hours, less than or equal to about 52 hours, less than or equal to about 48 hours, less than or equal to about 44 hours, less than or equal to about 40 hours, less than or equal to 36 hours, less than or equal to about 32 hours, less than or equal to about 28 hours, less than or equal to about 24 hours, less than or equal to about 22 hours, less than or equal to about 20 hours, less than or equal to about 18 hours, less than or equal to about 16 hours, less than or equal to about 14 hours, less than or equal to about 12 hours, less than or equal to about 10 hours, or less than or equal to about 8 hours. All combinations of the above-referenced ranges are possible. For example, the composition may be allowed to remain on the affected body area for greater than about 6 hours and less than or equal to about 72 hours, greater than about 12 hours and less than or equal to about 72 hours, greater than about 18 hours and less than or equal to about 72 hours, greater than about 12 hours and less than or equal to about 48 hours, greater than about 18 hours and less than or equal to about 36 hours, or greater than about 18 hours and less than or equal to about 24 hours.

It should be understood that the phrases "on the affected body area", "on the skin", "on the skin lesion", "on the lesion", etc. with respect to the composition or any of its components may refer to the composition or any of its components being on top of (e.g., outside of the skin), within (e.g., contained within one or more layers of the skin, contained with the skin, contained within the lesion), and/or below one or more layers of the skin (e.g., superficial layer of the skin lesion, epidermal layer of the skin lesion). In some embodiments, at least a portion of (e.g., substantially all of) the composition or any of its components may remain on top of the affected body area. In some embodiments, at least a portion of (e.g., substantially all of) the composition or any of its components may remain within the affected body area. In some embodiments, at least a portion of (e.g., substantially all of) the composition or any of its components may be below one or more layers of the affected body area (e.g., superficial layer of the skin lesion, epidermal layer of the skin lesion).

In some embodiments, at least a portion of the solvent (e.g., substantially all) is removed from the composition during and/or after the administration step. For instance, at least a portion of the solvent (e.g., substantially all) is removed from the composition (e.g., via evaporation) after the administration step. In some such embodiments, the remaining composition may form a film on at least a portion of the affected body area. In some embodiments, the rate and/or total time for removal (e.g., evaporation) of the solvent (e.g., substantially all) from the composition may be selected to produce beneficial properties. For instance, the vapor pressure of the solvent and/or the composition may be selected to control the rate and/or total time for removal (e.g., evaporation) of the solvent (e.g., substantially all) from the composition. In some embodiments, the total time for removal (e.g., via evaporation) of at least a portion of the solvent (e.g., greater than or equal to about 50%, greater than or equal to about 75%, greater than or equal to about 90%, greater than or equal to about 95%, greater than or equal to about 99%, 100%) from the composition may be less than or equal to about 60 seconds, less than or equal to about 55 seconds, less than or equal to about 50 seconds, less than or equal to about 45 seconds, less than or equal to about 40 seconds, less than or equal to about 35 seconds, less than or equal to about 30 seconds, less than or equal to about 25 seconds, or less than or equal to about 20 seconds. In some instances, the total time for removal (e.g., evaporation) of at least a portion of the solvent (e.g., greater than or equal to about 50%, greater than or equal to about 75%, greater than or equal to about 90%, greater than or equal to about 95%, greater than or equal to about 99%, 100%) from the composition may be greater than or equal to about 10 seconds, greater than or equal to about 15 seconds, greater than or equal to about 20 seconds, greater than or equal to about 25 seconds, greater than or equal to about 30 seconds, greater than or equal to about 35 seconds, greater than or equal to about 40 seconds, greater than or equal to about 45 seconds, or greater than or equal to about 50 seconds. All combinations of the above-referenced ranges are possible (e.g., greater than about 30 seconds and less than or equal to about 60 seconds). In general, the time for removal of a least a portion of the solvent from the composition may be slower than certain traditional cantharidin composition, such as those comprising diethyl ether or a certain percentage of diethyl ether. In some embodiments, removal of at least a portion of the solvent (e.g., substantially all of the solvent) may occur through passive and/or active means.

In some embodiments using cantharidin as the administered composition, a relatively large percentage of composition (e.g., cantharidin) administered to the affected body area (e.g., skin lesion) may penetrate the affected body area (e.g., the epidermis of the skin lesion). For instance, in some embodiments, after the administration step and/or being allowed to remain on the skin for a certain period of time (e.g., 6 hours or less, 12 hours or less, 18 hours or less), greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, greater than or equal to about 90%, greater than or equal to about 95%, or greater than or equal to about 99% of the administered cantharidin may be absorbed into the tissue (e.g., epidermal tissue) of the skin lesion. Accordingly, the composition remaining on the skin (e.g., film) after a certain period of time may contain a relatively small percentage of the administered cantharidin. For instance, the composition remaining on the skin (e.g., film) may comprise less than or equal to about 75%, less than or equal to about 50%, less than or equal to about 40%, less than or equal to about 30%, less than or equal to about 20%, less than or equal to about 10%, less than or equal to about 5%, less than or equal to about 2%, less than or equal to about 1%, or less than or equal to about 0.5% of the administered cantharidin.

In some embodiments using cantharidin as the administered composition, regardless of the percentage of administered cantharidin that penetrates into the skin lesion, the plasma concentration (e.g., concentration at a single time point, concentration at all time points, maximum concentration) of cantharidin in the subject may be relatively low. For instance, the plasma concentration of cantharidin in a subject (e.g., at least some subjects, all subjects) may be less than or equal to about 30 ng/ml, less than or equal to about 25 ng/ml, less than or equal to about 20 ng/ml, less than or equal to about 15 ng/ml, less than or equal to about 10 ng/ml, less than or equal to about 8 ng/ml, less than or equal to about 5 ng/ml, less than or equal to about 4.8 ng/ml, less than or equal to about 4.5 ng/ml, less than or equal to about 4.3 ng/ml, less than or equal to about 4 ng/ml, less than or equal to about 3.8 ng/ml, less than or equal to about 3.5 ng/ml, less than or equal to about 3.3 ng/ml, less than or equal to about 3 ng/ml, less than or equal to about 2.8 ng/ml, less than or equal to about 2.5 ng/ml, less than or equal to about 2.3 ng/ml, less than or equal to about 2 ng/ml, less than or equal to about 1.8 ng/ml, less than or equal to about 1.5 ng/ml, less than or equal to about 1.3 ng/ml, less than or equal to about 1 ng/ml, less than or equal to about 0.8 ng/ml, less than or equal to about 0.5 ng/ml, less than or equal to about 0.3 ng/ml, or less than or equal to about 0.1 ng/ml at least 2 hours (e.g., at least 6 hours, at least 12 hours, at least 24 hours) after administration of the composition comprising cantharidin. For example, in embodiments in which the composition is applied to more than one skin lesions (e.g., 2 or more, 5 or more, 10 or more, 15 or more, 20 or more, 25 or more, 50 or more, 100 or more) and/or up to about 900 microliters or up to 200 mg (e.g., 170 mg) of the composition is applied to skin lesions on the subject, the plasma concentration may be less than or equal to about 3.3 ng/mL or less than or equal to about 2.5 ng/mL (e.g., less than or equal to about 1 ng/mL, less than or equal to about 0.5 ng/mL, less than or equal to about 0.1 ng/mL) at least 2 hours (e.g., 2 hours, 6 hours, 24 hours) after administration of the composition. As another example, in embodiments in which the composition is applied to more than one skin lesions (e.g., 2 or more, 5 or more, 10 or more, 15 or more, 20 or more, 25 or more, 50 or more, 100 or more) and/or up to 200 mg (e.g., 170 mg) of the composition is applied to skin lesions on the subject, the plasma concentration may be less than or equal to about 3.3 ng/mL or less than or equal to about 2.5 ng/mL (e.g., less than or equal to about 1 ng/mL, less than or equal to about 0.5 ng/mL, less than or equal to about 0.1 ng/mL) at least 2 hours (e.g., 2 hours, 6 hours, 24 hours) after administration of the composition.

In some embodiments, the plasma concentration (e.g., concentration at a single time point, concentration at all time points, maximum concentration) of cantharidin in the subject may be relatively low for a wide range of number of lesions, lesions per pound of body weight (i.e., lesions per pound), ages, body weights, total administered dosages, and/or genital involvement. For instance, the plasma concentration (e.g., concentration at a single time point, concentration at all time points, maximum concentration) may be less than or equal to about 3.3 ng/mL (e.g., less than or equal to about 2.5 ng/mL, less than or equal to about 2.5 ng/mL) at least about 2 hours (e.g., 2 hours±30 minutes, 6 hours±1 hour, 24 hours±3 hours) after administration of the composition when the composition is administered to at least 20, at least 30, at least 40, at least 50, at least 60, at least 70, at least 80, at least 90, at least 100, or at least 110 skin lesions. In some embodiments, the plasma concentration may be less than or equal to about 3.3 ng/mL (e.g., less than or equal to about 2.5 ng/mL, less than or equal to about 1 ng/mL) at least about 2 hours after administration of the composition when the lesions per pound of the subject is greater than or equal to about 0.001, greater than or equal to about 0.01, greater than or equal to about 0.1, greater than or equal to about 0.25, greater than or equal to about 0.5, greater than or equal to about 0.75, greater than or equal to about 1, greater than or equal to about 1.25, greater than or equal to about 1.75, greater than or equal to about 2, greater than or equal to about 2.25, greater than or equal to about 2.5, greater than or equal to about 2.75, or greater than or equal to about 3. For instance, the plasma concentration may be less than or equal to about 3.3 ng/mL (e.g., less than or equal to about 2.5 ng/mL, less than or equal to about 1 ng/mL) at least about 2 hours after administration of the composition in embodiments in which the lesions per pound of the subject is greater than or equal to about 0.001 and less than or equal to about 3 (e.g., greater than or equal to about 0.1 and less than or equal to about 2.5).

In some embodiments, the plasma concentration (e.g., concentration at a single time point, concentration at all time points, maximum concentration) may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of greater than or equal to about 0.1 milligrams (e.g., greater than or equal to about 0.25 mg, greater than or equal to about 0.5 mg, greater than or equal to about 0.75 mg, greater than or equal to about 1 mg, greater than or equal to about 1.5 mg, greater than or equal to about 2 mg, greater than or equal to about 2.5 mg, greater than or equal to about 3 mg, greater than or equal to about 3.5 mg, greater than or equal to about 4 mg, greater than or equal to about 4.5 mg) of the composition per pound of the subject. For instance, the plasma concentration may be less than or equal to about 3.3 ng/mL (e.g., less than or equal to about 2.5 ng/mL) at least about 2 hours after administration of greater than or equal to about 0.1 mg and less than or equal to about 6 mg (e.g., greater than or equal to about 0.5 mg and less than or equal to about 6 mg, greater than or equal to about 0.75 mg and less than or equal to about 5 mg) of the composition per pound of the subject.

In some embodiments, the plasma concentration (e.g., concentration at a single time point, concentration at all time points, maximum concentration) may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour. 24 hours±3 hours) after administration of greater than or equal to about 0.5 milligrams of the composition per lesion (e.g., greater than or equal to about 3 mg/lesion, greater than or equal to about 3.5 mg/lesion, greater than or equal to about 4 mg/lesion, greater than or equal to about 4.5 mg/lesion, greater than or equal to about 5 mg/lesion, greater than or equal to about 5.5 mg/lesion, greater than or equal to about 6 mg/lesion, greater than or equal to about 6.5 mg/lesion, greater than or equal to about 7 mg/lesion, greater than or equal to about 7.5 mg/lesion, greater than or equal to about 8 mg/lesion, greater than or equal to about 8.5 mg/lesion, greater than or equal to about 9 mg/lesion, greater than or equal to about 9.5 mg/lesion). For instance, the plasma concentration may be less than or equal to about 3.3 ng/mL (e.g., less than or equal to about 2.5 ng/mL, less than or equal to about 1 ng/mL) at least about 2 hours after administration of greater than or equal to about 3 mg/lesion and less than or equal to about 10 mg/lesion of the composition to the subject.

In some embodiments, the plasma concentration (e.g., concentration at a single time point, concentration at all time points, maximum concentration) may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of greater than or equal to about 0.01 milligrams of cantharidin per lesion (e.g., greater than or equal to about 0.01 mg/lesion, greater than or equal to about 0.02 mg/lesion, greater than or equal to about 0.03 mg/lesion, greater than or equal to about 0.04 mg/lesion, greater than or equal to about 0.05 mg/lesion, greater than or equal to about 0.06 mg/lesion, greater than or equal to about 0.07 mg/lesion, greater than or equal to about 0.08 mg/lesion, greater than or equal to about 0.09 mg/lesion, greater than or equal to about 0.1 mg/lesion, greater than or equal to about 0.2 mg/lesion, greater than or equal to about 0.3 mg/lesion, greater than or equal to about 0.4 mg/lesion, greater than or equal to about 0.5 mg/lesion). For instance, the plasma concentration may be less than or equal to about 3.3 ng/mL (e.g., less than or equal to about 2.5 ng/mL, less than or equal to about 1 ng/mL) at least about 2 hours after administration of greater than or equal to about 0.01 mg/lesion and less than or equal to about 0.5 mg/lesion (e.g., greater than or equal to about 0.07 mg/lesion and less than or equal to about 0.1 mg/lesion) of cantharidin to the subject.

In some embodiments, the plasma concentration (e.g., concentration at a single time point, concentration at all time points, maximum concentration) of cantharidin in the subject may be relatively low even in subjects having a relatively low body weight and/or age. For instance, the plasma concentration may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of the composition in subjects having a body weight of less than or equal to about 200 lb., less than or equal to about 175 lb., less than or equal to about 150 lb., less than or equal to about 125 lb., less than or equal to about 100 lb., less than or equal to about 90 lb., less than or equal to about 80 lb., less than or equal to about 70 lb., less than or equal to about 60 lb., less than or equal to about 50 lb., less than or equal to about 40 lb., or less than or equal to about 30 lb. In some instances, the plasma concentration may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of the composition in subjects having an age of less than or equal to about 20 years, less than or equal to about 18 years, less than or equal to about 15 years, less than or equal to about 12 years, less than or equal to about 10 years, less than or equal to about 8 years, less than or equal to about 5 years, or less than or equal to about 3 years. In some embodiments, the plasma concentration may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of the composition in subjects having one or more skin lesions in the genital region.

As noted above, in some embodiments, the composition may have beneficial properties that contribute, at least in part, to the efficacy and/or safety of the methods described herein. In some embodiments, the composition may comprise a relatively low concentration of cantharidin (e.g., less than or equal to about 1.2% (w/v) or 1.5% (w/v)), a non-aqueous solvent (e.g., ethanol and acetone, having a vapor pressure of less than or equal to about 350 mm Hg at 20° C.), a film-forming agent (e.g., nitrocellulose and/or hydroxypropyl cellulose), and a plasticizer (e.g., camphor and/or castor oil). In some embodiments, the composition may also comprise a dye (e.g., gentian violet) and/or a bittering agent (e.g., denatonium benzoate).

In one example, the composition may comprise cantharidin (e.g., in an amount of greater than or equal to about 0.1 and less than or equal to about 1.2 or 1.5 per volume percent, in an amount of greater than or equal to about 0.7 and less than or equal to about 0.9 weight per volume percent, 0.7 weight per volume percent), acetone (e.g., in an amount of greater than or equal to about 55 and less than or equal to about 65 weight per weight percent, in an amount of to greater than or equal to about 58 and less than or equal to about 62 weight per weight percent), ethanol (e.g., in an amount of greater than or equal to about 25 and less than or equal to about 35 weight per weight percent, in an amount of greater than or equal to about 28 and less than or equal to about 32 weight per weight percent), castor oil (e.g., in an amount of greater than or equal to about 0.5 and less than or equal to about 2 weight per weight percent, in an amount of, greater than or equal to about 1.2 and less than or equal to about 1.6 weight per weight percent), nitrocellulose (e.g, in an amount of greater than or equal to about 2 and less than or equal to about 10 weight per weight percent, in an amount of greater than or equal to about 3 and less than or equal to about 6 weight per weight percent of nitrocellulose), hydroxypropyl cellulose (in an amount of greater than or equal to about 0.1 and less than or equal to about 2 weight per weight percent, in an amount of greater than or equal to about 0.5 and less than or equal to about 1 weight per weight percent), camphor (e.g., in an amount of greater than or equal to about 0.1 and less than or equal to about 2 weight per weight percent, in an amount of greater than or equal to about 0.5 and less than or equal to about 1.2 or 1.5 weight per weight percent), denatonium benzoate (e.g., in an amount of greater than or equal to about 0.001 and less than or equal to about 0.01 weight per weight percent, in an amount of greater than or equal to about 0.004 and less than or equal to about 0.008 weight per weight percent), and/or gentian violet (e.g., in an amount of greater than or equal to about 0.0001 and less than or equal to about 0.001 weight per weight percent of gentian violet, in an amount of greater than or equal to about 0.0002 and less than or equal to about 0.0008 weight per weight percent).

In some embodiments, the overall solvent and/or the composition may have a certain vapor pressure that imparts beneficial properties to the composition. For instance, the overall solvent in the composition and/or the composition may have a vapor pressure of less than or equal to about 210 mm Hg, less than or equal to about 200 mm Hg, less than or equal to about 175 mm Hg, less than or equal to about 150 mm Hg, or less than or equal to about 126 mm Hg at 20° C. In some embodiments, the vapor pressure of the overall solvent and/or the composition may be greater than or equal to about 100 mm Hg and less than or equal to about 210 mm Hg (e.g., greater than or equal to about 100 mm Hg and less than or equal to about 200 mm Hg, greater than or equal to about 100 mm Hg and less than or equal to about 175 mm Hg, greater than or equal to about 100 mm Hg and less than or equal to about 150 mm Hg) at 20° C. In certain embodiments, the overall solvent in the composition and/or the composition may have a flash point of greater than or equal to about 4° C. In some embodiments, the overall solvent in the composition and/or the composition may not form peroxide groups upon degradation or otherwise have the propensity to from peroxides.

In certain embodiments, one or more solvent components (e.g., all solvent components) in the overall solvent, the overall solvent and/or the composition may have a vapor pressure less than or equal to about 350 mm Hg, less than or equal to about 340 mm Hg, less than or equal to about 330 mm Hg, less than or equal to about 320 mm Hg, less than or equal to about 310 mm Hg, less than or equal to about 300 mm Hg, less than or equal to about 290 mm Hg, less than or equal to about 280 mm Hg, less than or equal to about 270 mm Hg, less than or equal to about 260 mm Hg, less than or equal to about 250 mm Hg, less than or equal to about 240 mm Hg, less than or equal to about 230 mm Hg, less than or equal to about 220 mm Hg, less than or equal to about 210 mm Hg, less than or equal to about 200 mm Hg, less than or equal to about 190 mm Hg, less than or equal to about 180 mm Hg, less than or equal to about 170 mm Hg, less than or equal to about 160 mm Hg, less than or equal to about 150 mm Hg, less than or equal to about 140 mm Hg, less than or equal to about 130 mm Hg, less than or equal to about 120 mm Hg, less than or equal to about 110 mm Hg, less than or equal to about 100 mm Hg, less than or equal to about 90 mm Hg, less than or equal to about 80 mm Hg, less than or equal to about 70 mm Hg, less than or equal to about 60 mm Hg, or less than or equal to about 50 mm Hg at 20° C. In some instances, one or more solvent components in the overall solvent, the overall solvent and/or the composition may have a vapor pressure greater than or equal to about 20 mm Hg, greater than or equal to about 25 mm Hg, greater than or equal to about 30 mm Hg, greater than or equal to about 35 mm Hg, greater than or equal to about 40 mm Hg, greater than or equal to about 50 mm Hg, greater than or equal to about 60 mm Hg, greater than or equal to about 70 mm Hg, greater than or equal to about 80 mm Hg, greater than or equal to about 90 mm Hg, greater than or equal to about 100 mm Hg, greater than or equal to about 110 mm Hg, or greater than or equal to about 120 mm Hg at 20° C. All combinations of the above-referenced ranges are possible. In some embodiments, one or more solvent components (e.g., all solvent components) in the overall solvent, the overall solvent and/or the composition may have a vapor pressure of less than or equal to about 210 mm Hg (e.g., less than or equal to about 200 mm Hg, 185 mm Hg) at 20° C. In certain embodiments, one or more solvent components (e.g., all solvent components) in the overall solvent may have a flash point of greater than or equal to about 4° C. In certain embodiments, the composition may not comprise a solvent components having a flash point of less than or equal to about 4° C. In other embodiments, the composition may comprise less than or equal to about 20 wt. % of solvent components having a flash point of less than or equal to about 4° C. In some embodiments, one or more solvent components (e.g., all solvent components) in the overall solvent may not form peroxide groups upon degradation or otherwise have the propensity to from peroxide groups.

In some embodiments, the composition may comprise a relatively low percentage of diethyl ether (e.g., less than or equal to about 20% w/w, less than or equal to about 15% w/w, less than or equal to about 10% w/w, less than or equal to about 5% w/w, less than or equal to about 1% w/w, less than or equal to about 0.1% w/w, less than or equal to about 0.01% w/w) or may not comprise diethyl ether. In some embodiments, the composition may comprise a relatively low percentage of water (e.g., less than or equal to about 10% w/w, less than or equal to about 5% w/w, less than or equal to about 1% w/w, less than or equal to about 0.1% w/w, less than or equal to about 0.01% w/w) or may not comprise water.

In some embodiments, the composition may have a Reynolds number less than about 1500 at 25° C. The composition may further comprise a gelling agent. The flavorant may be selected from the group consisting of denatonium, amarogentin, gentiopicrin, sucrose octaacetate, quercetin, brucine and quassin. The colorant may be selected from the group consisting of D&C violet, isosulfan blue, methylene blue, methyl red, methyl orange, congo red, alizarin yellow, bromocresol green, FD&C Green 3, FD&C Yellow 5, and gentian violet.

The term "treatment" or "treating," as used herein, generally refers to an approach for obtaining beneficial, predetermined or desired results, including, but not limited to, therapeutic benefit and/or a prophylactic benefit. By therapeutic benefit is meant eradication or amelioration of the underlying disorder being treated, such as a skin disease or ailment, such as warts. Also, a therapeutic benefit can be achieved with the eradication or amelioration of one or more of the physiological symptoms associated with the underlying disorder, such that an improvement is observed in the patient, notwithstanding that the patient may still be afflicted with the underlying disorder. Treatment can include diagnosis of a health condition, such as warts.

The term "cantharidin," as used herein, generally refers to a compound of the structure below, or a derivative thereof that has similar activity with regard to protein phosphatase inhibition. Compounds in which boron has been substituted in place of carbon may also be considered cantharidin. Compounds with differing proportions of carbon isotopes may also be considered cantharidin (e.g., C14). Compounds with differing proportions of oxygen isotopes may also be considered cantharidin (e.g., O17). Compounds with different proportions of hydrogen isotopes may also be considered cantharidin (H3). Compounds with different proportions of carbon, oxygen, hydrogen isotopes or combinations thereof may also be considered cantharidin. Cantharidin may comprise one or more unstable radioactive elements. Cantharidin may not comprise one or more unstable radioactive elements. Cantharidin may comprise a pharmaceutically acceptable salt. Cantharidin may not comprise a pharmaceutically acceptable salt.

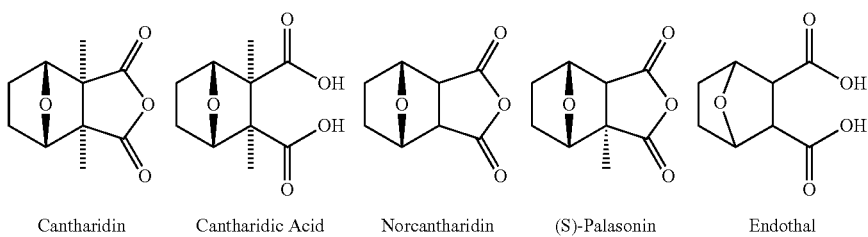

Cantharidin   Cantharidic Acid   Norcantharidin   (S)-Palasonin   Endothal

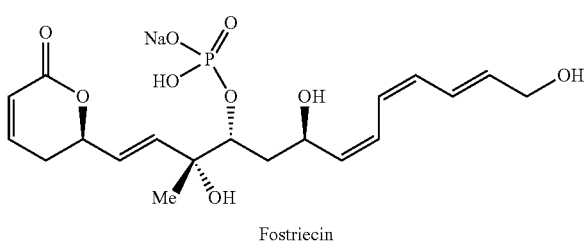

Fostriecin

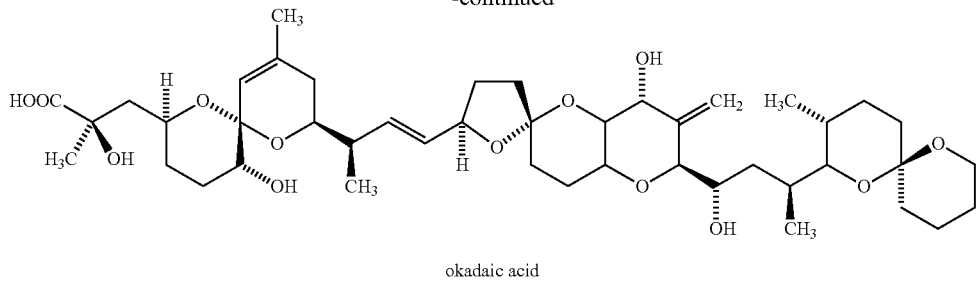

okadaic acid

Non-limiting examples of cantharidin derivatives include cantharidic acid, norcantharidin, palasonin, endothal, fostriecin and okadaic acid (see above). Other species with or without substitutions that have an exo,exo-dicarbolic acid or which may be expected to breakdown or be metabolized into the species containing an exo,exo-dicarbolic acid may also be considered "cantharidin". Other compounds that serve as inhibitors of protein phosphatases 1, 2A, 4 or 5 may also be considered "cantharidin." A cantharidin composition can comprise cantharidin alone or in addition to one or more other species, such as one or more excipients.

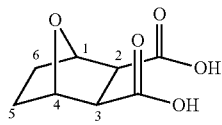

Non limiting examples of substituted exo,exo-dicarbolic acids include: 2,3-trimethylene anhydride; unsubstituted-anhydride; 5,6-dehydro-anhydride; endo-5-methyl; mono-4-chloranilide; endo-5-carboxy; 5,6-dehydro; 2-bromo; endo-5-hydroxymethyl.

Cantharidin may be produced by one or more blister beetles including but not limited to Spanish fly beetles, false blister beetles, cardinal beetles, soldier beetles, Chinese blister beetles or combinations thereof. The amount of cantharidin produced per blister beetle may be about 0.1, 0.2, 0.3, 0.4, 0.5, 0.6, 0.7, 0.8, 0.9, 1, 1.5, 2, 2.5, 3, 3.5, 4, 4.5, 5, 5.5, or about 6 mg. The amount of cantharidin produced per blister beetle may be more than about 0.1, 0.2, 0.3, 0.4, 0.5, 0.6, 0.7, 0.8, 0.9, 1, 1.5, 2, 2.5, 3, 3.5, 4, 4.5, 5, 5.5, 6 mg or more. The amount of cantharidin produced per blister beetle may be less than about 0.1, 0.2, 0.3, 0.4, 0.5, 0.6, 0.7, 0.8, 0.9, 1, 1.5, 2, 2.5, 3, 3.5, 4, 4.5, 5, 5.5, 6 mg or less. Cantharidin may be produced by biosynthesis. In some cases, biosynthesis of derivatives of cantharidin, norcantharidin, cantharidimide, or norcantharimide produces similar therapeutic effects in the user or patient. As an alternative, cantharidin can be produced fully synthetically or semi-synthetically, for example, using naturally occurring raw materials.

In some embodiments, the present disclosure provides cantharidin composition for treating skin conditions, ailments, and/or diseases, such as, but not limited to, molluscum cantagiosum. A cantharidin composition can include a therapeutically effective amount of cantharidin.

In general, the composition comprising cantharidin is administered topically using an applicator device described herein. For example, the composition may be administered to a particular location on the subject, such as the skin, without systemic administration. In some such cases, a composition, which is topically administered, may be therapeutically effective at or around the location to which the composition is administered, but may not be therapeutically effective elsewhere. In certain embodiments, the composition is administered topically to the skin, such that relatively little (e.g., plasma concentration of less than or equal to about 3.3 ng/mL, plasma concentration of less than or equal to about 2.5 ng/mL, plasma concentration of less than or equal to about 1 ng/mL) or no cantharidin is present systemically after topical administration.

The cantharidin used in the composition may be of sufficient purity to induce a therapeutic effect without associated toxicity. Purity of the cantharidin used in the composition may be between 50% and 100%. The purity of the cantharidin used may be greater than or equal to about 70%, 80%, 90%, 95%, 98%, 99%, or 99.9%.

In some embodiments, cantharidin can be formulated into preparations in solid, semi-solid, gel, or liquid forms suitable for local or topical administration, such as gels, water-soluble jellies, creams, lotions, suspensions, solutions, foams, powders, slurries, ointments, solutions, oils, capsules, tablets, pastes, suppositories, sprays, emulsions, saline solutions, dimethylsulfoxide (DMSO)-based solutions, suitable for local or topical administration. Carriers with high densities may be capable of providing an area with a prolonged exposure to the active ingredients. In contrast, a solvent/solution composition may provide more immediate exposure of cantharidin to the chosen area.

A cantharidin composition may also comprise suitable solid, semi-solid, gel or liquid phase carriers or excipients, which are compounds that may provide increased penetration of, or modify the delivery of, therapeutic molecules across the stratum corneum permeability barrier of the skin. Examples of such carriers and excipients include, but are not limited to, destructive agents (e.g., bases, acids, oxidizers), crosslinking agents (e.g. formalin or formaldehyde), humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

A cantharidin composition may include an acid or combination of acids, including, but not limited to, salicylic acid, trichloroacetic acid, hydrochloric acid, formic acid, squaric acid or nitric acid. A cantharidin composition can contain podophyllotoxin. A cantharidin composition can contain zinc oxide. A cantharidin composition can contain immunotheraputics such as imiquimod, 2,4-Dinitrochlorobenzene and/or *candida* antigen. A cantharidin composition can contain chemotherapeutics such as bleomyocin, podophyllotoxin and/or fluorouracil. A cantharidin composition can contain an oxidizer, such as hydrogen peroxide.

A cantharidin composition can include a solubilizer to ensure good solubilization and/or dissolution of cantharidin and to minimize precipitation of cantharidin in the composition. A solubilizer may be added to increase the solubility of cantharidin and/or to maintain the composition as a stable or homogeneous solution, emulsion or dispersion.

Examples of suitable solubilizers include, but are not limited to, one or more of the following: alcohols and polyols, such as acetone, ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose, hydroxyethylcellulose, hyroxypropylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, polyethylene glycol 200-100, glycofurol, transcutol, propylene glycol, dimethyl isosorbide, sorbitol, glycerol, triacetin, ethyl alcohol, PEG-400, glycofurol and propylene glycol.

The amount of a given solubilizer may be limited to a bio-acceptable amount. In some circumstances, it may be advantageous to include amounts of solubilizers in excess of bio-acceptable amounts, for example to maximize the concentration of the drug, with excess solubilizer removed prior to providing the composition to a subject using conventional techniques, such as distillation or evaporation. A solubilizer, if present, can be in a weight ratio of 10%, 25%, 50%, 100%, or up to about 200% by weight, based on the combined weight of cantharidin, and other excipients. As an alternative, substantially low amounts of solubilizer may also be used, such as 5%, 2%, 1% or even less by weight of the cantharidin composition. In some examples, the solubilizer may be present in an amount of about 1% to about 100%, or about 5% to about 25% by weight of the cantharidin composition. In some cases, a cantharidin composition includes less than a bio-acceptable amount.

A cantharidin composition may comprise one or more film-forming agents. Some examples of film-forming agent may include but are not limited to nitrocellulose, nitrocellulose derivatives, polyvinyl pyrrolidone, hydroxypropylmethylcellulose, carboxymethylcellulose and other film-forming agents or combinations thereof. The film-forming agent may be dissolved in a solvent. The film-forming agent may be dissolved in one or more solvents. A cantharidin composition may include one or more solvents. The solvent may comprise ethanol, acetone, methanol, isopropyl alcohol, butyl alcohol, pentanol, ether, water, dimethyl sulfoxide, ethyl lactate, ethyl acetate, butyl acetate, isoprorpanol, acetonitrile, food grade oils (e.g., olive oil, canola oil, sunflower oil), chlorobutanol in a waxy base, bee's wax, lanolin, petroleum jelly, silicon oil, or combinations thereof, or other solvents. In some cases, the solvent is not or does not include diethyl ether. The solvent may be acetone and an alcohol (e.g., ethanol). A cantharidin composition may comprise one or more plasticizers. Examples of such plasticizers may include but are not limited to camphor and castor oil. A cantharidin composition may comprise one or more water-mediated polymerization agents. A cantharidin composition may not comprise one or more water-mediated polymerization agents. Examples of water-mediated polymerization agents may include, but are not limited to, 2-octyl cyanoacrylate and butyl cyanoacrylate. In some cases, including a film-forming agent and a plasticizer provides a final cantharidin composition with viscosity, flexibility, durability, rigidity, ruggedness and or film-forming properties.

A cantharidin composition may comprise a dye. A cantharidin composition may comprise one or more dyes. A cantharidin composition may not comprise a dye. A dye may be an acridine, anthraquinone, arylmethane, azo, diazonium, nitro, phtalocyanine, quinone imine, tetrazolium, thiazole, xanthene, acid, basic, direct, mordant, natural or solvent dye used at a concentration sufficient to adjust the color of the cantharidin composition.

A dye may be acridine orange, acriflavine, anthracene blue SWR, alizarin, alizarin red S (mordant red 3), nuclear fast red, auramine O, chromoxane cyanin R, pararosanilin, rosanilin, magenta II, new fuchsin, methyl violet 2B, methyl violet 6B, crystal violet, Hoffman's violet, methyl green, ethyl green, acid fuchsin (acid violet 19), fast red B, fast blue B, diazonium chloride, diazonium acid sulphate, diazonium alkyl sulphate, diazonium chloride, diazonium fluborates, or diazonium benzenesulphonates, picric acid, alcian blue, luxol fast blue, toluidine blue O, thionin, azure A, azure B, azure C, neutral red, safranin O, gallocyanin, gallamin blue, iodonitrotetrazolium, nitro blue tetrazolium, thioflavine T, pyronin Y, pyronin B, rhodamine B, martius yellow (acid yellow 24), eosin Y (acid red 87), biebrich scarlet (acid red 66), suphonated pararosanilin (basic red 9), pararosanilin (basic red 9), methylene blue (basic blue 9), congo red (direct red 28), erie garnet (direct red 10), sirius red F3B (direct red 80), hematein (natural black 1), chromoxane cyanine R (mordant blue 3), celestine blue B (mordant blue 14), kermes (natural red 3), carmine (natural red 3), lac (natural red 25), hematein (natural black 1), saffron (natural yellow 6), sudan III (solvent red 23), sudan IV (solvent red 24), oil red O (solvent red 27), sudan black B (solvent black 3), or others.

A dye can include a phase change dye. A dye may include more than one phase change dye. A dye may not include a phase change dye. Some examples of phase changes dyes may include but are not limited to D&C orange, neozapon red 492, orasol red G, direct brilliant pink B, direct red 3BL, supranol brilliant red 3BW, lemon yellow 6G, light fast yellow 3G, aizen spilon yellow C-GNH, bemachrome yellow GD sub, cartasol brilliant yellow 4GF, cibanone yellow 2G, orasol black RLI, orasol black CN, savinyl black RLSN, pyrazol black BG, morfast black 101, diaazol black RN, thermoplast blue 670, orasol blue GN, savinyl blue GLS, luxol fast blue MBSN, sevron blue 5GMF, basacid blue 750, keyplast blue, neozapon black X51, classic solvent black 7, sudan blue 670, sudan yellow 146, sudan red 462, neptune red base NB543, neopen blue FF-4012, fatsol black BR, morton morplas magenta 36, or others.

A dye can include serve as an indicator dye. A dye may include more than one indicator dye. A dye may not include an indicator dye. Some examples of indicator dyes may include but are not limited to D&C violet, isosulfan blue, methylene blue, methyl red, methyl orange, congo red, alizarin yellow, bromocresol green, FD&C Green 3, FD&C Yellow 5, gentian violet, or others. A dye can include one or more phase change dyes and one or more indicator dyes or combinations thereof. Indicator dye(s) can be used at a concentration sufficient to demark the area treated with a cantharidin composition.

A cantharidin composition can contain a fluorophore. A cantharidin composition may contain more than one fluorophore. A cantharidin composition may not contain a fluorophore. A fluorophore may indicate the presence of a mineral (e.g., magnesium, calcium, zinc, copper, iron, lead, cadium, mercury, nickel, cobalt, aluminum, or lanthanides). A fluorophore may indicate the presence of magnesium. A fluorophore may indicate the presence of intracellular magnesium. A cantharidin composition may contain a fluorophore that fluoresces under an ultra violet light. Examples of fluorescent indicators that fluoresce under ultra violet light may include but are not limited to mag-indo-1 or mag-fura-2. A cantharidin composition may contain a fluorophore that fluoresces under visible light. Examples of fluorescent indicators that fluoresce under visible light may include but are not limited to magnesium green or mag-fluo-4.

A cantharidin composition can contain one or more aversive agents such as bittering agents or oral deterrents. A bittering agent is an example of a flavorant. A bittering agent or oral deterrent can be used to prevent or deter oral ingestion of the composition. A bittering agent or oral deterrent can be used to prevent or deter licking and/or ingestion of the composition prior to, during or after it has been applied to the skin. Bittering agents or oral deterrents can include, but are not limited to, denatonium (e.g., denatonium benzoate, denatonium saccharide), amarogentin, gentiopicrin, sucrose octaacetate, quercetin, brucine, and quassin. Bittering agent, denatonium benzoate may be added to a cantharidin composition.

A cantharidin composition can include one or more pharmaceutically acceptable additives or excipients. Such additives or excipients can include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In some cases, a cantharidin composition can have a pH of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, or about 12.0. As an alternative, a cantharidin composition can have a pH of at least about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, or about 12.0.

A cantharidin composition may be in liquid form. The liquid form may have a resistance to fluid flow. The liquid form may have a Reynolds number less than about 4000, 3000, 2000, 1500, 1000, 500, 400, 300, 200, or 100. The liquid form may have a Reynolds number that is about 0.1, 1, 5, 10, 25, 50, 75, 100, 250, 500, 1000, 1250, 1500, 1750, or about 2000. The liquid form may have a Reynolds number that is less than about 2000, 1750, 1500, 1250, 1000, 500, 400, 300, 250, 200, 150, 100, 75, 50, 25, 10, 5, 1, 0.1 or less.

In some cases, a cantharidin composition may have a Reynolds number less than about 4000, 3000, 2000, 1500, 1000, 500, 400, 300, 200, or 100 at a temperature of about 25° C. The liquid form may have a Reynolds number that is about 1, 5, 10, 25, 50, 75, 100, 250, 500, 1000, 1250, 1500, 1750, or about 2000 at a temperature of about 25° C. The liquid form may have a Reynolds number that is less than about 2000, 1750, 1500, 1250, 1000, 500, 400, 300, 250, 200, 150, 100, 75, 50, 25, 10, 5, 1 or less at a temperature of about 25° C.

The liquid form may have a high viscosity. The liquid form may be substantially viscous such that the liquid may not splash, drip, run, drain, leak, aerosolize out of the applicator unit. The liquid form may be substantially viscous such that the cantharidin composition remains at the location on the patient or on the user where it was administered. The liquid form may be substantially viscous such that the cantharidin composition may not flow, splash, drip, run, drain, or leak from the location on the patient or on the user where it was administered.

One or more gelling agents may be added to the liquid form to increase viscosity, for example, dextran, nitrocellulose, hydroxypropyl cellulose, ethyl cellulose, or others. The viscosity of the liquid form at ambient conditions (e.g., 25° C.) may be about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, or about 2,000,000 centipoise. The viscosity of the liquid form at ambient conditions may be more than about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, 2,000,000 centipoise or more. The viscosity of the liquid form at ambient conditions may be less than about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, 2,000,000 centipoise or less. In some cases, the viscosity is between about 10 and 10,000 centipoise.

A cantharidin composition can have the following components:

TABLE 1

Example of a cantharidin composition

| Component | Amount (% weight/weight) |
| --- | --- |
| Ethanol | 25-35% |
| Acetone | 55-65% |
| Ether | 0-10% |
| Hydroxypropylcellulose | 0.1-2.0% |
| Nitrocellulose | 2.0-10% |
| Castor Oil | 0.5-2.0% |
| Camphor | 0.1-2.0% |
| Cantharidin | 0.1-1.5% |
| Denatonium Benzoate | 0.001-0.01% |
| Gentian Violet | 0.0001-0.001% |

TABLE 2

Example of a cantharidin composition

| Component | Amount (% weight/weight) |
| --- | --- |
| Ethanol | 31.5% |
| Acetone | 60% |
| Hydroxypropylcellulose | 0.88% |
| Nitrocellulose | 4.5% |
| Castor Oil | 1.4% |
| Camphor | 0.92% |
| Cantharidin | 0.88% |
| Denatonium Benzoate | 0.006% |
| Gentian Violet | 0.0005% |

The cantharidin solutions described in Tables 1 and 2 may be prepared in the following manner. Acetone, ethanol and nitrocellulose are added to a glass vial to form a mixture. A polytetrafluoroethylene (PTFE) coated stir bar can be added and the mixture mixed until a homogenous viscous mixture is formed. Castor oil and camphor can be added to the mixture and stirred until homogenous. A 1% denatonium benzoate solution in ethanol can be added to the glass vial. A 1% gentian violet solution in ethanol can be added to the glass vial. Greater than 95% pure Cantharidin powder can be added to the glass vial. The mixture can be mixed until homogeneous. Hydroxypropylcellulose can be added and the mixture mixed until fully gelled and homogenous.

A composition, applicator device or system of the present disclosure can be used to deliver a cantharidin composition to a subject's skin which was untreated, previously treated or to be further treated. Some examples of previous treatment include, but are not limited to, removal of scar tissue, scabs or keratinized tissue via debriding, scrubbing, soaking or surgical excision. Previous treatment can also include cryotherapy, cauterization, the application or acids or bases, application of salicylic acid, lasers, surgical debridement, soaking, hydrogen peroxide or immunotherapy. Previous treatment can also include the application tape, creams, ointments, solutions, waxes or hydrophobic barriers to limit the area of skin that is exposed to the cantharidin composition. A cantharidin composition can be used prior to or concurrent with surgical resection, cryotherapy, cauterization, the application or acids or bases, application of acids, lasers, surgical debridement, soaking, hydrogen peroxide, immunotherapy or covering the treated area with an occlusive tape or bandage.

In some embodiments, the cantharidin composition is applied to the skin, and occlusive tape is placed over the treatment site. In some embodiments, the tape is kept on the treatment site for at least 12 hours, at least 24 hours, at least 36 hours, or at least 48 hours. In some embodiments, the tape is kept on the treatment site for less than or equal to 60 hours, less than or equal to 48 hours, less than or equal to 36 hours, less than or equal to 24 hours, or less than or equal to 12 hours. Combinations of the above-referenced ranges are possible. For example, in some embodiments, the tape is kept on the treatment site for about 12 hours to about 60 hours, or about 12 hours to about 48 hours, or about 12 hours to about 36 hours, or about 12 hours to about 24 hours. In some embodiments, such a treatment may be used to treat warts, e.g. common and plantar warts.

A cantharidin composition and associated applicator device or system can be used to treat the following; Acral fibrokeratoma, Acrodermatitus enterpathica, Acrokeratoelastoidosis, Actinic keratosis (solar keratoses), Adenoma sebaceum, Angiokeratoma, Atopic Dermatitis, Basal cell carcinoma, Benign fibrous histiocytomas, Bladder cancer, Bowen's disease, Breast cancer, Buschke-Ollendorff syndrome, Cervical cancer, Cervical dysplasia, Cherry angiomas, Chondrodermatitis nodularis chronica helicis, Cutaneous endometriosis, Cutaneous Leukemia, Cutaneous Lymphoma, Cutaneous meningioma, Cutaneous myxoma, Darier's disease, Dermal dendrocyte hamartoma, dermatofibroma, Dermatofibrosarcoma protuberans, Eccrine angiomatous hamartoma, Ectodermal dysplasia, Epidermal inclusion cysts, Epidermal Naevi (including but not limited to naevus sebaceous, Comedone naevus, *Proteus* syndrome-becker naevus), Epithelioid cell histiocytoma, Familial myxovascular fibromas, Fungal skin disease (including Lobomycosis), Granular cell tumor, Glucaonoma syndrome, Genital warts, Ichthyosis (including but not limited to Ichthyosis vulgaris, Ichthyosis lamellaria, X-linked Ichthyosis, epidermolytic hyperkeratosis, Ichthyosis acquista and keratosis palmoplantaris), Idiopathic guttate hypomelanosis, Infantile acropustulosis, Infantile fibromatosis, Kaposi's sarcoma, Keloid, Keratoacanthoma, Keratocyst, Knuckle pads, Lentigo, Melanoma, Microvenular hemangioma, Morton's neuroma, Multifocal lymphangioendotheliomatosis, Multinucleate cell angiohistocytoma, Multiple cutaneous leiomyomas, Mycosis fungoides, Neuroma cutis, Neurothekeoma, Nevus flammeus, Nevus lipomatosus superficialis, Pachydermodactyly, Palisaded encapsulated neuroma, Parasitic skin diseases (including but not limited to Scabies, Pediculosis, Tungiasis, Hookwork-related cutaneous larva migrans), *Pityriasis* ruba pilaris, Piloleiomyomas, Plexiform fibrohistiocytic tumor, Porokeratotic eccrine ostial and Dermal duct nevus, Progressive nodular histiocytoma Psoriasis (including but not limited to Psoriatic erytroderma, Palmoplantat psoriasis, Palmoplantar pustolosis, Generalized pustular psoriasis of Zumbusch, *Lingua geographica*), Porokeratosis, Seborrhoeic dermatitis, Seborrhoeic keratosis, Rhinophyma, Solitary cutaneous leiomyoma, Spider angioma, Targetoid hemosiderotic hemangioma, Squamous cell carcinoma, Tufted angioma, Venous lake, Urticaria pigmentosa, Xanthelasmoidal mastocytosis or Zosteriform metastasis.

Other skin ailments can also be treated with a cantharidin composition including, without limitation, acne, benign epidermal cysts, birthmarks, carbuncle, calluses, cellulitis, cold sores, corns, cutaneous candidiasis, eczema, freckles, hemangioma, hives, lupus, measles, moles, necrotizing fasciitis, pigmentation disorders (drug-induced hyperpigmentation, Dyschromatosis *symmetrica* hereditaria, dyschromatosis universalis hereditaria, familial progressive hyperpigmentation, Galli-Galli disease, hemosiderin hyperpigmentation, idiopathic guttate hypomelanosis, iron metallic discoloration, leukoderma, melasma, Mukamel syndrome, Necklace of Venus, nevus anemicus, nevus depigmentosus, Pallister-Killian syndrome, phylloid hypomelanosis, piebaldism, pigmentatio *reticularis* faciei et colli, pilar cysts, *pityriasis* alba, poikiloderma of civatte, poikiloderma vasculare atrophicans, postinflammatory hyperpigmentation, progressive macular hypomelanosis, pruritus, reticular pigmented anomaly of the flexures, reticulate acropigmentation of Kitamura, Riehl melanosis, Shah-Waardenburg syndrome, shiitake mushroom dermatitis, tar melanosis, titanium metallic discoloration, transient neonatal pustular melanosis, Vagabond's leukomelanoderma, vasospastic macules, Wende-Bauckus syndrome, X-linked reticulate pigmentary disorder, Yemenite deaf-blind hypopigmentation syndrome), psoriasis, rosacea, scars, skin cancer, skin tags, tattoo removal, vitiligo (including, but not limited to, non-segmented vitiligo, and/or segmented vitiligo trichome vitiligo, quadrichrome vitiligo, vitiligo ponctud), warts, hypohidrosis, impetigo, cutis *laxa*, decubitus ulcer, erysipelas, diaper rash, dyshidrotic eczema, canker sore, herpes stomatitis, fungal nail infection, ichthyosis vulgaris, dermatomyositis, ingrown nails, acrodermatitis, sebaceous cyst, seborrheic keratosis, pilonidal sinus, keloid, lichen planus, actinic keratosis, statis dermatitis, calluses, tinea *versicolor* pemphigoid, mouth ulcers, or shingles.

There may also be a use for a cantharidin composition in epidermal skin rejuvenation, such as a skin peel or exfoliation, in individuals with sun damage or wrinkles.

Due to its chemotactic properties, ability to induce cell arrest and apoptosis, vesicant activity and other therapeutic outcomes a cantharidin composition may have utility in combination with surgical, radiographic, immunotherapeutic, small molecule based, antibody-based, recombinant protein based, nucleic acid-based or chemotherapeutic agents. A cantharidin composition may also have utility as a second-line, third-line or forth-line therapeutic to treat patients who have failed prior therapies. Examples for use of cantharidin compositions, devices, and methods of the present disclosure include: immediately following Mohs Micrographic surgery in treating Basal Cell Carcinoma or after the failure of systemic chemotherapeutic agents in treating Mycosis fungoides or in combination with destructive therapies such as cryotherapy or hydrogen peroxide or acids or ingenol mebutate in the treatment of Actinic kerotisis or as a first line therapy in the treatment of Porokeratosis or Seborrheic keratosis.

A composition, delivery device or system of the present disclosure can be used to treat warts, Molluscum, Actinic keratosis, Seborrheic keratosis or other cutaneous hyperproliferative disorder that have failed or have been recalcitrant to prior therapy. Alternatively, a composition, delivery device or system of the present disclosure can be used as a first-line therapy. Alternatively a composition, delivery device or system of the present disclosure can be used in combination with another first line therapy.

A cantharidin composition may be used to treat patients with cancer. For instance, a cantharidin composition may be used to inhibit tumor growth and/or used to kill cancer cells directly. In some cases, a cantharidin composition may be used to kill cancer stem cells. In some cases the cantharidin composition may be used to treat benign cancerous lesions. For example, a cantharidin composition may be used to kill cancer cells with a multi-drug resistant phenotype. In some situations, norcantharidin, cantharidimide, or norcantharimide or analogues of cantharidin may be utilized instead of cantharidin.

Cantharidin compositions, applicator devices, systems, and methods can be used for other purposes, such as, for example, in the production of autologous or allogeneic skin that can be used for skin grafts or as a blistering model for the testing of drugs or an approach for eliminating residual cancer cells following a surgical procedure.

The term "excipient," as used herein, generally refers to an inactive ingredient as part of a formulation. Examples of excipients include, without limitations, dyes, flavors, binders, emollients, fillers, lubricants, antioxidants, skin penetration enhancers and preservatives. In some cases, an excipient can be selected from lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. In some embodiments, an excipient can be salicylic acid and/or podophyllotoxin.

The term "user," as used herein, generally refers to an individual using a delivery device or system to administer a composition to her or himself, or another individual, such as a subject.

The term "subject," as used herein, generally refers to an individual that is suspected of having an ailment (e.g., skin ailment), that has been diagnosed with the ailment, or is under treatment. For example, a subject can be under treatment by another individual or being administered a composition of the disclosure, either by him or herself or by another individual, such as a healthcare provider (e.g., physician, treating physician, physician's assistant, nurse) or a care provider. A subject can include asymptomatic individuals and symptomatic individuals, such as a patient. In some cases, the subject can be diagnosed with a skin disease.

The term "about" as used herein refers to within plus or minus (+/−) 10%, 9%, 8%, 7%, 6%, 5%, 4%, 3%, 2%, or 1% of the designated amount.

In some embodiments using cantharidin as the pharmaceutical composition, after the cantharidin formulation is delivered to the subject, the epithelial wart can be removed from the subject within 1, 2, 3, 4, 5, 6, 7, 8, 9, 10, 11, 12, 13, or 14 days, weeks or months. The cantharidin formulation can be delivered to the subject at least 1, 2, 3, 4, 5, 6, 7, 8, 9, or 10 times a day, week or month.

In some embodiments using cantharidin as the pharmaceutical composition, the amount of cantharidin delivered to the subject in a single administration can be between about 0.001 mg to 100 mg, about 0.1 mg to 50 mg, about 0.1 mg to 10 mg, about 0.5 mg to 10 mg, about 0.5 mg to 5 mg, about 1 mg to 5 mg, or about 1 mg to 2 mg.

In some embodiments using cantharidin as the pharmaceutical composition, the cantharidin formulation delivered to the subject can comprise at least about 0.001% (weight/volume), 0.005%, 0.01%, 0.05%, 0.1%, 0.5%, 1%, 2%, 3%, 4%, 5%, 10%, 20%, 30%, 40%, or 50% of cantharidin. In some cases, the cantharidin formulation delivered to the subject comprises at most about 50% (w/v), 40%, 30%, 20%, or 10%, or 1% of cantharidin.

In some embodiments using cantharidin as the pharmaceutical composition, the cantharidin formulation delivered to the subject can comprise greater than or equal to about 50% (w/v), about 20% (w/v), about 10% (w/v), about 5% (w/v), about 1% (w/v), about 0.5% (w/v), or about 0.1% (w/v) of excipients.

In some embodiments using cantharidin as the pharmaceutical composition, a delivery device or system can be used to deliver a cantharidin formulation to a subject at a dose up to an including about 0.001 mg/day, 0.01 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 1.5 mg/day, 2 mg/day, 2.5 mg/day, 3.0 mg/day, 3.5 mg/day, 4.0 mg/day, 4.5 mg/day, 5.0 mg/day, 5.5 mg/day, 6.0 mg/day, 6.5 mg/day, 7.0 mg/day, 7.5 mg/day, 8.0 mg/day, 8.5 mg/day, 9.0 mg/day, 9.5 mg/day, 10.0 mg/day, 11 mg/day, 12 mg/day, 13 mg/day, 14 mg/day, 15 mg/day, 16 mg/day, 17 mg/day, 18 mg/day, 19 mg/day, or 20 mg/day. As an alternative, a delivery device or system can be used to deliver a cantharidin formulation to a subject at a dose of at least about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 1.5 mg/day, 2 mg/day, 2.5 mg/day, 3.0 mg/day, 3.5 mg/day, 4.0 mg/day, 4.5 mg/day, 5.0 mg/day, 5.5 mg/day, 6.0 mg/day, 6.5 mg/day, 7.0 mg/day, 7.5 mg/day, 8.0 mg/day, 8.5 mg/day, 9.0 mg/day, 9.5 mg/day, 10.0 mg/day, 11 mg/day, 12 mg/day, 13 mg/day, 14 mg/day, 15 mg/day, 16 mg/day, 17 mg/day, 18 mg/day, 19 mg/day, or 20 mg/day.

Example 1

This example describes results of a Phase II clinical trial for the treatment of skin lesion resulting from molluscum contagiosum. Patients received four administrations of the cantharidin composition of Table 2 over 12 weeks. More patients had 75% clearance, 90% clearance, and complete clearance of the skin lesions after 12 weeks when the cantharidin composition was administered via an applicator device than placebo and when the same cantharidin composition was administered via a wooden stick. In addition, the mean percent reduction in skin lesion at 3 weeks, 6 weeks, 9 weeks, and 12 weeks was greater when the cantharidin composition was administered via an applicator device than when the same cantharidin composition was administered via a wooden stick. Placebo was estimated from the placebo arms (N=42/232) from two Phase 3 studies of ALDARA (imiquimod 5% cream) were used as an assumption for placebo.

Patients received one treatment every 3 weeks, plus or minus 4 days (i.e. one treatment every 17 to 25 days): a first treatment at week 0, a second treatment at week 3, a third treatment at week 6, and a fourth treatment at week 9. At each visit, the amount of lesion clearance was measured and recorded. At the week 12 visit, the patient did not receive a treatment, but the amount of lesion clearance was measured and recorded.

The estimated placebo resulted in 18% of patients reaching full clearance of skin lesions at week 12 with four treatments, while the cantharidin composition of Table 2 resulted in 46% of patients reaching full clearance when the cantharidin composition was administered via a conventional wooden stick applicator, with a P-value of greater than 0.0015.

Patients that received a cantharidin composition that was administered via an applicator device had a higher percent reduction in lesions than patients that received the same cantharidin composition administered via a wooden stick and placebo.

Experiments have also shown that using a device applicator similar to the embodiment shown in FIGS. 1-21 to apply a pharmaceutical composition of Table 2, is significantly better than a conventional wood stick applicator at clearing skin lesions from molluscum contagiosum.

With a conventional wood stick applicator, the pharmaceutical composition is held within a container having a lid. During treatment, the lid is removed and the wood stick applicator is dipped into the container to coat an end of the wood stick applicator with pharmaceutical composition. Finally, the wood stick applicator is moved toward each skin lesion of the patient to apply the pharmaceutical composition onto the lesion. The practitioner may dip the wood stick applicator back into the container to obtain more pharmaceutical composition.

Patients received a treatment every 3 weeks, plus or minus 4 days (i.e. one treatment every 17 to 25 days): a first treatment at week 0, a second treatment at week 3, a third treatment at week 6, and a fourth treatment at week 9. At each visit, the amount of lesion clearance was measured and recorded. At the week 12 visit, the patient did not receive a treatment, but the amount of lesion clearance was measured and recorded.

Figure 22:
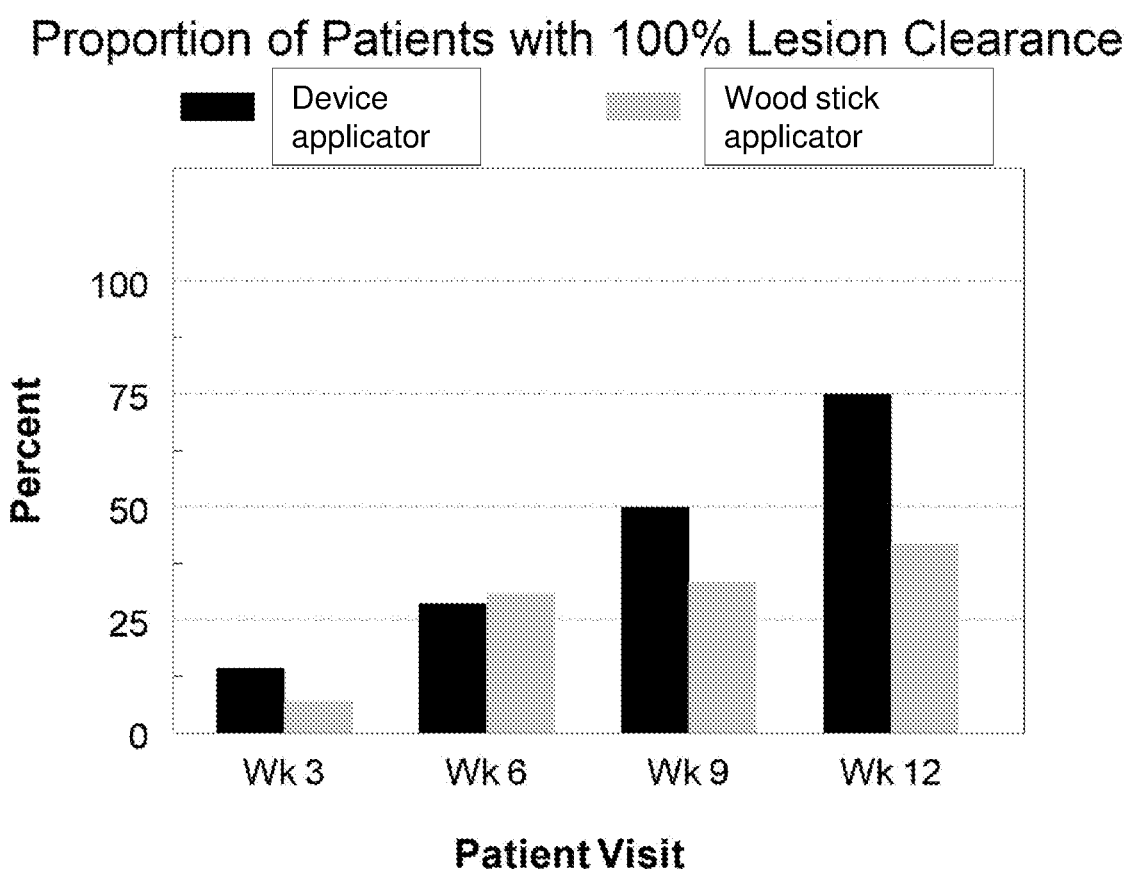
FIG. 22 is a graph showing that using a device applicator described herein to apply a pharmaceutical composition resulted in more skin lesion clearance as compared to using a conventional wood stick applicator.

Data showing the proportion of patients with 100% lesion clearance from treatment with the wood stick applicator compared with the device applicator is shown in FIG. 22. At week 12, with four treatments, the pharmaceutical composition with wood stick applicator resulted in 46% of patients reaching full clearance of skin lesions, while the pharmaceutical composition with device applicator resulted in 75% of patients reaching full clearance of skin lesions. In addition, at weeks 3 and 9, higher skin lesion clearance was observed with the device applicator as compared to the wood stick applicator.

Figure 23:
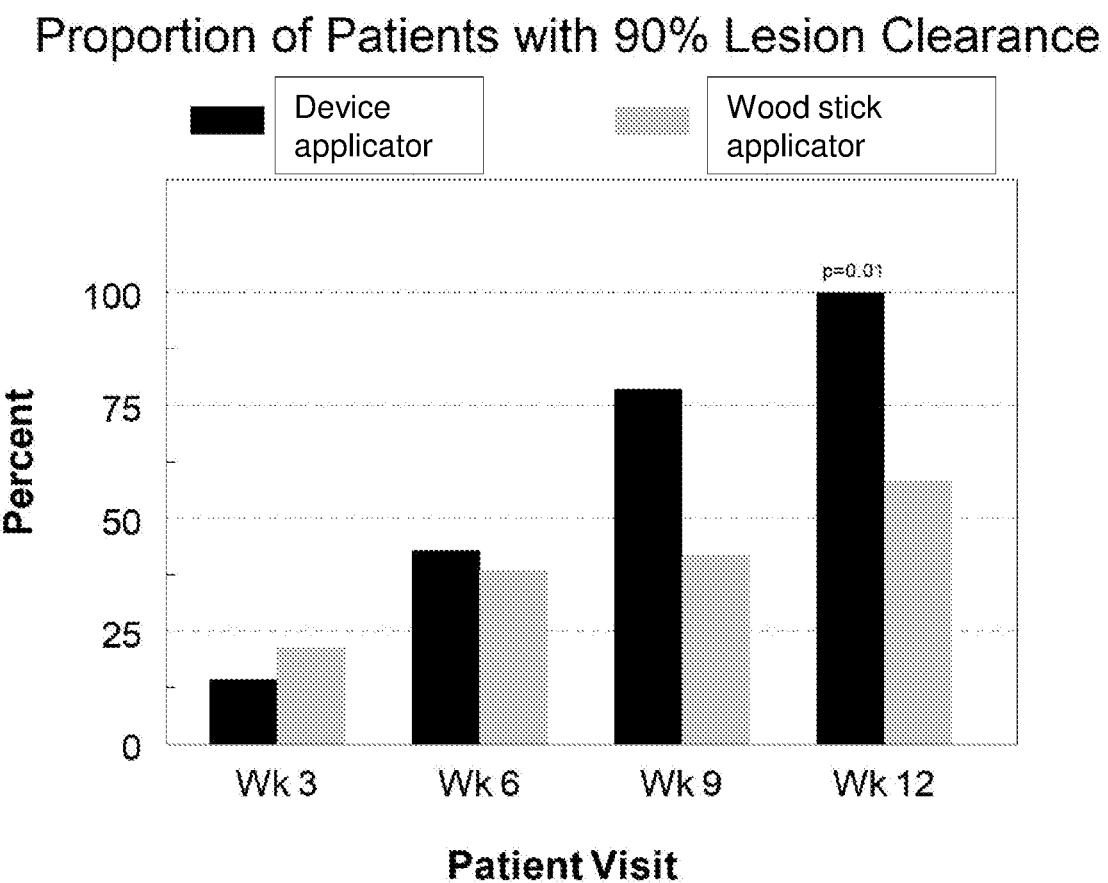
FIG. 23 is a graph showing that using a device applicator described herein to apply a pharmaceutical composition resulted in more skin lesion clearance as compared to using a conventional wood stick applicator.

Data showing the proportion of patients with at least 90% lesion clearance from treatment with the wood stick applicator compared with the device applicator is shown in FIG. 23. At week 12, with four treatments, the pharmaceutical composition with wood stick applicator resulted in 59% of patients reaching at least 90% lesion clearance, while the pharmaceutical composition with device applicator resulted in 100% of patients reaching at least 90% lesion clearance. In addition, at weeks 6 and 9, higher skin lesion clearance was observed with the device applicator as compared to the wood stick applicator.

Figure 24:
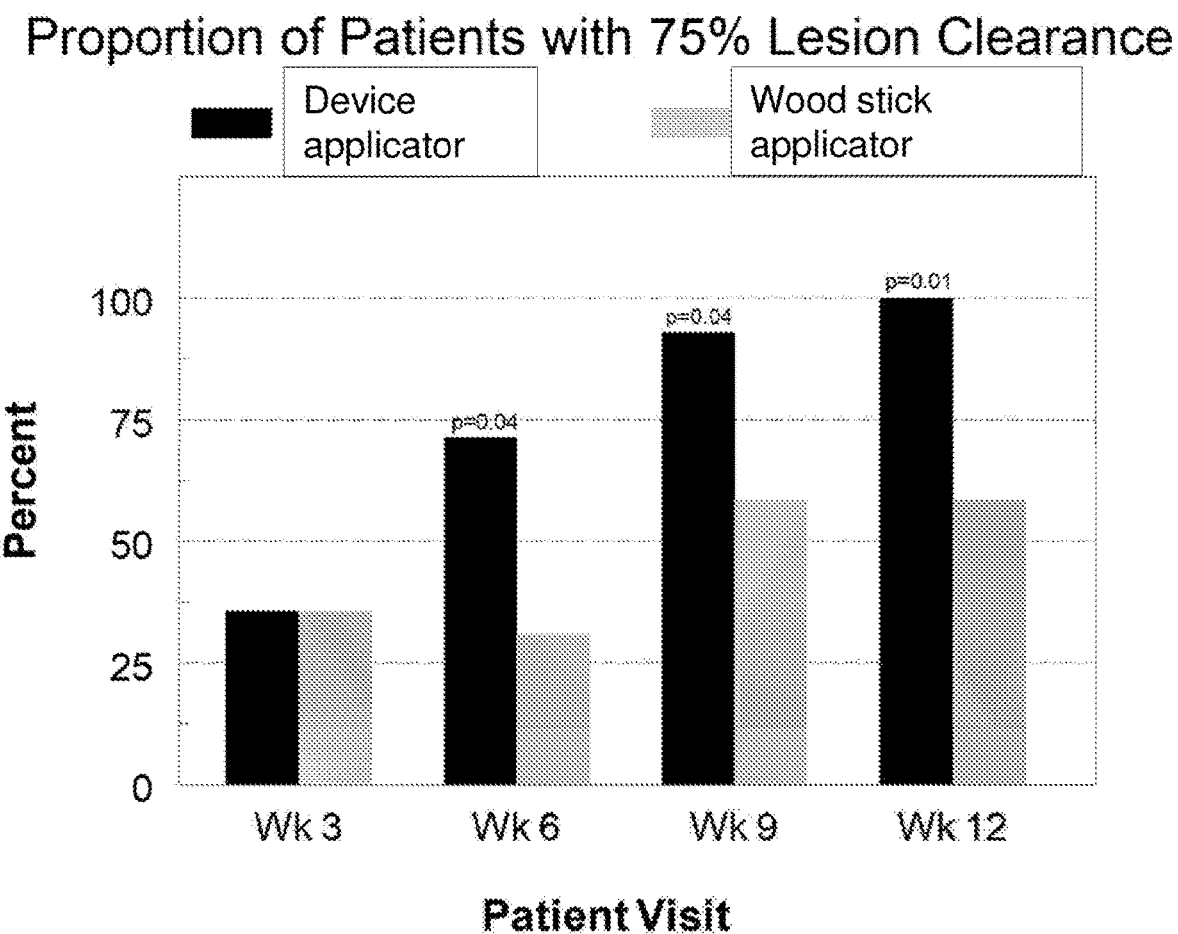
FIG. 24 is a graph showing that using a device applicator described herein to apply a pharmaceutical composition resulted in more skin lesion clearance as compared to using a conventional wood stick applicator.

Data showing the proportion of patients with at least 75% lesion clearance from treatment with the wood stick applicator compared with the device applicator is shown in FIG. 24. At week 12, with four treatments, the pharmaceutical composition with wood stick applicator resulted in 59% of patients reaching at least 75% lesion clearance, while the pharmaceutical composition with device applicator resulted in 100% of patients reaching at least 75% lesion clearance. In addition, at weeks 6 and 9, higher skin lesion clearance was observed with the device applicator as compared to the wood stick applicator.

Figure 25:
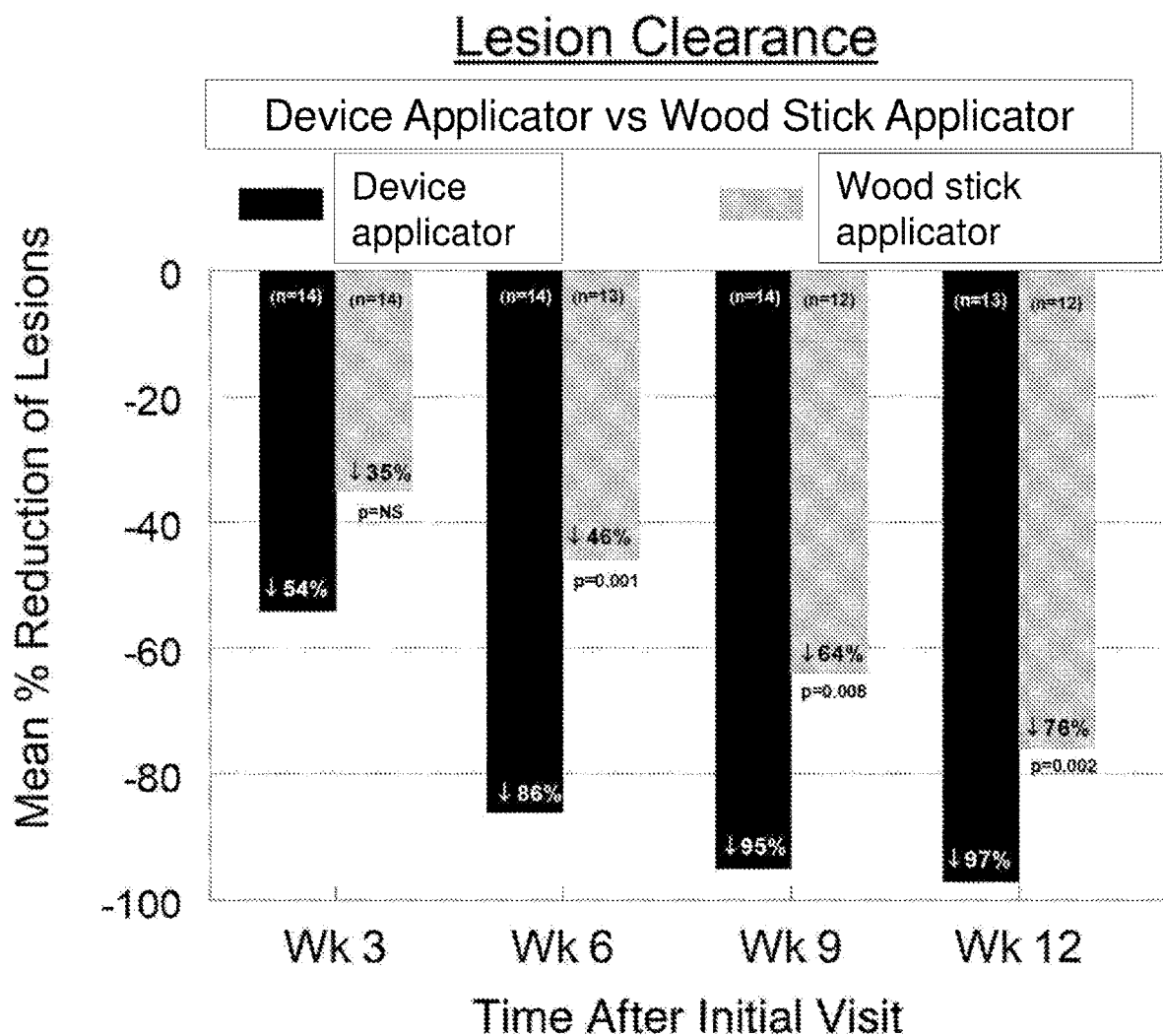
FIG. 25 is a graph showing that using a device applicator described herein to apply a pharmaceutical composition resulted in more skin lesion clearance as compared to using a conventional wood stick applicator.

Data showing the mean percent reduction of lesions of patients receiving treatment from the device applicator as compared to patients receiving treatment from the conventional wood stick applicator is shown in FIG. 25. At week 12, with four treatments, the pharmaceutical composition with wood stick applicator resulted in a mean reduction of lesions of 76%, while the pharmaceutical composition with device applicator resulted in a mean reduction of lesions of 97%, with a p-value equal to 0.002.

In addition, at weeks 3, 6 and 9, higher mean percent reduction of lesions was observed with the device applicator as compared to the wood stick applicator.

Example 2

This example describes results of a Phase II clinical trial for the treatment of skin lesion resulting from molluscum contagiosum.

Patients received one treatment every 3 weeks, plus or minus 4 days (i.e. one treatment every 17 to 25 days): a first treatment at week 0, a second treatment at week 3, a third treatment at week 6, and a fourth treatment at week 9. At each visit, the amount of lesion clearance was measured and recorded. At the week 12 visit, the patient did not receive a treatment, but the amount of lesion clearance was measured and recorded.

Experiments have shown that using a device applicator similar to the embodiment shown in FIGS. 1-21 to apply a pharmaceutical composition of Table 2, is significantly better than a conventional wood stick applicator at clearing skin lesions from molluscum contagiosum.

With a conventional wood stick applicator, the pharmaceutical composition is held within a container having a lid. During treatment, the lid is removed and the wood stick applicator is dipped into the container to coat an end of the wood stick applicator with pharmaceutical composition. Finally, the wood stick applicator is moved toward each skin lesion of the patient to apply the pharmaceutical composition onto the lesion. The practitioner may dip the wood stick applicator back into the container to obtain more pharmaceutical composition.

Patients received a treatment every 3 weeks, plus or minus 4 days (i.e. one treatment every 17 to 25 days): a first treatment at week 0, a second treatment at week 3, a third treatment at week 6, and a fourth treatment at week 9. At each visit, the amount of lesion clearance was measured and recorded. At the week 12 visit, the patient did not receive a treatment, but the amount of lesion clearance was measured and recorded.

Figure 26:
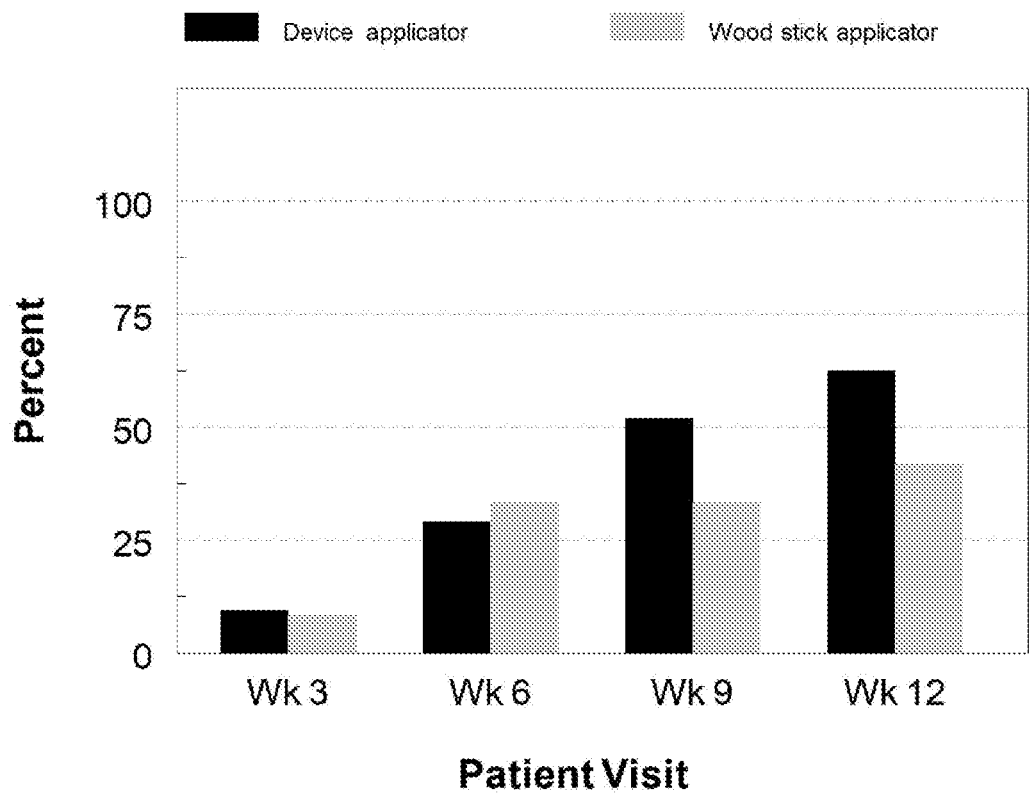
FIG. 26 is a graph showing that using a device applicator described herein to apply a pharmaceutical composition resulted in more skin lesion clearance as compared to using a conventional wood stick applicator.

Data showing the proportion of patients with 100% lesion clearance from treatment with the wood stick applicator compared with the device applicator is shown in FIG. 26. At week 12, with four treatments, the pharmaceutical composition with wood stick applicator resulted in about 46% of patients reaching full clearance of skin lesions, while the pharmaceutical composition with device applicator resulted in about 63% of patients reaching full clearance of skin lesions. In addition, at weeks 3 and 9, higher skin lesion clearance was observed with the device applicator as compared to the wood stick applicator.

Figure 27:
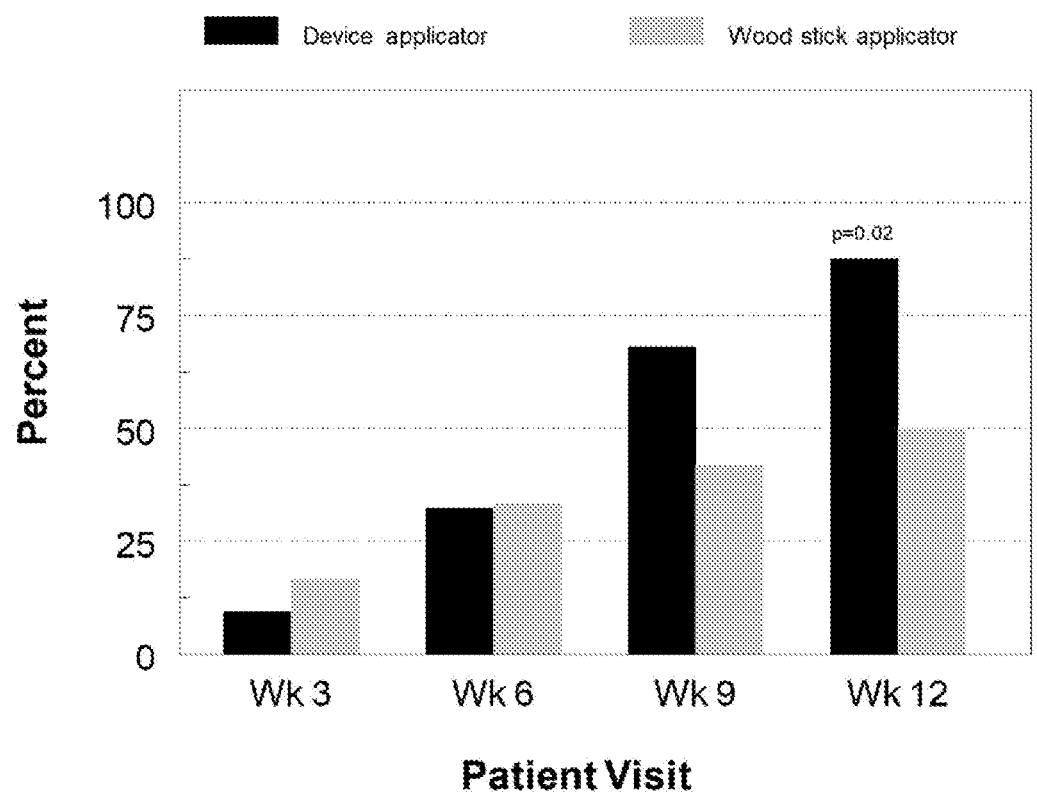
FIG. 27 is a graph showing that using a device applicator described herein to apply a pharmaceutical composition resulted in more skin lesion clearance as compared to using a conventional wood stick applicator.

Data showing the proportion of patients with at least 90% lesion clearance from treatment with the wood stick applicator compared with the device applicator is shown in FIG. 27. At week 12, with four treatments, the pharmaceutical composition with wood stick applicator resulted in about 67% of patients reaching at least 90% lesion clearance, while the pharmaceutical composition with device applicator resulted in about 88% of patients reaching at least 90% lesion clearance. In addition, at week 9, higher skin lesion clearance was observed with the device applicator as compared to the wood stick applicator.

Figure 28:
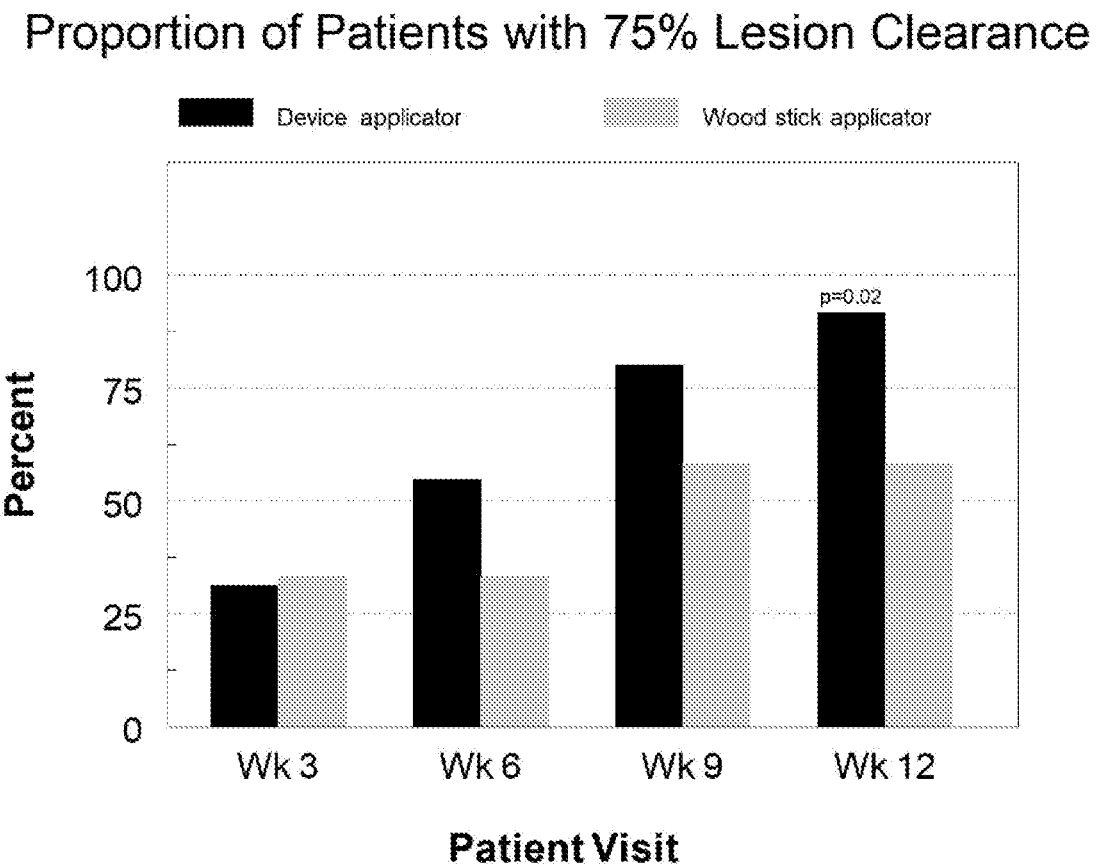
FIG. 28 is a graph showing that using a device applicator described herein to apply a pharmaceutical composition resulted in more skin lesion clearance as compared to using a conventional wood stick applicator.

Data showing the proportion of patients with at least 75% lesion clearance from treatment with the wood stick applicator compared with the device applicator is shown in FIG. 28. At week 12, with four treatments, the pharmaceutical composition with wood stick applicator resulted in about 59% of patients reaching at least 75% lesion clearance, while the pharmaceutical composition with device applicator resulted in about 92% of patients reaching at least 75% lesion clearance. In addition, at weeks 6 and 9, higher skin lesion clearance was observed with the device applicator as compared to the wood stick applicator.

Figure 29:
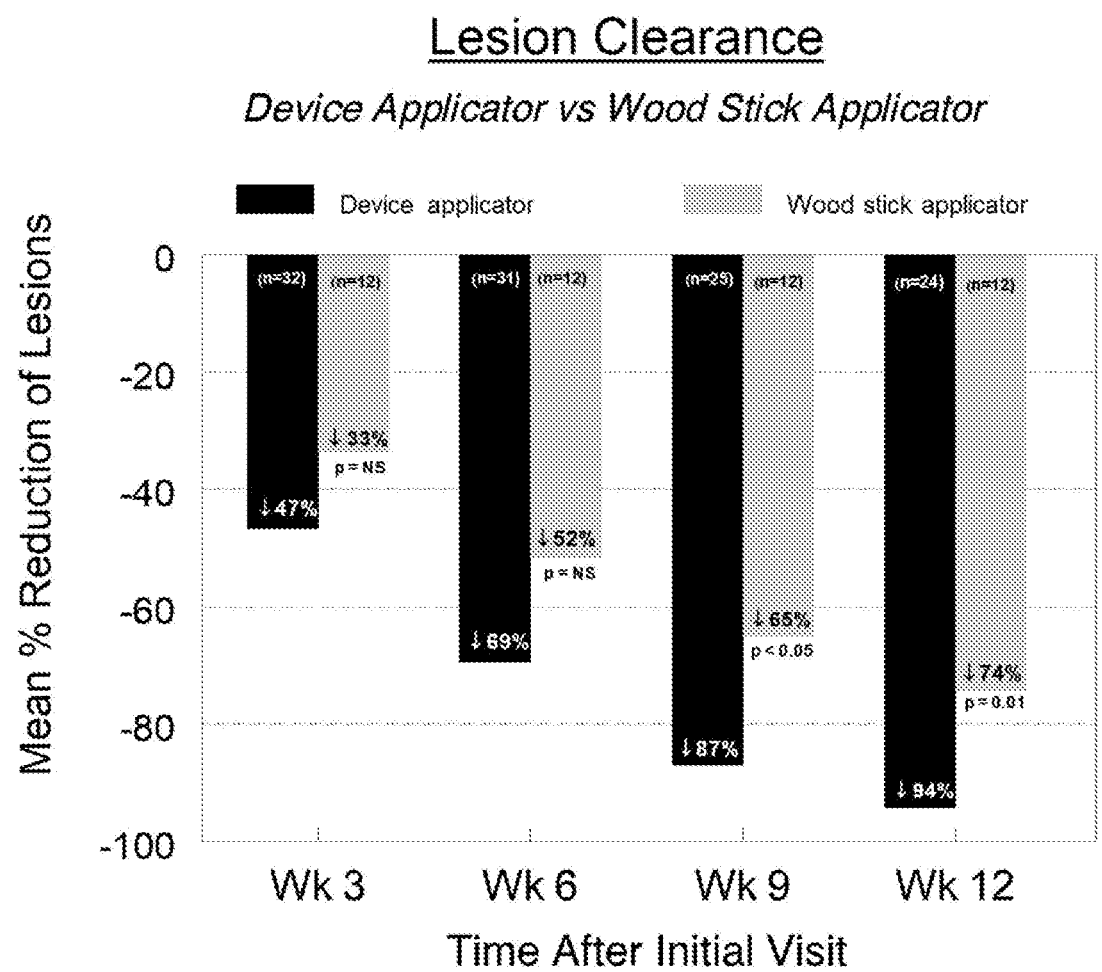
FIG. 29 is a graph showing that using a device applicator described herein to apply a pharmaceutical composition resulted in more skin lesion clearance as compared to using a conventional wood stick applicator.

Data showing the mean percent reduction of lesions of patients receiving treatment from the device applicator as compared to patients receiving treatment from the conventional wood stick applicator is shown in FIG. 29. At week 12, with four treatments, the pharmaceutical composition with wood stick applicator resulted in a mean reduction of lesions of 74%, while the pharmaceutical composition with device applicator resulted in a mean reduction of lesions of 94%, with a p-value equal to 0.01.

In addition, at weeks 3, 6 and 9, higher mean percent reduction of lesions was observed with the device applicator as compared to the wood stick applicator.

Example 3

This example describes pharmacokinetic results from a Phase II clinical trial for the treatment of skin lesion resulting from Molluscum contagiosum. Patients received administrations of the cantharidin composition in Table 2 to Molluscum contagiosum lesions every 21 days for a maximum of 4 sessions or until complete clearance. Blood samples for systemic exposure evaluation were collected on Day 1, prior to the drug application, and 2 (±30 minutes), 6 (±1 hour) and 24 (±3 hours) hours post-application. The average age of the subjects was 7±3.5 years. The average body weight of the subjects was 58±34.6 lb. The average number of lesions per subject was 43.7±24.2.

Only one of the seventeen subjects had a plasma concentration of cantharidin above the lower limit of quantification (i.e., 2.5 ng/ml). The plasma concentration of cantharidin for all subjects was less than 3.3 ng/ml at all times sampled. Moreover, subjects (i) as young as 2 years old, (ii) having over 100 lesions, (iii) having genital lesions, and (iv) with as many as 2.26 lesions per lb had a plasma concentration of cantharidin below the lower limit of quantification. Table 10 shows the gender, age, weight, number of lesions, genital involvement, systemic exposure, lesions per pound of the subject, mg of composition used per treatment session, mg of composition per lesion, and mg of composition per pound of the subject for the subjects in the clinical trial.

TABLE 3

Subject Demographic and Pharmacokinetic Data

| Sex | Age (yr) | Wt. (lb) | No. of lesions | Genital involvement | Exposure (ng/ml) | Lesions/lb | mg* (mg#) | mg*/lesion (mg#/lesion) | mg*/lb (mg#/lb) |
|---|---|---|---|---|---|---|---|---|---|
| F | 6 | 47.1 | 45 | No | <2.5 | 0.96 | — | — | — |
| M | 13 | 88.4 | 22 | Yes | <2.5 | 0.25 | — | — | — |
| F | 9 | 68 | 27 | No | <2.5 | 0.40 | — | — | — |
| M | 8 | 58 | 32 | No | <2.5 | 0.55 | — | — | — |
| M | 15 | 173 | 83 | No | <2.5 | 0.48 | — | — | — |
| F | 4 | 39 | 65 | No | <2.5 | 1.67 | — | — | — |
| M | 5 | 47 | 43 | No | <2.5 | 0.91 | — | — | — |
| M | 5 | 37 | 26 | No | <2.5 | 0.70 | 30 (0.26) | 1.2 (0.01) | 0.8 (0.01) |
| F | 4 | 34 | 47 | No | <2.5 | 1.38 | 160 (1.4) | 3.4 (0.03) | 4.7 (0.04) |
| M | 6 | 44 | 41 | No | <2.5 | 0.93 | 133 (1.17) | 3.2 (0.03) | 3.0 (0.03) |
| F | 8 | 50 | 29 | No | <2.5 | 0.58 | 136 (1.2) | 4.7 (0.04) | 2.7 (0.02) |
| M | 2 | 29.5 | 24 | No | 3.3 | 0.81 | 74 (0.65) | 3.1 (0.03) | 2.5 (0.02) |
| M | 8 | 65 | 29 | No | <2.5 | 0.45 | 85 (0.75) | 2.9 (0.03) | 1.3 (0.01) |
| F | 6 | 50 | 113 | Yes | <2.5 | 2.26 | 122 (1.07) | 1.1 (0.01) | 2.4 (0.02) |
| F | 6 | 43 | 30 | No | <2.5 | 0.70 | 108 (0.95) | 3.6 (0.03) | 2.5 (0.02) |
| M | 3 | 26 | 31 | No | <2.5 | 1.19 | 122 (1.07) | 3.9 (0.03) | 4.7 (0.04) |
| M | 11 | 87 | 56 | No | <2.5 | 0.64 | 167 (1.47) | 3.0 (0.03) | 1.9 (0.02) |

Mg* refers to milligrams of the composition.
Mg# refers to milligrams of cantharidin.

While certain embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An applicator device for dispensing a pharmaceutical composition for topical administration of the pharmaceutical composition to a subject, comprising:
    a tube;
    an ampule positioned within the tube;
    a pharmaceutical composition contained within the ampule;
    a dispenser tip attached to the tube, the dispenser tip having a tapered tip and a drip guard comprising a trough configured to receive fluid running down an outer surface of the tapered tip, wherein the drip guard includes one or more grooves formed on an external side of the drip guard.

2. The applicator device of claim 1, further comprising a filter positioned within the tapered tip of the dispenser tip, the filter being constructed and arranged to permit passage of fluid and inhibit passage of broken ampule shards having a particle size of at least 150 um.

3. The applicator device of claim 2, wherein the filter is held within the dispenser tip via an interference fit between the filter and an inner surface of the tapered tip.

4. The applicator device of claim 1, wherein the tapered tip of the dispenser tip is configured to dispense discrete droplets of the pharmaceutical composition.

5. The applicator device of claim 1, wherein the dispenser tip includes an inner surface and an outer surface, wherein at least a portion of the inner surface is tapered at a first taper angle and at least a portion of the outer surface is tapered at a second taper angle.

6. The applicator device of claim 5, wherein the second taper angle is different from the first taper angle.

7. The applicator device of claim 1, wherein the dispenser tip includes a first portion and a second portion, wherein the first portion has a tapering inner diameter, and the second portion has a constant inner diameter.

8. The applicator device of claim 1, wherein the tapered tip ends in a distal opening having an internal diameter of less than 0.02 inches and external diameter of less than 0.05 inches.

9. The applicator device of claim 1, further comprising a cap having an opening for receiving the dispenser tip, wherein the cap has a closed position in which at least a portion of the dispenser tip is passed through the opening, and wherein the cap is coupled to the dispenser tip and positioned over at least a portion of the dispenser tip.

10. The applicator device of claim 9, wherein when the cap is in the closed position, venting of the dispenser tip is permitted through the opening of the cap.

11. The applicator device of claim 10, wherein venting of the dispenser tip occurs only through the opening of the cap.

12. The applicator device of claim 10, wherein venting of the dispenser tip is permitted through the opening of the cap at locations adjacent the one or more grooves formed on the external side of the drip guard.

13. The applicator device of claim 1, wherein at least a portion of the dispenser tip is attached to the tube to form a fluid-tight seal between the dispenser tip and the tube.

14. The applicator device of claim 1, wherein the applicator device is constructed and arranged to create a vacuum inside the tube when the tube is squeezed and then released.

15. The applicator device of claim 1, wherein the pharmaceutical composition comprises a compound selected from the group consisting of: cantharidin, antifungals, antibacterials, antivirals, corticosteroids, steroids, immunostimulants, chemotherapeutics, keratolytics, antihistamines, and anti-inflammatory agents.

16. The applicator device of claim 1, wherein the pharmaceutical composition comprises cantharidin, acetone, ethanol, a plasticizer, and a film-forming agent.

17. The applicator device of claim 16, wherein the composition further comprises hydroxypropylcellulose, nitrocellulose, castor oil, camphor, denatonium benzoate, and gentian violet.

18. The applicator device of claim 17, wherein the composition further comprises ether.

19. The applicator device of claim 1, wherein the composition is ether-free.

20. An applicator device for dispensing a pharmaceutical composition for topical administration of the pharmaceutical composition to a subject, comprising:
    a tube;
    an ampule positioned within the tube;
    a pharmaceutical composition contained within the ampule;
    a dispenser tip attached to the tube, the dispenser tip having a tapered tip and a drip guard comprising a trough configured to receive fluid running down an outer surface of the tapered tip,
    wherein the drip guard includes one or more grooves formed on an external side of the drip guard, and
    wherein the pharmaceutical composition comprises:
        greater than or equal to 25 and less than or equal to 35 weight per weight percent of ethanol;
        greater than or equal to 55 and less than or equal to 65 weight per weight percent of acetone;
        less than or equal to 10 weight per weight percent of ether;

greater than or equal to 0.1 and less than or equal to 2 weight per weight percent of hydroxypropylcellulose;

greater than or equal to 2.0 and less than or equal to 10 weight per weight percent of nitrocellulose;

greater than or equal to 0.5 and less than or equal to 2 weight per weight percent of castor oil;

greater than or equal to 0.1 and less than or equal to 1.5 weight per weight percent of cantharidin;

greater than or equal to 0.001 and less than or equal to 0.01 weight per weight percent of denatonium benzoate; and greater than or equal to 0.0001 and less than or equal to 0.001 weight per weight percent of gentian violet.

* * * * *

UNITED STATES PATENT AND TRADEMARK OFFICE
CERTIFICATE OF CORRECTION

PATENT NO. : 12,290,651 B2  
APPLICATION NO. : 16/621854  
DATED : May 6, 2025  
INVENTOR(S) : Matthew Gene Davidson et al.

Page 1 of 1

It is certified that error appears in the above-identified patent and that said Letters Patent is hereby corrected as shown below:

In the Claims

Column 57, Line 54, Claim 2, "um" should read --µm--.

Signed and Sealed this  
Tenth Day of June, 2025

Coke Morgan Stewart  
*Acting Director of the United States Patent and Trademark Office*